(12) United States Patent
Williams et al.

(10) Patent No.: US 11,883,594 B2
(45) Date of Patent: Jan. 30, 2024

(54) RESPIRATORY RATE MONITORING FOR RESPIRATORY FLOW THERAPY SYSTEMS

(71) Applicant: Fisher & Paykel Healthcare Limited, Auckland (NZ)

(72) Inventors: Rhys Matthew James Williams, Auckland (NZ); Charles Grady Cantrell, Auckland (NZ); David Martin Russell, Auckland (NZ); Brett James Ryan, Auckland (NZ); Bryn Alan Edwards, Auckland (NZ); Anton Kim Gulley, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 582 days.

(21) Appl. No.: 16/762,707

(22) PCT Filed: Nov. 22, 2018

(86) PCT No.: PCT/IB2018/059195
§ 371 (c)(1),
(2) Date: May 8, 2020

(87) PCT Pub. No.: WO2019/102384
PCT Pub. Date: May 31, 2019

(65) Prior Publication Data
US 2021/0113796 A1    Apr. 22, 2021

Related U.S. Application Data

(60) Provisional application No. 62/596,275, filed on Dec. 8, 2017, provisional application No. 62/590,249, filed on Nov. 22, 2017.

(51) Int. Cl.
*A61M 16/00* (2006.01)
*A61M 16/06* (2006.01)
(Continued)

(52) U.S. Cl.
CPC ......... *A61M 16/024* (2017.08); *A61B 5/0816* (2013.01); *A61B 5/6844* (2013.01);
(Continued)

(58) Field of Classification Search
CPC .......... A61M 16/0069; A61M 16/0672; A61M 16/161; A61M 16/0666; A61M 16/1005;
(Continued)

(56) References Cited

U.S. PATENT DOCUMENTS 6,332,463 B1    12/2001  Farrugia et al.
9,724,016 B1 *  8/2017   Al-Ali .................... A61B 7/003
(Continued)

FOREIGN PATENT DOCUMENTS

WO    WO 2015/033288 A1    3/2015
WO    WO 2015/107268 A1    7/2015
(Continued)

OTHER PUBLICATIONS

Extended Search Report in corresponding European Patent Application No. 18880341.5, dated Jul. 16, 2021, in 5 pages.
(Continued)

*Primary Examiner* — Bradley H Philips
*Assistant Examiner* — Savannah L Gabriel
(74) *Attorney, Agent, or Firm* — Knobbe, Martens, Olson & Bear, LLP

(57) ABSTRACT

Systems and methods can determine respiratory rates of a patient using a respiratory device by performing one or more frequency analyses of a signal from the gases flow. The signal from the gases flow can be one that varies with the patients breathing. The system can include a non-sealed patient interface, such as a nasal cannula in a nasal high flow therapy, or any other patient interfaces. The respiratory system can also detect whether the patient has taken off the patient interface and/or whether the patient connected to the
(Continued)

patient interface is talking or eating. Data of the patients use of the respiratory system and the patients respiratory rates can provide therapy compliance and long-term trend of use information and/or progress in the patients respiratory functions and/or other physiological functions.

17 Claims, 36 Drawing Sheets

(51) Int. Cl.
    *A61M 16/16*     (2006.01)
    *A61B 5/08*     (2006.01)
    *A61B 5/00*     (2006.01)

(52) U.S. Cl.
    CPC .... *A61M 16/0069* (2014.02); *A61M 16/0672* (2014.02); *A61M 16/161* (2014.02); *A61M 2016/003* (2013.01); *A61M 2016/0027* (2013.01); *A61M 2202/0208* (2013.01); *A61M 2205/3365* (2013.01); *A61M 2230/42* (2013.01); *A61M 2230/432* (2013.01)

(58) Field of Classification Search
    CPC ........ A61M 16/024; A61M 2205/3365; A61M 2016/0015; A61M 2016/0033
    See application file for complete search history.

(56) References Cited

U.S. PATENT DOCUMENTS

| | | | | |
|---|---|---|---|---|
| 11,318,275 | B2* | 5/2022 | Austin | A61M 16/026 |
| 2003/0066528 | A1* | 4/2003 | Hill | A61M 16/026 |
| | | | | 128/204.22 |
| 2006/0065270 | A1 | 3/2006 | Li | |
| 2007/0151563 | A1* | 7/2007 | Ozaki | A61M 16/026 |
| | | | | 128/204.23 |
| 2008/0053441 | A1* | 3/2008 | Gottlib | A61M 16/12 |
| | | | | 128/204.23 |
| 2008/0251071 | A1* | 10/2008 | Armitstead | A61M 16/0066 |
| | | | | 128/202.22 |
| 2009/0050154 | A1* | 2/2009 | Strothmann | A61M 16/161 |
| | | | | 128/204.23 |
| 2011/0259330 | A1 | 10/2011 | Jafari et al. | |
| 2013/0228181 | A1 | 9/2013 | Ahmad et al. | |
| 2014/0228692 | A1 | 8/2014 | Chan et al. | |
| 2015/0136136 | A1 | 5/2015 | Fleming et al. | |
| 2015/0144130 | A1* | 5/2015 | O'Donnell | A61M 16/0051 |
| | | | | 128/202.22 |
| 2015/0165140 | A1 | 6/2015 | Cappelli et al. | |
| 2015/0230759 | A1* | 8/2015 | Ochs | A61B 5/14551 |
| | | | | 600/476 |
| 2016/0243325 | A1 | 8/2016 | Bowman et al. | |
| 2016/0367779 | A1* | 12/2016 | Landis | A61J 7/0053 |
| 2017/0197056 | A1* | 7/2017 | Van Schalkwyk | G01P 5/245 |
| 2018/0169361 | A1* | 6/2018 | Dennis | A61M 16/107 |
| 2018/0272099 | A1* | 9/2018 | Bottom | A61M 16/1005 |

FOREIGN PATENT DOCUMENTS

| | | |
|---|---|---|
| WO | WO 2016/108121 A1 | 7/2016 |
| WO | WO 2017/027906 A1 | 2/2017 |
| WO | WO 2017/059530 A1 | 4/2017 |
| WO | WO 2017/126980 A2 | 7/2017 |
| WO | WO 2017/200394 A1 | 11/2017 |
| WO | WO 2019/102384 A1 | 5/2019 |

OTHER PUBLICATIONS

International Search Report in corresponding International Patent Application No. PCT/IB2018/059195, dated Feb. 22, 2019, in 12 pages.

Written Opinion in corresponding International Patent Application No. PCT/IB2018/059195, dated Feb. 22, 2019, in 13 pages.

International Preliminary Report on Patentability in corresponding International Patent Application No. PCT/IB2018/059195, dated May 26, 2020, in 14 pages.

* cited by examiner

RESPIRATORY RATE MONITORING FOR RESPIRATORY FLOW THERAPY SYSTEMS

FIELD OF THE DISCLOSURE

The present disclosure relates to methods and systems for monitoring the respiratory rate of a patient receiving a respiratory flow therapy. In particular, the present disclosure relates to monitoring the respiratory rate of a patient receiving a nasal high flow therapy.

BACKGROUND

Breathing assistance apparatuses are used in various environments such as hospital, medical facility, residential care, or home environments to deliver a flow of gases to users or patients. A breathing assistance or respiratory therapy apparatus (collectively, "respiratory apparatus" or "respiratory devices") may be used to deliver supplementary oxygen or other gases with a flow of gases, and/or a humidification apparatus to deliver heated and humidified gases. A respiratory apparatus may allow adjustment and control over characteristics of the gases flow, including flow rate, temperature, gases concentration, humidity, pressure, etc. Sensors, such as flow sensors and/or pressure sensors are used to measure characteristics of the gases flow.

SUMMARY

Respiratory rates of a patient using a respiratory device can be useful information. Respiratory rate data of the patient can inform clinicians about a patient's health, use of the respiratory devices and/or progress in the patient's respiratory functions. Respiratory rate data can also be used to improve the functionality of the respiratory device itself.

Inspiration and expiration by a patient using a respiratory device can affect the gases flow in the device. This is because when the patient inhales through a patient interface, such as a mask or nasal cannula, the resistance to the gases flow in the patient interface decreases; when the patient exhales, the resistance to the gases flow in the patient interface increases. In a sealed system, this inhalation and exhalation is relatively easy to measure. However, in an unsealed system, such as a nasal high flow system, patient inhalation and exhalation is much more difficult to determine because of the open nature of the system.

In a sealed respiratory system, respiratory devices can control one of the gases flow rate or pressure, leaving the other one of the gases flow rate or the pressure to exhibit observable variations as the patient breathes in and out. In these sealed systems, the start of an inspiration or expiration can serve as a triggering event for the device to alter the pressure and/or flow rate of the gases. These respiratory devices can determine a patient's respiratory rate by monitoring fluctuations in a signal, such as the flow rate or pressure, in the time domain. For example, a peak detection mechanism can determine from the signal when a breath occurs. When the signal is the flow rate, the peaks can indicate inspiration. The respiratory rate can be obtained by determining how frequent a triggering event, such as inspiration or expiration, occurs.

Fluctuations of the signal in the time domain can be hard to observe in a respiratory device employing an unsealed patient interface, such as in a nasal high flow system. The device in the unsealed respiratory system can be constantly adjusting the speed of its flow generator motor to maintain a target flow rate. Variations from the target flow rate due to the patient's breathing are often relatively small due to the blower automatically compensating its output flow rate. The unsealed or non-sealed respiratory system can also have lower impedance of the gases flow than a sealed system. The low impedance can be due to leaks from the patient's nares, which are not sealed, and/or the patient's ability to optionally breathe through his or her mouth.

In addition, the high flow rate in a nasal high flow system can result in a turbulent flow. The turbulent flow can increase noise in the signal, which can complicate the time-domain signal analysis, such as identification of the triggering events. The combination of small signal variations and increased noise in the signal of the gases flow can make it difficult to determine a breath period or frequency based on analyzing the signal in the time domain.

Determining a breath period or frequency based on analyzing the signal in the time domain can also lead to incorrectly measuring the respiratory rate by detecting a breath when there is no breath. It is easy to mistake an irregularity in a time domain signal as a respiratory triggering event.

Sealed systems can be designed to give quick readings of a respiratory rate to allow for detection of both sudden changes in and phase information of the respiratory rate to allow for breath synchronization. The quick reading design can compromise accuracy of the respiratory rate measurement.

The present disclosure discloses processes for determining respiratory rates of a patient receiving a respiratory therapy from a respiratory system by performing frequency analysis of a signal from the gases flow. The processes disclosed herein can be used when the patient interface is a non-sealed device, such as a nasal cannula in a nasal high flow therapy, or any other patient interfaces, such as a face mask, a nasal mask, a nasal pillow mask, an endotracheal tube, a tracheostomy interface, or others (such as in a Continuous Positive Airway Pressure (CPAP) therapy, and/or a Bi-level Positive Airway Pressure therapy).

The frequency analysis disclosed herein can extract magnitude and frequency information from the available data. The extracted data is less prone to errors in respiratory triggers due to irregularities in the signal. The frequency analysis can provide more reliable respiratory rate data in a wide range of respiratory devices compared to measuring a breath cycle from the time domain flow rate signal. The processes disclosed herein also focus on providing a more accurate measure of the patient's respiratory rate over a slightly longer time period than providing quick readings.

The present disclosure also discloses processes of performing time-domain and/or frequency-domain analysis of a gases flow parameter to detect connection and disconnection of the patient to the respiratory system by determining whether patient breathing can be detected from the gases flow signal. The determination of patient disconnection can be fed into other control functions of the respiratory device, and/or other patient monitoring devices, such as to interrupt an oxygen delivery control when the patient has taken off the patient interface.

The respiratory rate determination processes disclosed herein can also monitor whether the patient has taken off the patient interface and/or whether the patient connected to the patient interface is talking or eating, which can improve the accuracy in respiratory rate determination. Data of the patient's use of the respiratory system and the patient's respiratory rates can provide therapy compliance and long-term trend of use information and/or progress in the patient's respiratory functions.

A respiratory system configured to deliver a respiratory therapy to a patient and also configured to provide information related to the patient's breathing can comprise a breathing gases flow path configured to provide respiratory gases to a patient; and one or more processors, the one or more processors configured to receive a signal responsive to a gases flow parameter, the gases flow generated by a flow generator, the gases flow parameter varying with a patient's breathing, the one or more processors further configured to determine a respiratory rate of the patient based at least in part on the signal. The system can be a non-sealed system. The system can be configured to deliver a nasal high flow therapy. The system can be a sealed system. The signal can be outputted by a sensor, the one or more processors in electrical communication with the sensor. The signal can be derived from system parameters. The sensor can comprise a flow rate sensor, a pressure sensor, a motor speed sensor, and/or a carbon dioxide sensor. The sensor can be at least partially within the gases flow path. The sensor can be outside the gases flow path. The one or more processors can be configured to determine the respiratory rate of the patient based on signals responsive to two or more gases flow parameters. The one or more processors can be configured to determine the respiratory rate of the patient based on a difference between a measured gases flow parameter and an expected parameter value. The gases flow parameter can be a flow rate. The one or more processors can be configured to determine the respiratory rate of the patient based further upon a target flow rate. The one or more processors can be configured to determine the respiratory rate of the patient based further upon a measured flow resistance and a measured motor speed. The one or more processors can be configured to determine the respiratory rate of the patient based further upon a function of a measured flow resistance and a measured motor speed. The one or more processors can be configured to determine the respiratory rate of the patient based at least in part on a difference between a measured value of the flow rate and the target flow rate. The one or more processors can be configured to determine the respiratory rate of the patient based at least in part on a difference between a measured value of the flow rate and the product of a measured flow resistance and measured motor speed, or a function of the measured flow resistance and measured motor speed. The system can comprise a thermistor flow sensor or an acoustic flow rate sensor. The thermistor flow sensor can be configured to run a thermistor at a constant target temperature when the gases flow around and past the thermistor. The thermistor flow sensor can be configured to maintain first and second target temperatures. The first and second target temperatures can correspond respectively to between about 50° C. to about 70° C., and between about 90° C. to about 110° C. The first and second target temperatures can correspond respectively to about 66° C. and about 100° C. The first and second target temperatures can be associated with gases flow temperature ranges of between about 0° C. to about 60° C., and between about 20° C. to about 100° C. respectively. The first and second target temperatures can be associated with gases flow temperature ranges of between about 0° C. and about 40° C., and between about 30° C. and about 70° C. respectively. The one or more processors can be configured to change between the first and second target temperatures by connecting or bypassing a resistor within a thermistor circuit of the thermistor flow sensor. The thermistor circuit can comprise a Wheatstone bridge configuration having a first voltage divider arm and a second voltage divider arm, the thermistor located on of the first and second voltage divider arms. The gases flow parameter can be a motor speed of the flow generator. The motor speed can be measured by a motor speed sensor and/or derived from one or more parameters of the motor. The one or more processors can be configured to determine the respiratory rate of the patient based at least in part on an expected motor speed. The one or more processors can be configured to determine the respiratory rate of the patient based at least in part on a difference between the measured motor speed and an expected motor speed. The gases flow parameter can be pressure. The one or more processors can be configured to determine the respiratory rate of the patient based at least in part on an expected pressure. The one or more processors can be configured to determine the respiratory rate of the patient based at least in part on a function of a flow resistance and motor speed. The one or more processors can be configured to determine the respiratory rate of the patient based at least in part on a difference between the measured pressure and an expected pressure, or between the measured pressure and a function of a flow resistance and motor speed. The pressure can be measured by an absolute pressure sensor and/or a differential pressure sensor. The gases flow parameter can be a flow resistance. The one or more processors can be configured to determine the respiratory rate of the patient based at least in part on an expected flow resistance. The one or more processors can be configured to determine the respiratory rate of the patient based at least in part on a difference between the measured flow resistance and an expected flow resistance. The gases flow parameter can be a carbon dioxide concentration. The one or more processors can be configured to determine the respiratory rate of the patient based at least in part on the carbon dioxide concentration. The one or more processors can be configured to perform a frequency analysis to determine the respiratory rate. The frequency analysis can comprise a discrete Fourier transform. The frequency analysis can comprise a Goertzel algorithm. The one or more processors can be configured to apply an exponential decay prior to running the Goertzel algorithm. The frequency analysis can comprise a sampling rate of between about 71 Hz to about 2 Hz, or about 50 Hz to about 2.5 Hz, or about 40 Hz to about 3 Hz, or about 25 Hz to about 4 Hz, or about 20 Hz to about 5 Hz, or about 10 Hz. The respiratory rate can be a frequency having a highest magnitude as determined from the frequency analysis. The one or more processors can be configured to perform the frequency analysis on the difference between the measured parameter and the expected parameter value to determine the respiratory rate. The one or more processors can be further configured to apply a first lookback function to a difference between the measured parameter and an expected parameter value to obtain a second signal; determine a second respiratory rate from the second signal; and output a final respiratory rate as an average of the determined respiratory rate and the second determined respiratory rate. The one or more processors can be further configured to apply a second lookback function to the difference between the measured parameter and the expected parameter value to obtain a third signal; determine a third respiratory rate from the third signal; and output a final respiratory rate as an average of the determined respiratory rate, the second determined respiratory rate, and the third determined respiratory rate. The first or second lookback function can have a lookback period determined based at least in part on the determined respiratory rate. The second and/or third respiratory rates can be determined by a frequency analysis. The one or more processors can be further configured to calculate one or more cutoff values based at least in part on results of the frequency analyses of the difference between the measured parameter and the expected parameter value, the second signal, and the third signal. The one or more cutoff values can comprise divergence, magnitude, and/or percentile cutoff values. The one or more processors can be configured to calculate a signal quality confidence value based on the one or more cutoff values. The one or more processors can be further configured to apply a lookback function to a difference between the measured parameter and an expected parameter value to obtain a lookback signal, and compare the difference between the measured parameter and the expected parameter value with the lookback signal to determine a correlation coefficient, the correlation coefficient contributing to a determination of whether the patient is connected to the system. The lookback function can comprise a lookback period of half of a breath period corresponding to the determined respiratory rate. The one or more processors can be configured to calculate a breath weighting coefficient based on the correlation coefficient and determine whether the patient is connected to the system based on the breath weighting coefficient. The one or more processors can be further configured to analyze the difference between the measured parameter and the expected parameter value to perform a boundary count, wherein the boundary count can comprise counting instances when a magnitude of the difference exceeds a boundary value, wherein the magnitude of the difference exceeding the boundary value can be a factor indicating that the patient is connected to the system. The boundary value can be below a parameter variation caused by a patient's breathing. The boundary value can be above a maximum parameter variation when a patient is not connected to the system. The boundary value can be variable between a maximum and minimum value. The one or more processors can be further configured to combine the breath weighting coefficient and the boundary count to obtain a weighted value, the weighted value being added to a running total. The one or more processors can be configured to require a predetermined amount of time for the running total to exceed a threshold indicating that the patient is connected to the system. The one or more processors can be configured to decay the running total in a control loop so as to require the patient to be regularly breathing in order for the running total to remain above the threshold. The predetermined amount of time can be about 5 seconds to about 60 seconds, or about 40 seconds, or about 20 seconds. The one or more processors can output data of whether the patient is connected to the system, and/or the patient's respiratory rate for storing in an electronic memory. The one or more processors can be configured to output the final respiratory rate for display if the signal quality confidence value exceeds a predetermined threshold. If the signal quality confidence value does not exceed the predetermined threshold, the one or more processors can be configured to output a message indicative of an indeterminate respiratory rate value for display. The one or more processors can be configured to compare the signal quality confidence value with the predetermined threshold only if the one or more processors detect that the patient is connected to the system. The one or more processors can be configured to determine whether the patient is connected to the system by analyzing the difference between the measured parameter and the expected parameter value in the time domain, in the frequency domain, or both. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The one or more processors can be configured to determine whether the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A respiratory system configured to deliver a respiratory therapy to a patient and also configured to provide information related to the patient's breathing can comprise a breathing gases flow path configured to provide respiratory gases to a patient; and one or more processors, the one or more processors configured to receive a signal responsive to a gases flow parameter, the gases flow generated by a flow generator, the gases flow parameter varying with a patient's breathing, the one or more processors further configured to determine if the patient is connected to the system based at least in part on the signal from the sensor. The system can be a non-sealed system. The system can be configured to deliver a nasal high flow therapy. The system can be a sealed system. The signal can be outputted by a sensor, the one or more processors in electrical communication with the sensor. The signal can be derived from system parameters. The sensor can comprise a flow rate sensor, a pressure sensor, a motor speed sensor, and/or a carbon dioxide sensor. The sensor can be at least partially within the gases flow path. The sensor can be outside the gases flow path. The one or more processors can be configured to determine the respiratory rate of the patient based on signals responsive to two or more gases flow parameters. The one or more processors can be configured to determine whether the patient is connected to the system based on a difference between a measured gases flow parameter based on the signal from the sensor and an expected parameter value. The gases flow parameter can be a flow rate, pressure, flow resistance, motor speed of the flow generator, and/or carbon dioxide concentration. The flow rate can be measured by a thermistor flow sensor or an acoustic flow rate sensor. The flow rate can be measured by a thermistor flow sensor configured to run the thermistor at a constant target temperature when the gases flow around and past the thermistor. The thermistor flow sensor can be configured to maintain first and second target temperatures. The one or more processors can be configured to determine whether the patient is connected to the system based on a difference between a measured flow rate and a target flow rate. The one or more processors can be configured to determine whether the patient is connected to the system based on a difference between a measured flow rate and the product of a measured flow resistance and measured motor speed, or a difference between the measured flow rate and a function of the measured flow resistance and measured motor speed. The motor speed can be measured by the motor speed sensor and/or derived from one or more parameters of the flow generator motor. The one or more processors can be configured to determine whether the patient is connected to the system based on a difference between a measured motor speed and an expected motor speed. The pressure can be measured by an absolute pressure sensor and/or a differential pressure sensor. The one or more processors can be configured to determine whether the patient is connected to the system based on a difference between a measured pressure and an expected pressure, or a difference between the measured pressure and a function of a flow resistance and motor speed. The flow resistance can be determined at least based on the measured flow rate and the measure pressure, or on the measured flow rate and the measured motor speed. The one or more processors can be configured to determine whether the patient is connected to the system based on a difference between a measured flow resistance and an expected flow resistance. The one or more processors can be configured to determine whether the patient is connected to the system based on a time-domain analysis and/or a frequency analysis of the difference between the measured gases flow parameter and the expected parameter value. The one or more processors can be configured to analyze the difference between the measured parameter and the expected parameter value to perform a boundary count, wherein the boundary count can comprise counting instances when a magnitude of the difference exceeds a boundary value, wherein the magnitude of the difference exceeding the boundary value can be a factor indicating that the patient is connected to the system. The boundary value can be below a parameter variation caused by a patient's breathing. The boundary value can be above a maximum parameter variation when a patient is not connected to the system. The boundary value can be variable between a maximum and minimum value. The one or more processors can be configured to determine the patient's respiratory rate based at least in part on the difference between the measured parameter and the expected parameter value, apply a lookback function to the difference between the measured parameter and the expected parameter value to obtain a lookback signal, wherein the lookback function can comprise a lookback period of half of a breath period corresponding to the determined respiratory rate, and compare the difference between the measured parameter and the expected parameter value with the lookback signal to determine a correlation coefficient, the correlation coefficient contributing to a determination of whether the patient is connected to the system. The respiratory rate can be determined by a frequency analysis. The frequency analysis can comprise a discrete Fourier transform. The frequency analysis can comprise a Goertzel algorithm. The one or more processors can be configured to apply an exponential decay prior to running the Goertzel algorithm. The frequency analysis can comprise a sampling rate of between about 71 Hz to about 2 Hz, or about 50 Hz to about 2.5 Hz, or about 40 Hz to about 3 Hz, or about 25 Hz to about 4 Hz, or about 20 Hz to about 5 Hz, or about 10 Hz. The respiratory rate can be a frequency having a highest magnitude as determined from the frequency analysis. The one or more processors can be configured to calculate a breath weighting coefficient based on the correlation coefficient and determine whether the patient is connected to the system based on the breath weighting coefficient. The one or more processors can be further configured to combine the breath weighting coefficient and the boundary count to obtain a weighted value, the weighted value being added to a running total. The one or more processors can be configured to require a predetermined amount of time for the running total to exceed a threshold indicating that the patient is connected to the system. The one or more processors can be configured to decay the running total in a control loop so as to require the patient to be regularly breathing in order for the running total to remain above the threshold. The predetermined amount of time can be about 5 seconds to about 60 seconds, or about 40 seconds, or about 20 seconds. The one or more processors can output data of whether the patient is connected to the system for storing in an electronic memory. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A method of analyzing a signal from a gases flow of a respiratory system configured to delivery respiratory therapy to a patient via a patient interface can comprise receiving a signal indicative of a gases flow parameter from a sensor, the gases flow generated by a flow generator of the respiratory device, the gases flow parameter varying with the patient's breathing; processing the signal to calculate a value of the parameter; generating a variation signal responsive to a difference between the calculated parameter value and an expected parameter value; and determine the patient's respiratory rate and/or whether the patient is connected to the system based at least in part on the variation signal. Determining can be by a frequency analysis on the variation signal. The respiratory rate can be a frequency having a highest magnitude as determined from the frequency analysis. The frequency analysis can comprise running a Goertzel algorithm on the variation signal. The frequency analysis can further comprise applying an exponential decay to the variation signal before running the Goertzel algorithm. Determining the patient's respiratory rate can further comprise subtracting from the variation signal a previous variation signal of one or more predetermined lookback periods to obtain one or more additional signal, running the Goertzel algorithm on the one or more additional signals to obtain one or more additional respiratory rate values, and calculating a final respiratory rate based on the determined respiratory rate and the one or more additional respiratory rate values. Determining whether the patient is connected to the system can further comprise subtracting from the variation signal a previous variation signal of a predetermined lookback period to obtain a second signal, comparing the variation signal with the second signal to determine a correlation coefficient, the correlation coefficient contributing to a determination of whether the patient is connected to the system. Determining whether the patient is connected to the system can further comprise calculating a breath weighting coefficient based on the correlation coefficient and determining whether the patient is connected to the system based on the breath weighting coefficient. Determining whether the patient is connected to the system can further comprise performing a boundary count on the variation signal, the boundary count comprising counting instances when a magnitude of the variation signal exceeds a boundary value, wherein the magnitude exceeding the boundary value can be a factor indicating that the patient is connected to the system. Determining whether the patient is connected to the system can further comprise combining the breath weighting coefficient and a boundary count to obtain a weighted value, the weighted value being added to a running total. Determining whether the patient is connected to the system can further comprise requiring a predetermined amount of time for the running total to exceed a threshold indicating that the patient is connected to the system. Determining whether the patient is connected to the system can further comprise decaying the running total in a control loop so as to require the patient to be regularly breathing in order for the running total to remain above the threshold. The method further comprises determining whether the patient has removed the patient interface or disconnected from the system based at least in part on the signal. The method further comprises recording compliance data based at least in part on determination of whether the patient is connected to the system. The method further comprises activating or deactivating a motor speed control in the respiratory device based at least in part on determination of whether the patient is connected to the system. The method further comprises activating or deactivating an oxygen supply control in the respiratory device based at least in part on determination of whether the patient is connected to the system.

A method of applying a lookback function on a signal related to a gases flow of a respiratory system configured to delivery respiratory therapy to a patient via a patient interface can comprise receiving a signal indicative of a gases flow parameter from a sensor, the gases flow generated by a flow generator of the respiratory device, the gases flow parameter varying with the patient's breathing; processing the signal to calculate a value of the parameter; and obtaining a lookback signal based on the signal and a previous signal of a predetermined lookback period. The method can further comprise determining the patient's respiratory rate and/or whether the patient is connected to the system based at least in part on the signal and the lookback signal. The method can further comprise generating a variation signal responsive to a difference between the calculated parameter value and an expected parameter value, wherein obtaining is by subtracting from the variation signal a previous variation signal of the predetermined lookback period. The lookback period can be a constant value. The lookback period can be determined from a respiratory rate of the patient. The lookback period can be a half or full breath period of the respiratory rate. The respiratory rate can be determined at least in part based on the gases flow parameter, or a difference between the gases flow parameter measured by the sensor and an expected parameter value. The respiratory rate can be determined by a frequency analysis of the signal or the variation signal. The respiratory rate can be a frequency having a highest magnitude as determined from the frequency analysis. The frequency analysis can comprise a Goertzel algorithm. The frequency analysis can further comprise apply an exponential decay to the signal or the variation signal before running the Goertzel algorithm Determining the patient's respiratory rate can further comprise determining an additional respiratory rate from the lookback signal, and calculating a final respiratory rate based on the determined respiratory rate and the additional respiratory rate. Determining whether the patient is connected to the system can further comprise performing a boundary count on the variation signal, the boundary count comprising counting instances when a magnitude of the variation signal exceeds a boundary value, wherein the magnitude exceeding the boundary value is a factor indicating that the patient is connected to the system. Determining whether the patient is connected to the system can further comprise comparing the variation signal with the lookback signal to determine a correlation coefficient, the correlation coefficient contributing to a determination of whether the patient is connected to the system. Determining whether the patient is connected to the system can further comprise calculating a breath weighting coefficient based on the correlation coefficient and determining whether the patient is connected to the system based on the breath weighting coefficient. Determining whether the patient is connected to the system can further comprise combining the breath weighting coefficient and a boundary count to obtain a weighted value, the weighted value being added to a running total. Determining whether the patient is connected to the system can further comprise decaying the running total in a control loop so as to require a predetermined amount of time for receiving the number of data points needed for the running total to reach a threshold indicating that the patient is breathing using the system. Obtaining a lookback signal can comprise subtracting from the signal a previous signal of a predetermined lookback period. Obtaining a lookback signal can comprise adding the signal and the previous signal. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system. The first and second target temperatures can correspond respectively to between about 50° C. to about 70° C., and between about 90° C. to about 110° C. The first and second target temperatures can correspond respectively to about 66° C. and about 100° C. The first and second target temperatures can be associated with gases flow temperature ranges of between about 0° C. to about 60° C., and between about 20° C. to about 100° C. respectively. The first and second target temperatures can be associated with gases flow temperature ranges of between about 0° C. and about 40° C., and between about 30° C. and about 70° C. respectively. The one or more processors can be configured to change between the first and second target temperatures by connecting or bypassing a resistor within a thermistor circuit of the thermistor flow sensor. The thermistor circuit can comprise a Wheatstone bridge configuration having a first voltage divider arm and a second voltage divider arm, the thermistor located on of the first and second voltage divider arms. The method further comprises determining whether the patient has removed the patient interface or disconnected from the system based at least in part on the signal. The method further comprises recording compliance data based at least in part on determination of whether the patient is connected to the system. The method further comprises activating or deactivating a motor speed control in the respiratory device based at least in part on determination of whether the patient is connected to the system. The method further comprises activating or deactivating an oxygen supply control in the respiratory device based at least in part on determination of whether the patient is connected to the system.

A respiratory system configured to deliver a respiratory therapy to a patient and also configured to provide information related to the patient's breathing can comprise a sensor placed at least partially within a path of a gases flow generated by a flow generator and configured to output a signal responsive to a gases flow parameter, the gases flow parameter varying with a patient's breathing; and one or more processors in electrical communication with the sensor and configured to determine a respiratory rate of the patient based at least in part on the signal output from the sensor. The system can be a non-sealed system. The system can be configured to deliver a nasal high flow therapy. The system can be a sealed system. The sensor can comprise a flow rate sensor, a pressure sensor, and/or a carbon dioxide sensor. The one or more processors can be further configured to perform a frequency analysis of the signal output from the sensor to determine the respiratory rate of the patient. The one or more processors can be configured to determine the respiratory rate of the patient based on a derived signal of the signal output. The derived signal can be a difference between a measured value of the gases flow parameter and an expected value. The gases flow parameter can be a flow rate. The derived signal can be a difference between a measured value of the flow rate and the target flow rate. The derived signal can be a difference between a measured value of the flow rate and the product of a flow resistance and motor speed measured by the motor sensor, or a function of the flow resistance and motor speed. The one or more processors can be configured to receive a signal indicative of motor speed of a flow generator from a motor speed sensor and determine the respiratory rate of the patient based at least in part on the signal indicative of the motor speed. The system can comprise a motor speed sensor. The one or more processors can be configured to determine the respiratory rate of the patient based at least in part on an expected motor speed. The gases flow parameter can be pressure. The one or more processors can be configured to determine the respiratory rate of the patient based at least in part on an expected pressure. The one or more processors can be configured to determine the respiratory rate of the patient based at least in part on a function of a flow resistance and motor speed. The gases flow parameter can be a flow resistance. The flow resistance can be calculated from the flow rate and one of the pressure or motor speed. The one or more processors can be configured to determine the respiratory rate of the patient based at least in part on an expected flow resistance. The gases flow parameter can be a carbon dioxide concentration. The one or more processors can be configured to determine the respiratory rate of the patient based at least in part on the carbon dioxide concentration. The flow rate sensor can be a thermistor flow sensor. The pressure sensor can comprise an absolute pressure sensor and/or a differential pressure sensor. The one or more processors can be configured to perform a frequency analysis of the derived signal to determine the respiratory rate. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A respiratory system configured to deliver a respiratory therapy to a patient and also configured to provide information related to the patient's breathing can comprise a sensor placed at least partially within a path of a gases flow generated by a flow generator and configured to output a signal responsive to a gases flow parameter, the gases flow parameter varying with a patient's breathing; and one or more processors in electrical communication with the sensor and configured to measure the gases flow parameter based at least in part on the signal output from the sensor, the one or more processors further configured to perform a frequency analysis of the signal output from the sensor to determine a respiratory rate of the patient. The system can be a non-sealed system. The system can be configured to deliver a nasal high flow therapy. The system can be a sealed system. The respiratory rate can be a frequency having a highest magnitude as determined from the frequency analysis. The system can further comprise a second sensor placed at least partially within the gases flow path and configured to output a second signal responsive to a second gases flow parameter, the second gases flow parameter varying with a patient's breathing, wherein the one or more processors are in electrical communication with the sensor and configured to measure the second gases flow parameter based at least in part on the second signal output from the second sensor, the one or more processors further configured to perform a frequency analysis of the second signal output from the second sensor, and wherein the respiratory rate of the patient is determined from a combination of magnitudes of each frequency determined by the frequency analysis of the first and second signal outputs. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A respiratory system configured to deliver a respiratory therapy to a patient and also configured to provide information related to the patient's breathing can comprise a flow rate sensor placed at least partially within a path of a gases flow generated by a flow generator and configured to output a signal responsive to a gases flow rate; and one or more processors in electrical communication with the sensor and configured to measure the gases flow rate based at least in part on the signal output from the flow rate sensor, the one or more processors further configured to perform a frequency analysis of a flow rate variation signal to determine a respiratory rate of the patient, the flow rate variation signal derived at least in part from the measured gases flow rate. The system can be a non-sealed system. The system can be configured to deliver a nasal high flow therapy. The system can be a sealed system. The flow rate variation signal can be the difference between the measured flow rate and a target flow rate configured to be maintained by the one or more processors varying a motor speed of a flow generator. The flow variation signal can be the difference between the measured flow rate and a product of a flow resistance and a motor speed of a flow generator. The flow resistance can be determined based at least in part on the measured gases flow rate and the motor speed. The respiratory rate can be a frequency having a highest magnitude as determined from the frequency analysis. The one or more processors can be further configured to apply a first lookback function to the flow rate variation signal to obtain a second signal; perform a frequency analysis of the second signal to determine a second respiratory rate; and output a final respiratory rate as an average of the determined respiratory rate and the second determined respiratory rate. The one or more processors can be further configured to apply a second lookback function to the flow rate variation signal to obtain a third signal; perform a frequency analysis of the third signal to determine a third respiratory rate; and output a final respiratory rate as an average of the determined respiratory rate, the second determined respiratory rate, and the third determined respiratory rate. The first or second lookback function can have a lookback period determined based at least in part on the determined respiratory rate. The one or more processors can be further configured to calculate one or more cutoff values based at least in part on results of the frequency analyses of the flow rate variation signal, the second signal, and the third signal. The one or more cutoff values can comprise divergence, magnitude, and/or percentile cutoff values. The one or more processors can be configured to calculate a signal quality confidence value based on the one or more cutoff values. The one or more processors are further configured to apply a lookback function to the flow rate variation signal to obtain a lookback signal, and compare the flow rate variation signal and the lookback signal to determine a correlation coefficient, the correlation coefficient contributing to a determination of whether the patient is connected to the system. The lookback function can comprise a lookback period of half of a breath period corresponding to the determined respiratory rate. The one or more processors can be configured to calculate a breath weighting coefficient based on the correlation coefficient and determine whether the patient is connected to the system based on the breath weighting coefficient. The one or more processors can be further configured to analyze the flow rate variation signal to perform a boundary count, wherein the boundary count can comprise counting instances when the measured flow rate exceeds a boundary flow rate value, wherein the measured flow rate exceeding a boundary flow rate value can be an indication that the patient is connected to the system. The boundary flow rate value can be below a flow variation caused by a patient's breathing. The boundary flow rate value can be above a maximum flow variation when a patient is not connected to the system. The boundary flow rate value can be variable between a maximum and minimum value. The one or more processors can be further configured to combine the correlation coefficient and the boundary count to obtain a weighted value, the weighted value being added to a running total. The one or more processors can be configured to decay the running total in a control loop so as to require the patient to breathing using the system for a predetermined amount of time before the running total reaches a threshold indicating that the patient is breathing using the system. The predetermined amount of time can be about 5 seconds to about 60 seconds, or about 40 seconds, or about 20 seconds. The one or more processors can output data of whether the patient is connected to the system and/or the patient's respiratory rate data for storing in an electronic memory. The one or more processors can be configured to output the final respiratory rate for display if the signal quality confidence value exceeds a predetermined threshold. If the signal quality confidence value does not exceed a predetermined threshold, the one or more processors can be configured to output a message indicative of an indeterminate respiratory rate value for display. The one or more processors can be configured to compare the final respiratory rate value with the signal quality confidence value only if the one or more processors detect that the patient is connected to the system. The one or more processors can be configured to determine whether the patient is connected to the system by analyzing the flow rate variation signal in the time domain, in the frequency domain, or both. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A respiratory system configured to deliver a respiratory therapy to a patient and also configured to detect if the patient is connected to the system can comprise a flow rate sensor placed at least partially within a path of a gases flow generated by a flow generator and configured to output a signal responsive to a gases flow rate; and one or more processors in electrical communication with the sensor and configured to measure the gases flow rate based at least in part on the signal output from the flow rate sensor, and derive a flow rate variation signal at least in part from the measured gases flow rate, wherein the one or more processors are further configured to analyze the flow rate variation signal to perform a boundary count and determine if the patient is connected to the system based at least in part on the boundary count, wherein the boundary count comprises counting instances when the measured flow rate exceeds a boundary flow rate value. The system can be a non-sealed system. The system can be configured to deliver a nasal high flow therapy. The system can be a sealed system. The sensor can comprise a flow rate sensor, a pressure sensor, and/or a carbon dioxide sensor. The flow rate variation signal can be a difference between the measured flow rate and a target flow rate configured to be maintained by the one or more processors varying a motor speed of a flow generator. The flow variation signal can be a difference between the measured flow rate and a product of a flow resistance and a motor speed of a flow generator. The flow resistance can be determined based at least in part on the measured gases flow rate and the motor speed. The boundary flow rate value is below a flow variation caused by a patient's breathing. The boundary flow rate value is above a maximum flow variation when a patient is not connected to the system. The boundary flow rate value can be variable between a maximum and minimum value. The one or more processors can output for storing in an electronic memory data of whether the patient is connected to the system. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The one or more processors can be configured to determine whether the patient has removed the patient interface or disconnected from the system based at least in part on the signal. The one or more processors can be configured to record compliance data based at least in part on determination of whether the patient is connected to the system. The one or more processors can be configured to activate or deactivate a motor speed control in the respiratory device based at least in part on determination of whether the patient is connected to the system. The one or more processors can be configured to activate or deactivate an oxygen supply control in the respiratory device based at least in part on determination of whether the patient is connected to the system.

A method of determining a respiratory rate of a patient receiving a respiratory therapy from a respiratory system and/or patient disconnection from the system can comprise receiving, from a sensor placed at least partially within a path of a gases flow generated by a flow generator, a signal responsive to a gases flow parameter, the gases flow parameter varying with a patient's breathing; processing the signal to measure the gases flow parameter; and performing a frequency analysis of the signal output from the sensor to determine a respiratory rate of the patient. The system can be a non-sealed system. The system can be configured to deliver a nasal high flow therapy. The system can be a sealed system. The respiratory rate can be a frequency having a highest magnitude as determined from the frequency analysis. The method can further comprise receiving, from a second sensor placed at least partially within the path of the gases flow, a second signal responsive to a second gases flow parameter, the second gases flow parameter varying with a patient's breathing; processing the second signal to measure the second gases flow parameter; performing a frequency analysis of the second signal output from the second sensor; and combining magnitudes of each frequency determined by the frequency analysis of the first and second signals to determine the respiratory rate of the patient. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The method further comprises determining whether the patient has removed the patient interface or disconnected from the system based at least in part on the signal. The method further comprises recording compliance data based at least in part on determination of whether the patient is connected to the system. The method further comprises activating or deactivating a motor speed control in the respiratory device based at least in part on determination of whether the patient is connected to the system. The method further comprises activating or deactivating an oxygen supply control in the respiratory device based at least in part on determination of whether the patient is connected to the system.

A method of determining a respiratory rate of a patient receiving a respiratory therapy from a respiratory system and/or patient disconnection and/or connection from the system can comprise receiving, from a flow rate sensor placed at least partially within a path of a gases flow generated by a flow generator, a signal responsive to a gases flow rate; and processing the signal output from the flow rate sensor to measure the gases flow rate; deriving a flow rate variation signal at least in part from the measured gases flow rate; and performing a frequency analysis of the flow rate variation signal to determine a respiratory rate of the patient. The system can be a non-sealed system. The system can be configured to deliver a nasal high flow therapy. The system can be a sealed system. The flow rate variation signal can be the difference between the measured flow rate and a target flow rate configured to be maintained by the one or more processors varying a motor speed of a flow generator. The flow variation signal can be the difference between the measured flow rate and a product of a flow resistance and a motor speed of a flow generator. The flow resistance can be determined based at least in part on the measured gases flow rate and the motor speed. The respiratory rate can be a frequency having a highest magnitude as determined from the frequency analysis. The method can further comprise applying a first lookback function to the flow rate variation signal to obtain a second signal; performing a frequency analysis of the second signal to determine a second respiratory rate; and outputting a final respiratory rate as an average of the determined respiratory rate and the second determined respiratory rate. The method can further comprise applying a second lookback function to the flow rate variation signal to obtain a third signal; performing a frequency analysis of the third signal to determine a third respiratory rate; and outputting a final respiratory rate as an average of the determined respiratory rate, the second determined respiratory rate, and the third determined respiratory rate. The first or second lookback function can have a lookback period determined based at least in part on the determined respiratory rate. The method can further comprise calculating one or more cutoff values based at least in part on results of the frequency analyses of the flow rate variation signal, the second signal, and the third signal. The one or more cutoff values can comprise divergence, magnitude, and/or percentile cutoff values. The method can further comprise calculating a signal quality confidence value based on the one or more cutoff values. The method can further comprise applying a lookback function to the flow rate variation signal to obtain a lookback signal, and comparing the flow rate variation signal and the lookback signal to determine a correlation coefficient, the correlation coefficient contributing to a determination of whether the patient is connected to the system. The lookback function can comprise a lookback period of half of a breath period corresponding to the determined respiratory rate. The method can further comprise calculating a breath weighting coefficient based on the correlation coefficient and determining whether the patient is connected to the system based on the breath weighting coefficient. The method can further comprise analyzing the flow rate variation signal to perform a boundary count, wherein the boundary count can comprise counting instances when the measured flow rate exceeds a boundary flow rate value, wherein the measured flow rate exceeding a boundary flow rate value can be an indication that the patient is connected to the system. The boundary flow rate value can be below a flow variation caused by a patient's breathing. The boundary flow rate value can be above a maximum flow variation when a patient is not connected to the system. The boundary flow rate value can be variable between a maximum and minimum value. The method can further comprise combining the correlation coefficient and the boundary count to obtain a weighted value, the weighted value being added to a running total. The method can further comprise decaying the running total in a control loop so as to require the patient to breathing using the system for a predetermined amount of time before the running total reaches a threshold indicating that the patient is breathing using the system. The predetermined amount of time can be about 5 seconds to about 60 seconds, or about 40 seconds, or about 20 seconds. The method can further comprise outputting data of whether the patient is connected to the system and/or the patient's respiratory rate data for storing in an electronic memory. The method can further comprise outputting the final respiratory rate for display if the signal quality confidence value exceeds a predetermined threshold. If the signal quality confidence value does not exceed a predetermined threshold, the method can further comprise outputting a message indicative of an indeterminate respiratory rate value for display. The method can further comprise comparing the final respiratory rate value with the signal quality confidence value only if the one or more processors detect that the patient is connected to the system. The method can further comprise determining whether the patient is connected to the system by analyzing the flow rate variation signal in the time domain, in the frequency domain, or both. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The one or more processors can be configured to apply an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The method further comprises determining whether the patient has removed the patient interface or disconnected from the system based at least in part on the signal. The method further comprises recording compliance data based at least in part on determination of whether the patient is connected to the system. The method further comprises activating or deactivating a motor speed control in the respiratory device based at least in part on determination of whether the patient is connected to the system. The method further comprises activating or deactivating an oxygen supply control in the respiratory device based at least in part on determination of whether the patient is connected to the system.

A method of determining whether a patient is connected to a respiratory system can comprise receiving, from a flow rate sensor placed at least partially within a path of a gases flow generated by a flow generator, a signal responsive to a gases flow rate; processing the signal output from the flow rate sensor to measure the gases flow rate; deriving a flow rate variation signal at least in part from the measured gases flow rate; analyzing the flow rate variation signal to perform a boundary count, wherein the boundary count comprises counting instances when the measured flow rate exceeds a boundary flow rate value; and determining if the patient is connected to the system based at least in part on the boundary count. The system can be a non-sealed system. The system can be configured to deliver a nasal high flow therapy. The system can be a sealed system. The sensor can comprise a flow rate sensor, a pressure sensor, and/or a carbon dioxide sensor. The flow rate variation signal can be a difference between the measured flow rate and a target flow rate configured to be maintained by the one or more processors varying a motor speed of a flow generator. The flow variation signal can be a difference between the measured flow rate and a product of a flow resistance and a motor speed of a flow generator. The flow resistance can be determined based at least in part on the measured gases flow rate and the motor speed. The boundary flow rate value is below a flow variation caused by a patient's breathing. The boundary flow rate value is above a maximum flow variation when a patient is not connected to the system. The boundary flow rate value can be variable between a maximum and minimum value. The method can further comprise outputting data of whether the patient is connected to the system for storing in an electronic memory. The system can further comprise the flow generator and a patient interface in fluid communication with the flow generator, wherein the sensor is located within a respiratory device housing near the flow generator or within the patient interface. The frequency analysis can comprise a discrete Fourier transform. The frequency analysis can comprise a Goertzel algorithm. The method can further comprise applying an exponential decay to the signal output prior to running the Goertzel algorithm. The frequency analysis can comprise a sampling rate of between about 71 Hz to about 2 Hz, or between about 50 Hz to about 2.5 Hz, or between about 40 Hz to about 3 Hz, or between about 25 Hz to about 4 Hz, or between about 20 Hz to about 5 Hz, or about 10 Hz. The flow rate sensor can comprise an acoustic sensor or a thermistor flow sensor. The thermistor flow sensor can be configured to run the thermistor at a constant target temperature when the gases flow around and past the thermistor. The thermistor flow sensor can be configured to maintain a plurality of target temperatures on a thermistor when the gases flow around and past the thermistor. The thermistor flow sensor can be configured to maintain first and second target temperatures. The system can comprise a patient interface, the patient interface being a nasal cannula, a face mask, a nasal mask, an endotracheal tube, or a tracheostomy interface. The system can comprise a humidifier configured to humidify the gases flow to the patient. The system can comprise a display configured to receive from the one or more processors and display information related to the patient's respiratory rate. The method further comprises determining whether the patient has removed the patient interface or disconnected from the system based at least in part on the signal. The method further comprises recording compliance data based at least in part on determination of whether the patient is connected to the system. The method further comprises activating or deactivating a motor speed control in the respiratory device based at least in part on determination of whether the patient is connected to the system. The method further comprises activating or deactivating an oxygen supply control in the respiratory device based at least in part on determination of whether the patient is connected to the system.

In some configurations, a respiratory system configured to deliver a respiratory therapy to a patient and also configured to provide information related to the patient can comprise a respiratory device comprising a controller, wherein the controller can be configured to: receive measurements of a first parameter of a flow of gases or representative of performance of a component of the device, the first parameter indicative of the patient's respiration; receive measurements of a second parameter of a gases flow or representative of performance of a component of the device, wherein the second parameter can have an assumed effect on the first parameter; determine whether the assumed effect is valid; and discard the first parameter from a validated first parameter dataset in response to the assumed effect being invalid, the controller also configured to use the validated first parameter dataset to make an estimate about the patient.

In some configurations, the estimate can include an estimate of the patient's respiratory rate. In some configurations, the estimate can include an estimate of whether the patient is wearing a patient interface of the system.

In some configurations, the first parameter can be flow rate.

In some configurations, the device can further comprise a blower including a motor and the second parameter can be motor speed.

In some configurations, the assumed effect can be invalid if the motor speed is below a first threshold. In some configurations, the assumed effect can be invalid if recent changes in the motor speed are above a second threshold.

In some configurations, the second parameter can be pressure.

In some configurations, the first parameter can be flow rate, pressure, motor speed, power to motor, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the controller can be configured to measure a composition of the flow of gases after the ambient air and the supplementary gas have been mixed.

In some configurations, the assumed effect can be invalid if recent changes in the composition of the flow of gases are above a third threshold.

In some configurations, the controller can be configured to measure a flow rate of the supplementary gas into the device.

In some configurations, the assumed effect can be invalid if recent changes in the flow rate of the supplementary gas are above a third threshold.

In some configurations, the controller can be configured to control the flow rate of the supplementary gas into the device.

In some configurations, if the assumed effect is valid, the controller can be configured to make the estimate about the patient using the assumed effect.

In some configurations, the controller can be configured to subtract the assumed effect from the first parameter to output a modified first parameter and make the estimate based on the modified first parameter.

In some configurations, the controller can be configured to perform a frequency analysis of the validated first parameter dataset to make the estimate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient, can comprise using a controller of a respiratory device, receiving measurements of a first parameter of a flow of gases or representative of performance of a component of the device, the first parameter indicative of the patient's respiration; receiving measurements of a second parameter of a gases flow or representative of performance of a component of the device, wherein the second parameter can have an assumed effect on the first parameter; determining whether the assumed effect is valid; and discarding the first parameter from a validated first parameter dataset in response to the assumed effect being invalid, the controller also configured to use the validated first parameter dataset to make an estimate about the patient.

In some configurations, the estimate can include an estimate of the patient's respiratory rate. In some configurations, the estimate can include an estimate of whether the patient is wearing a patient interface of the system.

In some configurations, the first parameter can be flow rate.

In some configurations, the device can further comprise a blower including a motor and the second parameter can be motor speed.

In some configurations, the assumed effect can be invalid if the motor speed is below a first threshold. In some configurations, the assumed effect can be invalid if recent changes in the motor speed are above a second threshold.

In some configurations, the second parameter can be pressure.

In some configurations, the first parameter can be flow rate, pressure, motor speed, power to motor, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the method can further comprise measuring a composition of the flow of gases after the ambient air and the supplementary gas have been mixed.

In some configurations, the assumed effect can be invalid if recent changes in the composition of the flow of gases are above a third threshold.

In some configurations, the method can further comprise measuring a flow rate of the supplementary gas into the device.

In some configurations, the assumed effect can be invalid if recent changes in the flow rate of the supplementary gas are above a third threshold.

In some configurations, the method can further comprise controlling the flow rate of the supplementary gas into the device.

In some configurations, if the assumed effect is valid, the method can further comprise making the estimate about the patient using the assumed effect.

In some configurations, the method can further comprise subtracting the assumed effect from the first parameter to output a modified first parameter and making the estimate based on the modified first parameter.

In some configurations, the method can further comprise performing a frequency analysis of the validated first parameter dataset to make the estimate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a respiratory system configured to deliver a respiratory therapy to a patient and also configured to provide information related to the patient can comprise a respiratory device comprising a controller, wherein the controller can be configured to: receive measurements of a first parameter of a gases flow or representative of performance of a component of the device, the first parameter indicative of the patient's respiration; receive measurements of a second parameter of a gases flow or representative of performance of a component of the device; determine an assumed effect of the second parameter on the first parameter; and make an estimate about the patient using the assumed effect from the first parameter to output a modified first parameter.

In some configurations, the controller can be configured to subtract the assumed effect from the first parameter to output a modified first parameter and make the estimate based on the modified first parameter.

In some configurations, the estimate can include an estimate of the patient's respiratory rate. In some configurations, the estimate can include an estimate of whether the patient is wearing a patient interface of the system.

In some configurations, the first parameter can be flow rate.

In some configurations, the device can further comprise a blower including a motor and the second parameter can be motor speed.

In some configurations, the controller can be configured to determine whether the assumed effect is valid and the assumed effect is invalid if the motor speed is below a first threshold.

In some configurations, the controller can be configured to determine whether the assumed effect is valid and the assumed effect can be invalid if recent changes in the motor speed are above a second threshold.

In some configurations, the second parameter can be pressure.

In some configurations, the first parameter can be flow rate, pressure, motor speed, power to motor, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the controller can be configured to measure a composition of the flow of gases after the ambient air and the supplementary gas have been mixed.

In some configurations, the controller can be configured to determine whether the assumed effect is valid and the assumed effect can be invalid if recent changes in the composition of the flow of gases are above a third threshold.

In some configurations, the controller can be configured to measure a flow rate of the supplementary gas into the device.

In some configurations, the controller can be configured to determine whether the assumed effect is valid and the assumed effect can be invalid if recent changes in the flow rate of the supplementary gas are above a third threshold.

In some configurations, the controller can be configured to control the flow rate of the supplementary gas into the device.

In some configurations, the controller can be configured to perform a frequency analysis of the modified first parameter dataset to make the estimate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient, can comprise using a controller of a respiratory device, receiving measurements of a first parameter of a gases flow or representative of performance of a component of the device, the first parameter indicative of the patient's respiration; receiving measurements of a second parameter of a gases flow or representative of performance of a component of the device; determining an assumed effect of the second parameter on the first parameter; and making an estimate about the patient using the assumed effect from the first parameter to output a modified first parameter.

In some configurations, the method can further comprise subtracting the assumed effect from the first parameter to output a modified first parameter and making the estimate based on the modified first parameter.

In some configurations, the estimate can include an estimate of the patient's respiratory rate. In some configurations, the estimate can include an estimate of whether the patient is wearing a patient interface of the system.

In some configurations, the first parameter can be flow rate.

In some configurations, the device can further comprise a blower including a motor and the second parameter can be motor speed.

In some configurations, the method can further comprise determining whether the assumed effect is valid and the assumed effect can be invalid if the motor speed is below a first threshold.

In some configurations, the method can further comprise determining whether the assumed effect is valid and the assumed effect can be invalid if recent changes in the motor speed are above a second threshold.

In some configurations, the second parameter can be pressure.

In some configurations, the first parameter can be flow rate, pressure, motor speed, power to motor, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the method can further comprise measuring a composition of the flow of gases after the ambient air and the supplementary gas have been mixed.

In some configurations, the method can further comprise determining whether the assumed effect is valid and the assumed effect can be invalid if recent changes in the composition of the flow of gases are above a third threshold.

In some configurations, the method can further comprise measuring a flow rate of the supplementary gas into the device.

In some configurations, the method can further comprise determining whether the assumed effect is valid and the assumed effect can be invalid if recent changes in the flow rate of the supplementary gas are above a third threshold.

In some configurations, the method can further comprise controlling the flow rate of the supplementary gas into the device.

In some configurations, the method can further comprise performing a frequency analysis of the modified first parameter to make the estimate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a respiratory system configured to deliver a respiratory therapy to a patient and also configured to provide information related to the patient can comprise a respiratory device comprising a controller and a blower configured to generate a flow of gases, the blower including a motor; wherein the controller can be configured to receive a gases flow measurement and a measurement indicative of impact of the blower on the gases flow, the controller configured to determine whether to add the gases flow measurement to a validated gases flow dataset based at least in part on the measurement indicative of impact of the blower on the gases flow, and patient connection and/or patient respiratory rate based at least in part on the validated gases flow dataset.

In some configurations, the gases flow measurement can be discarded if the measurement indicative of impact of the blower on the gases flow is below a first threshold.

In some configurations, the gases flow measurement can be discarded if recent changes in the measurement indicative of impact of the blower on the gases flow are above a second threshold.

In some configurations, the measurement indicative of impact of the blower on the gases flow can be a motor speed of the blower.

In some configurations, the measurement indicative of impact of the blower on the gases flow can be a pressure drop across the blower.

In some configurations, the first parameter can be flow rate, pressure, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the controller can be configured to measure a composition of the flow of gases after the ambient air and the supplementary gas have been mixed.

In some configurations, the gases flow measurement can be discarded if recent changes in the composition of the flow of gases are above a third threshold.

In some configurations, the controller can be configured to measure a flow rate of the supplementary gas into the device.

In some configurations, the gases flow measurement can be discarded if recent changes in the flow rate of the supplementary gas are above a third threshold.

In some configurations, the controller can be configured to control the flow rate of the supplementary gas into the device.

In some configurations, the controller can be configured to perform a frequency analysis of the validated flow dataset to determine patient connection and/or patient respiratory rate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient and can comprise a controller and a blower configured to generate a flow of gases, the blower including a motor, can comprise using the controller, receiving a gases flow measurement and a measurement indicative of impact of the blower on the gases flow; and determining whether to add the gases flow measurement to a validated gases flow dataset based at least in part on the measurement indicative of impact of the blower on the gases flow, and patient connection and/or patient respiratory rate based at least in part on the validated gases flow dataset.

In some configurations, the gases flow measurement can be discarded if the measurement indicative of impact of the blower on the gases flow is below a first threshold.

In some configurations, the gases flow measurement can be discarded if recent changes in the measurement indicative of impact of the blower on the gases flow are above a second threshold.

In some configurations, the measurement indicative of impact of the blower on the gases flow can be a motor speed of the blower.

In some configurations, the measurement indicative of impact of the blower on the gases flow can be a pressure drop across the blower.

In some configurations, the first parameter can be flow rate, pressure, flow resistance, carbon dioxide data, humidity, variants thereof, or any combinations thereof.

In some configurations, the flow of gases can comprise ambient air.

In some configurations, the flow of gases can comprise a supplementary gas.

In some configurations, the supplementary gas can comprise oxygen.

In some configurations, the method can further comprise measuring a composition of the flow of gases after the ambient air and the supplementary gas have been mixed.

In some configurations, the method can further comprise discarding the gases flow measurement if recent changes in the composition of the flow of gases are above a third threshold.

In some configurations, the method can further comprise measuring a flow rate of the supplementary gas into the device.

In some configurations, the method can further comprise discarding the gases flow measurement if recent changes in the flow rate of the supplementary gas are above a third threshold.

In some configurations, the method can further comprise controlling the flow rate of the supplementary gas into the device.

In some configurations, the method can further comprise performing a frequency analysis of the validated flow dataset to determine patient connection and/or patient respiratory rate.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a respiratory system configured to deliver a respiratory therapy to a patient and also configured to provide information related to the patient can comprise a respiratory device comprising a controller and a blower configured to generate a flow of gases, the blower including a motor; wherein the controller can be configured to receive a gases flow measurement and a measurement indicative of impact of the blower on the gases flow, the controller configured to estimate a gases flow parameter value resulting from the impact of the blower on the gases flow, and determine a difference between the measured gases parameter and the estimated gases flow parameter value resulting from the impact of the blower on the gases flow.

In some configurations, the controller can be configured to determine patient connection based at least in part on the difference.

In some configurations, the controller can be configured to estimate a respiratory rate based at least in part on the difference.

In some configurations, the gases flow parameter can be flow rate, pressure, flow resistance, carbon dioxide data, humidity, variants thereof, or any combinations thereof.

In some configurations, the measurement indicative of impact of the blower on the gases flow can be a motor speed of the blower.

In some configurations, the measurement indicative of impact of the blower on the gases flow can be a pressure drop across the blower.

In some configurations, the estimated gases flow parameter value resulting from the measurement indicative of impact of the blower can be above a threshold.

In some configurations, the controller can be configured to modify the measured gases flow parameter by subtracting the difference from the measured gases flow parameter and perform a frequency analysis of the modified measured gases flow parameter.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient and can comprise a controller and a blower configured to generate a flow of gases, the blower including a motor, can comprise using the controller, receiving a gases flow measurement and a measurement indicative of impact of the blower on the gases flow; estimating a gases flow parameter value resulting from the impact of the blower on the gases flow; and determining a difference between the measured gases parameter and the estimated gases flow parameter value resulting from the impact of the blower on the gases flow.

In some configurations, the method can further comprise determining patient connection based at least in part on the difference.

In some configurations, the method can further comprise estimating a respiratory rate based at least in part on the difference.

In some configurations, the gases flow parameter can be flow rate, pressure, flow resistance, carbon dioxide data, humidity, variants thereof, or any combinations thereof.

In some configurations, the measurement indicative of impact of the blower on the gases flow can be a motor speed of the blower.

In some configurations, the measurement indicative of impact of the blower on the gases flow can be a pressure drop across the blower.

In some configurations, the estimated gases flow parameter value resulting from the measurement indicative of impact of the blower can be above a threshold.

In some configurations, the method can further comprise modifying the measured gases flow parameter by subtracting the difference from the measured gases flow parameter and performing a frequency analysis of the modified measured gases flow parameter.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a respiratory system configured to deliver a respiratory therapy to a patient and also configured to provide information related to the patient's breathing can comprise a respiratory device comprising a controller, wherein the controller can be configured to: receive a signal of a parameter of a flow of gases indicative of the patient's respiration; perform a frequency analysis of the signal; identify a plurality of local maxima of the signal resulting from the frequency analysis; and output a frequency with a highest magnitude among the plurality of local maxima as an estimated respiratory rate.

In some configurations, the controller can be further configured to filter a magnitude of each waveform associated with each local maximum.

In some configurations, the outputted frequency can be a frequency of the highest filtered magnitude.

In some configurations, the controller can be configured to identify between two and five local maxima. In some configurations, the controller is configured to identify two local maxima. In some configurations, the controller is configured to identify three local maxima.

In some configurations, at each iteration of a frequency analysis algorithm, each local maximum can be estimated to be caused by the same waveform as a previous local maximum if its frequency is within a certain distance of the previous local maximum.

In some configurations, if a local maximum is estimated to be caused by the same waveform as a previous local maximum, a filtered value for the magnitude of the local maximum can be determined using the magnitude of the local maximum and a filtered magnitude of the previous local maxima.

In some configurations, if a frequency of a local maximum is not within a certain distance of a frequency of any previous local maximum, the local maximum can be determined to be caused by a new waveform.

In some configurations, if a local maximum is estimated to be caused by a new waveform, a filtered value for a magnitude of the local maximum can begin from zero, the filtered value for the magnitude of the local maximum being determined using the magnitude of the local maximum and an assumed previous magnitude of zero.

In some configurations, the frequency analysis can comprise a Goertzel algorithm.

In some configurations, the Goertzel algorithm can comprise a modified Goertzel algorithm.

In some configurations, the Goertzel algorithm can evaluate a magnitude of frequencies within a typical breathing frequency range.

In some configurations, the controller can further determine a signal quality of the estimated respiratory rate.

In some configurations, the parameter can be flow rate, pressure, motor speed, power to motor, flow resistance, carbon dioxide data, humidity, variants thereof, or any combinations thereof.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient's breathing, can comprise receiving a signal of a parameter of a flow of gases indicative of the patient's respiration; performing a frequency analysis of the signal; identifying a plurality of local maxima of the signal resulting from the frequency analysis; and outputting a frequency with a highest magnitude among the plurality of local maxima as an estimated respiratory rate.

In some configurations, the method can further comprise filtering a magnitude of each waveform associated with each local maximum.

In some configurations, the outputted frequency can be a frequency of the highest filtered magnitude.

In some configurations, the method can further comprise identifying between two and five local maxima. In some configurations, the method can further comprise identifying two local maxima. In some configurations, the method can further comprise identifying three local maxima.

In some configurations, at each iteration of a frequency analysis algorithm, the method can further comprise estimating each local maximum to be caused by the same waveform as a previous local maximum if its frequency is within a certain distance of the previous local maximum.

In some configurations, the method can further comprise determining a filtered value for the magnitude of the local maximum using the magnitude of the local maximum and a filtered magnitude of the previous local maxima if a local maximum is estimated to be caused by the same waveform as a previous local maximum.

In some configurations, the method can further comprise determining the local maximum to be caused by a new waveform if a frequency of a local maximum is not within a certain distance of a frequency of any previous local maximum.

In some configurations, the method can further comprise beginning a filtered value for a magnitude of the local maximum from zero if a local maximum is estimated to be caused by a new waveform, the filtered value for the magnitude of the local maximum being determined using the magnitude of the local maximum and an assumed previous magnitude of zero.

In some configurations, the frequency analysis can comprise a Goertzel algorithm.

In some configurations, the Goertzel algorithm can comprise a modified Goertzel algorithm.

In some configurations, the Goertzel algorithm can evaluate a magnitude of frequencies within a typical breathing frequency range.

In some configurations, the method can further comprise determining a signal quality of the estimated respiratory rate.

In some configurations, the parameter can be flow rate, pressure, motor speed, power to motor, flow resistance, carbon dioxide data, humidity, variants thereof, or any combinations thereof.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a respiratory system configured to deliver a respiratory therapy to a patient and also configured to provide information related to the patient's breathing can comprise a respiratory device comprising a controller, wherein the controller can be configured to: receive a signal of a parameter of a flow of gases indicative of the patient's respiration; estimate the patient's respiratory rate; evaluate a signal quality of the estimated respiratory rate; and output the estimated respiratory rate for display on the display screen based on the estimated respiratory rate having a sufficient quality.

In some configurations, the controller is configured to determine the estimated respiratory rate by performing a frequency analysis on the signal.

In some configurations, the frequency analysis can comprise a Goertzel algorithm.

In some configurations, the Goertzel algorithm can comprise a modified Goertzel algorithm.

In some configurations, the Goertzel algorithm can evaluate a magnitude of frequencies within a typical breathing frequency range.

In some configurations, evaluating the signal quality can be based in part on a magnitude of recent changes in the estimated respiratory rate.

In some configurations, evaluating the signal quality can be based in part on a magnitude of recent changes in an estimated breath period.

In some configurations, a larger magnitude of recent changes can be indicative of a poorer signal quality.

In some configurations, evaluating the signal quality can be based in part on a magnitude of recent changes in the estimated respiratory rate and in part on a magnitude of recent changes in an estimated breath period.

In some configurations, evaluating the signal quality can be based in part on a running variance of each of an estimated respiratory rate and an estimated breath period.

In some configurations, evaluating the signal quality can be based in part on a magnitude of a frequency transform associated with the estimated respiratory rate.

In some configurations, smaller magnitudes can be indicative of a poorer signal quality.

In some configurations, the parameter can be flow rate, pressure, motor speed, power to motor, flow resistance, carbon dioxide data, humidity, variants thereof, or any combinations thereof.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

In some configurations, a method of using a respiratory system to deliver a respiratory therapy to a patient, wherein the respiratory system can also be configured to provide information related to the patient's breathing, can comprise receiving a signal of a parameter of a flow of gases indicative of the patient's respiration; estimating the patient's respiratory rate; evaluating a signal quality of the estimated respiratory rate; and outputting the estimated respiratory rate for display on the display screen based on the estimated respiratory rate having a sufficient quality.

In some configurations, the method can further comprise determining the estimated respiratory rate by performing a frequency analysis on the signal.

In some configurations, the frequency analysis can comprise a Goertzel algorithm.

In some configurations, the Goertzel algorithm can comprise a modified Goertzel algorithm.

In some configurations, the Goertzel algorithm can evaluate a magnitude of frequencies within a typical breathing frequency range.

In some configurations, evaluating the signal quality can be based in part on a magnitude of recent changes in the estimated respiratory rate.

In some configurations, evaluating the signal quality can be based in part on a magnitude of recent changes in an estimated breath period.

In some configurations, a larger magnitude of recent changes can be indicative of a poorer signal quality.

In some configurations, evaluating the signal quality can be based in part on a magnitude of recent changes in the estimated respiratory rate and in part on a magnitude of recent changes in an estimated breath period.

In some configurations, evaluating the signal quality can be based in part on a running variance of each of an estimated respiratory rate and an estimated breath period.

In some configurations, evaluating the signal quality can be based in part on a magnitude of a frequency transform associated with the estimated respiratory rate.

In some configurations, smaller magnitudes can be indicative of a poorer signal quality.

In some configurations, the parameter can be flow rate, pressure, motor speed, power to motor, flow resistance, carbon dioxide data, humidity, variants thereof, or any combinations thereof.

In some configurations, the system can comprise a non-sealed system.

In some configurations, the system can be configured to deliver a nasal high flow therapy.

In some configurations, the system can comprise a sealed system.

In some configurations, the system can be configured to deliver a CPAP therapy.

In some configurations, the system can be configured to deliver a bilevel therapy.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain examples are described below, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described below.

Overview of Example Flow Therapy Apparatus

Figure 1:
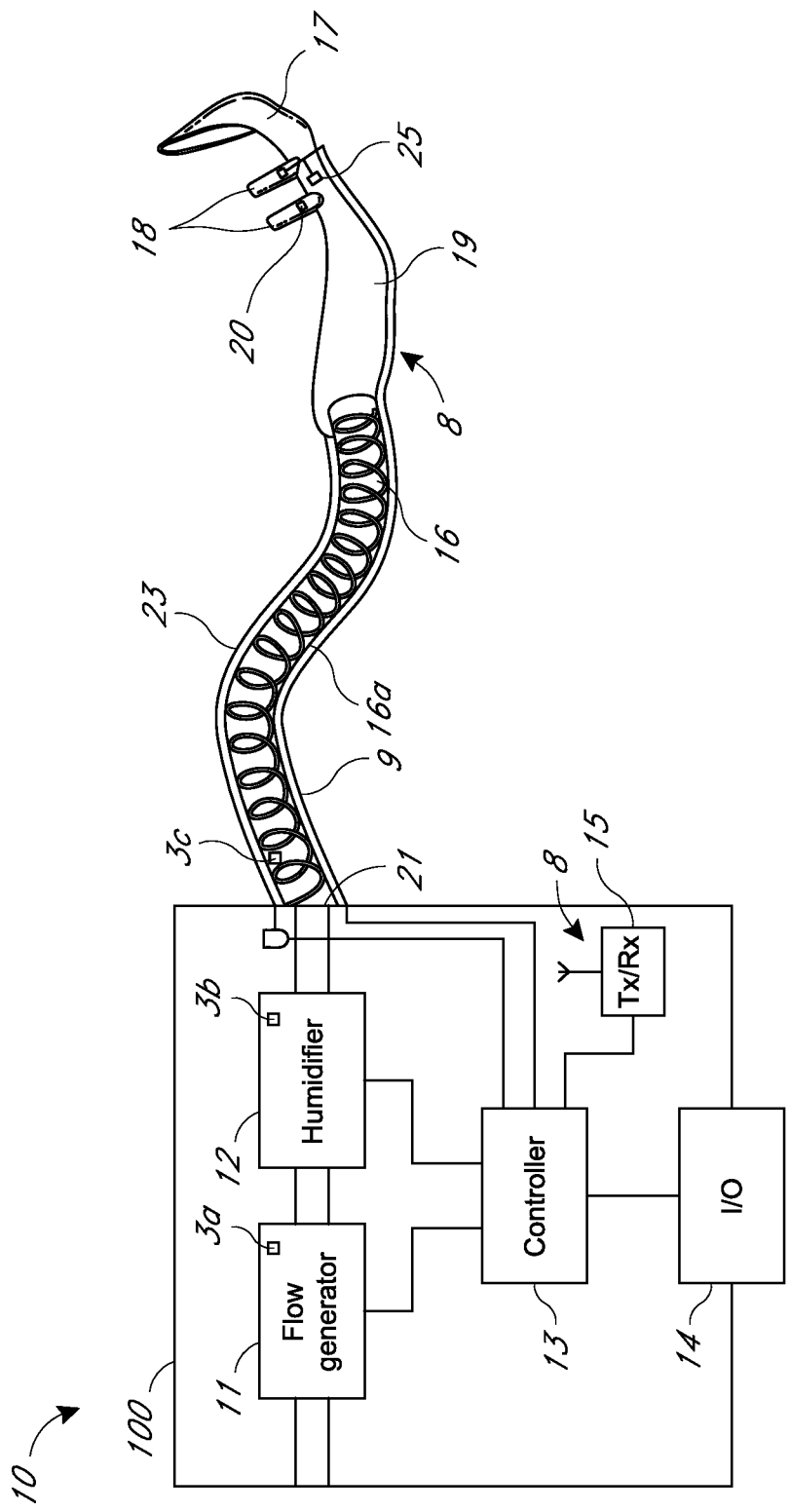
FIG. 1 shows schematically a respiratory system configured to provide a respiratory therapy to a patient.
Figure 2:
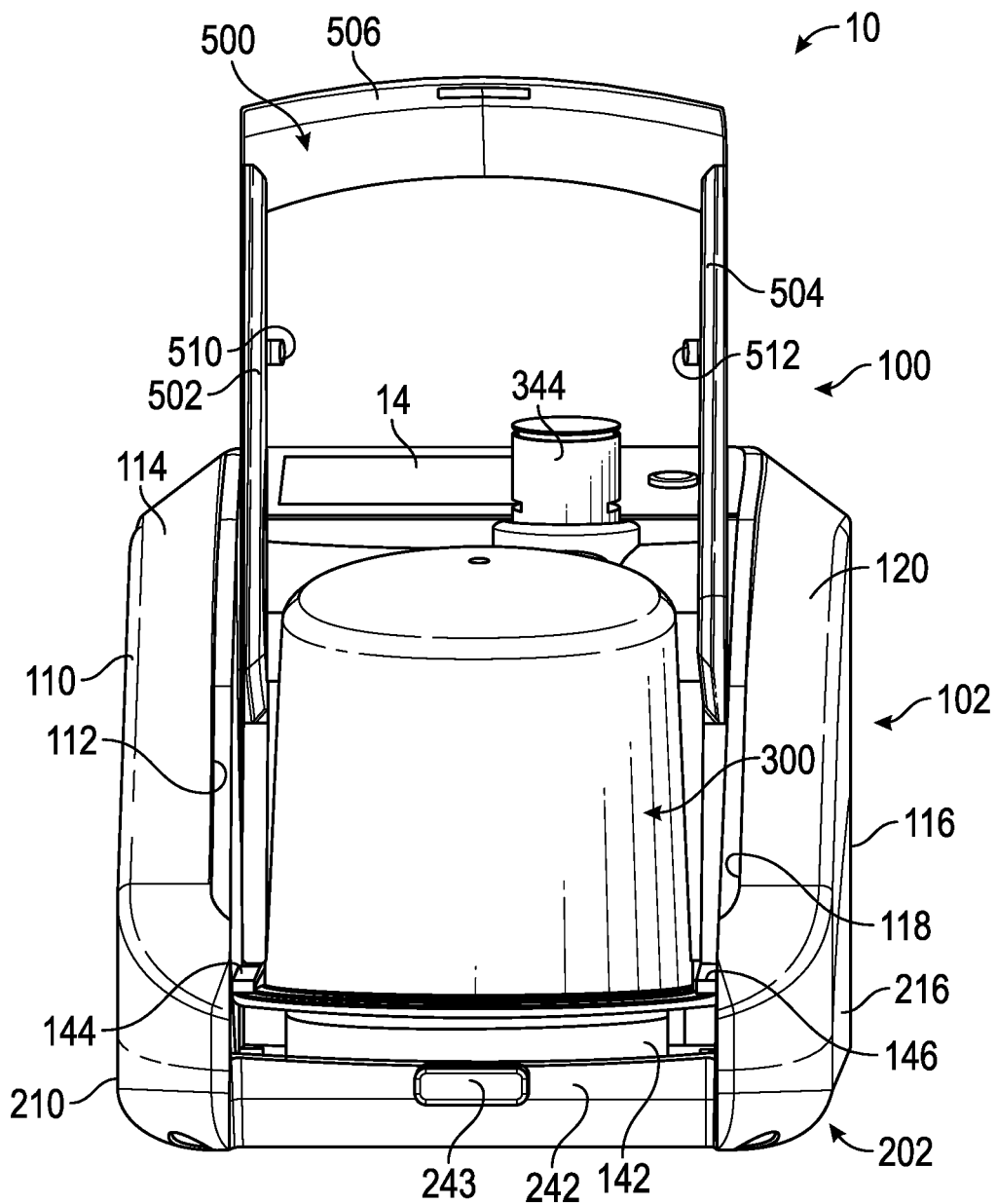
FIG. 2 is a front view of an example respiratory device with a humidification chamber in position and a raised handle/lever.
Figure 3:
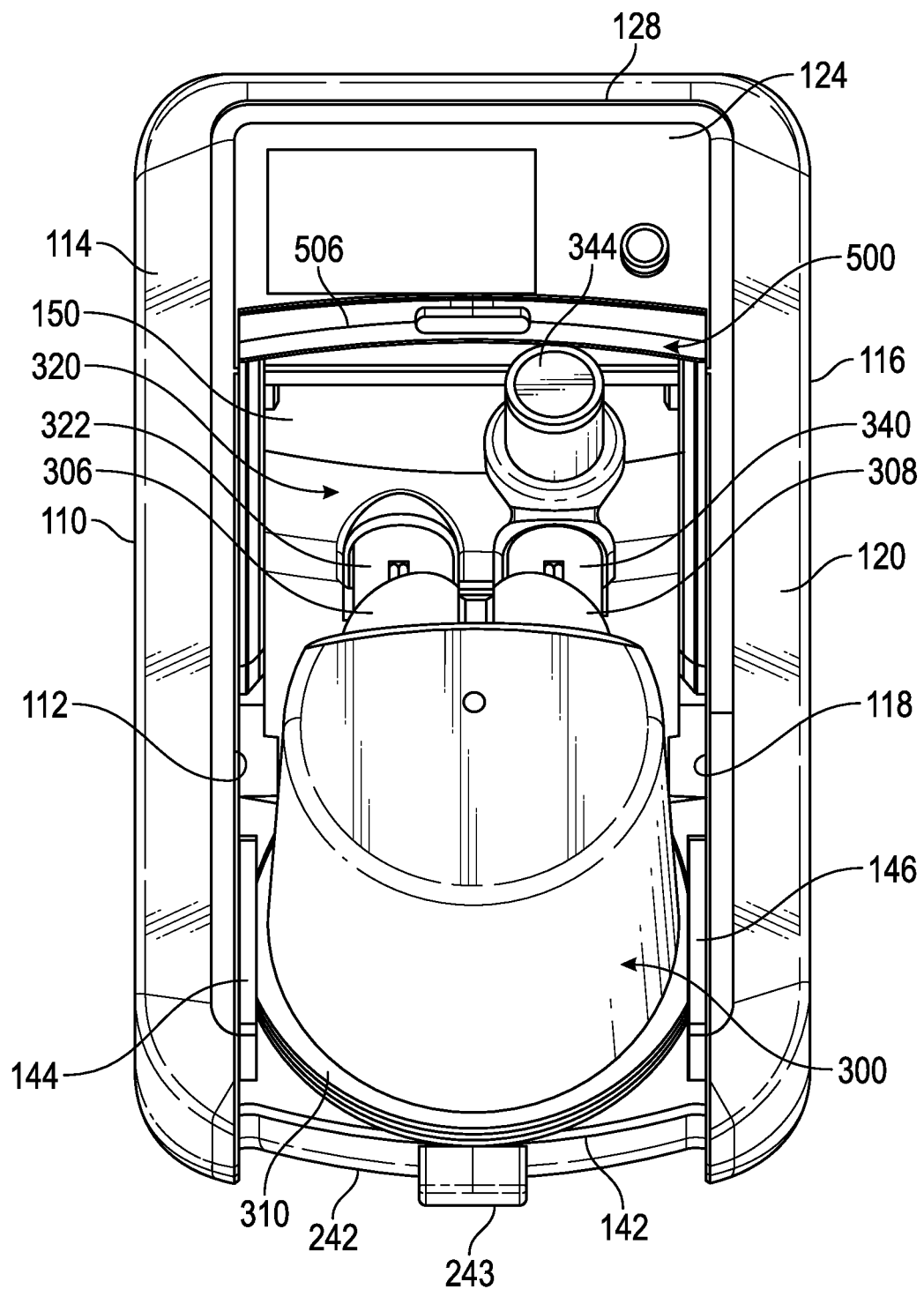
FIG. 3 is a top view corresponding to FIG. 2.
Figure 4:
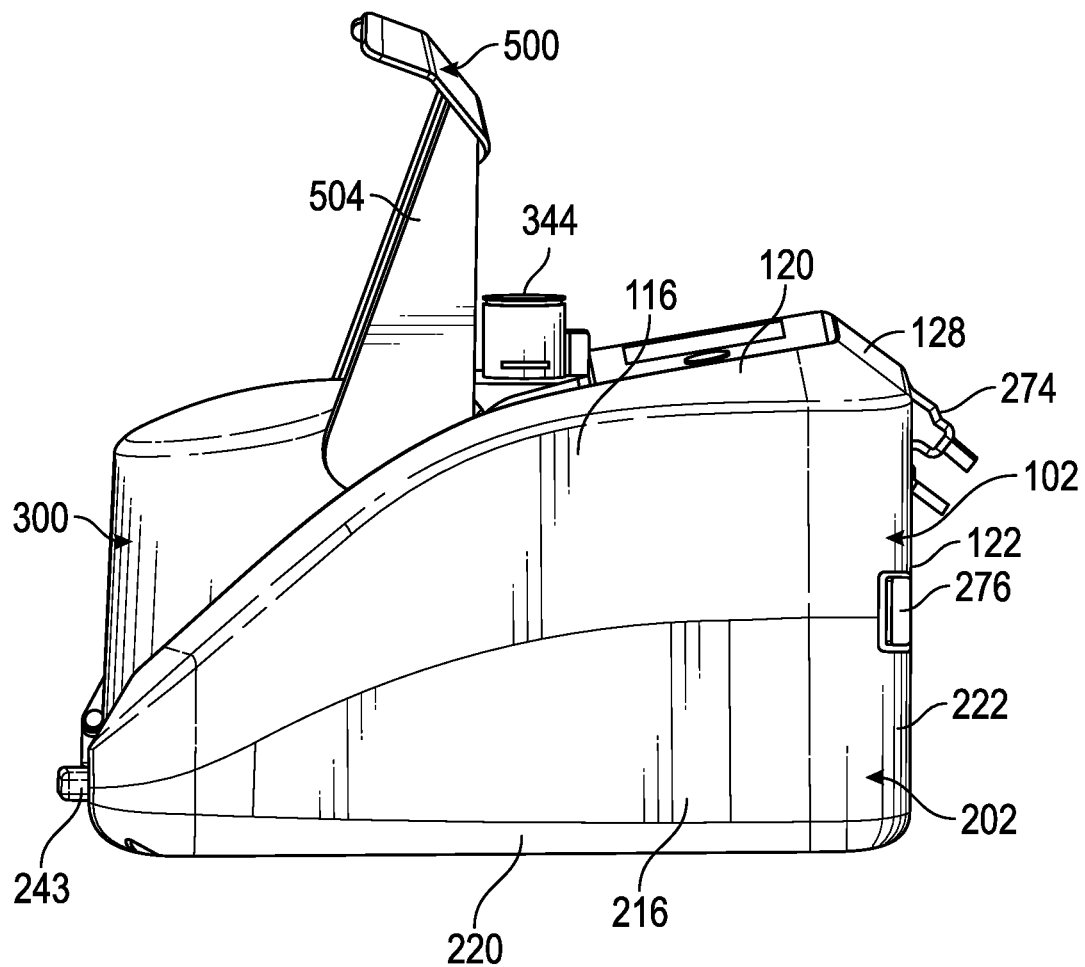
FIG. 4 is a right side view corresponding to FIG. 2.
Figure 5:
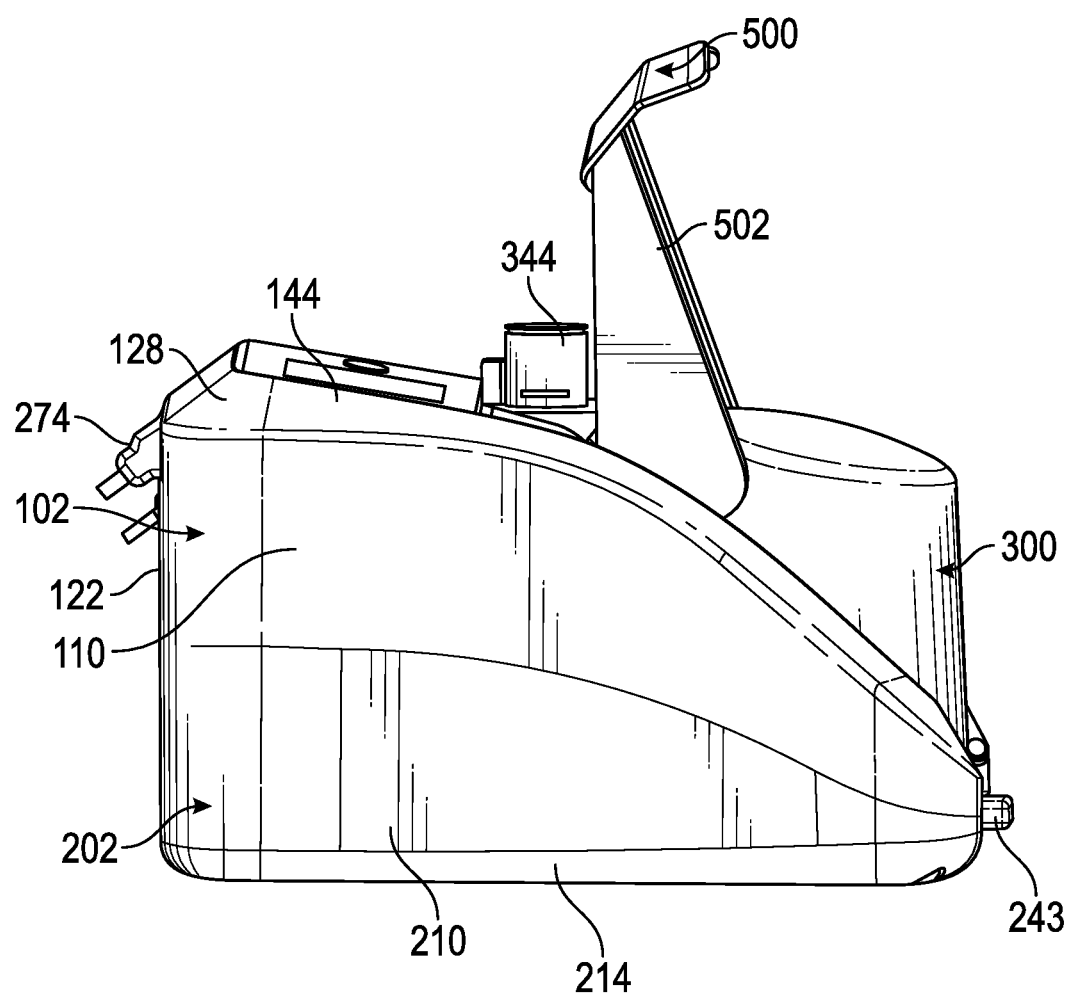
FIG. 5 is a left side view corresponding to FIG. 2.
Figure 6:
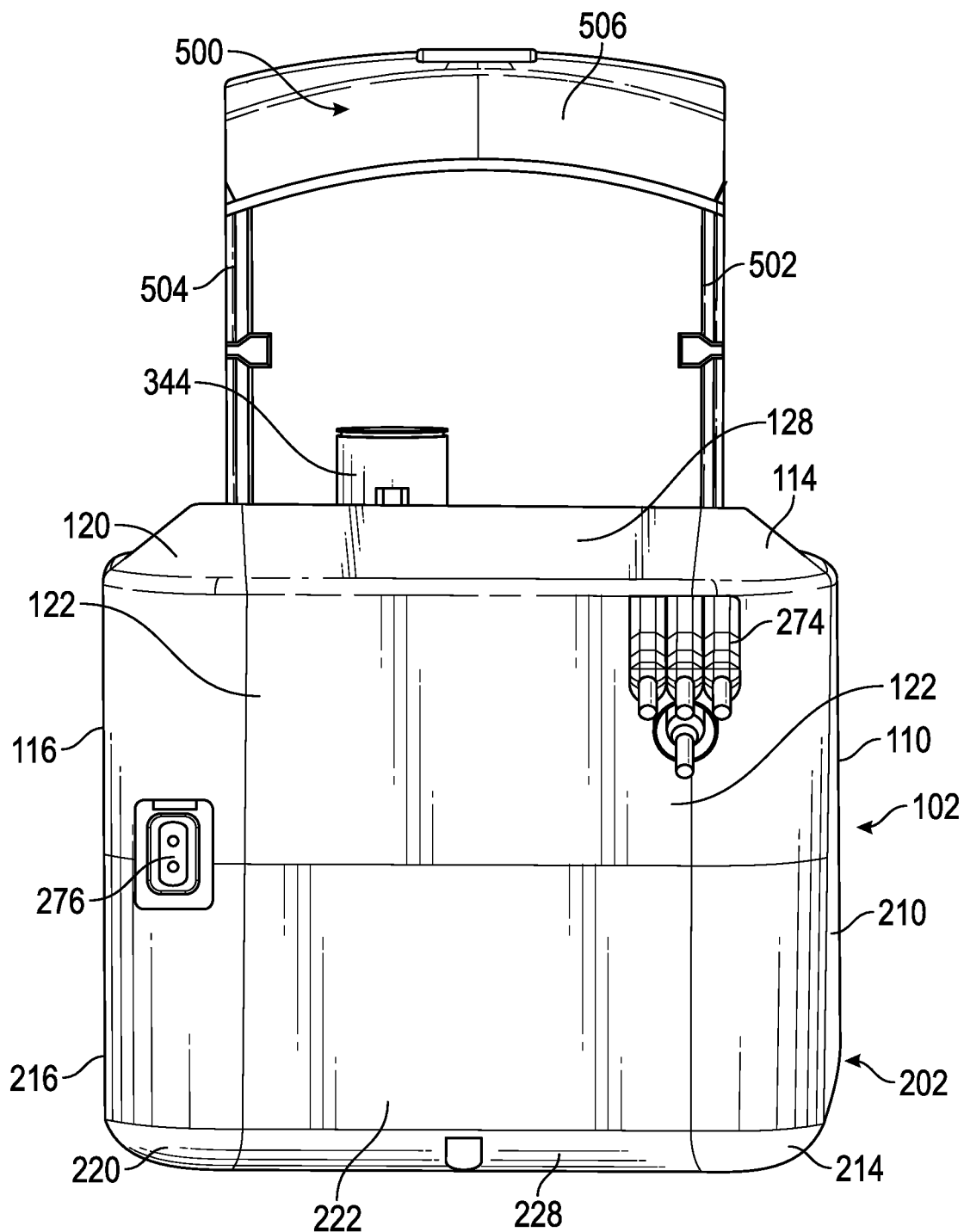
FIG. 6 is a rear view corresponding to FIG. 2.
Figure 7:
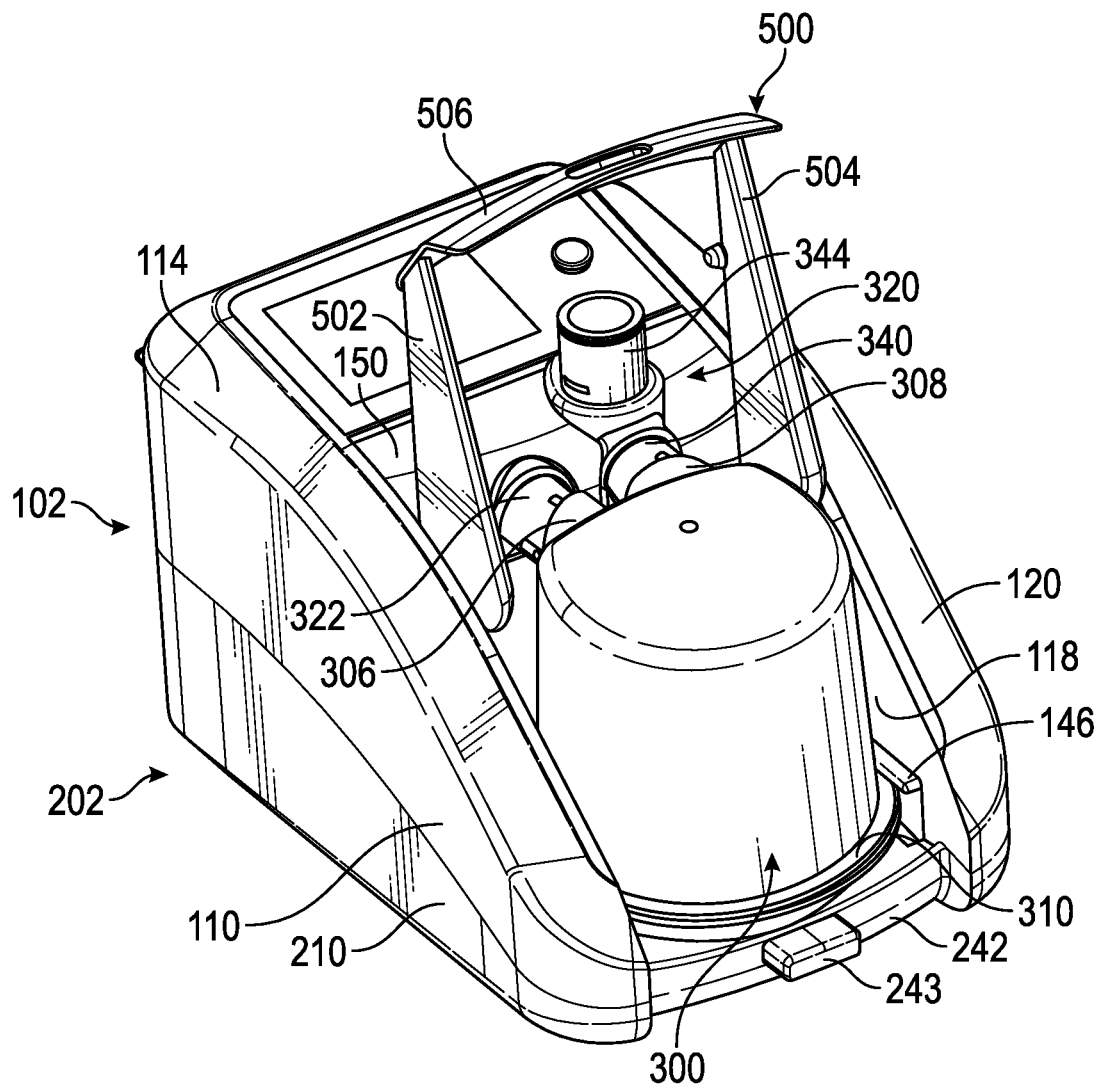
FIG. 7 is a front left perspective view corresponding to FIG. 2.

A schematic representation of a respiratory system 10 is provided in FIG. 1. The respiratory system 10 can include a main device housing 100. The main device housing 100 can contain a flow generator 11 that can be in the form of a motor/impeller arrangement, an optional humidifier or humidification chamber 12, a controller 13, and a user interface 14. The user interface 14 can include a display and input device(s) such as button(s), a touch screen, a combination of a touch screen and button(s), or the like. The controller 13 can include one or more hardware and/or software processors and can be configured or programmed to control the components of the apparatus, including but not limited to operating the flow generator 11 to create a flow of gases for delivery to a patient, operating the humidifier 12 (if present) to humidify and/or heat the gases flow, receiving user input from the user interface 14 for reconfiguration and/or user-defined operation of the respiratory system 10, and outputting information (for example on the display) to the user. The user can be a patient, healthcare professional, or others.

With continued reference to FIG. 1, a patient breathing conduit 16 can be coupled to a gases flow outlet 21 in the main device housing 100 of the respiratory system 10, and be coupled to a patient interface 17, such as a non-sealing interface like a nasal cannula with a manifold 19 and nasal prongs 18. The patient breathing conduit 16 can also be coupled to a face mask, a nasal mask, a nasal pillow mask, an endotracheal tube, a tracheostomy interface, or others.

The gases flow can be generated by the flow generator 11, and may be humidified, before being delivered to the patient via the patient conduit 16 through the patient interface 17. The controller 13 can control the flow generator 11 to generate a gases flow of a desired flow rate, and/or one or more valves to control mixing of air and oxygen or other breathable gas. The controller 13 can control a heating element in the humidification chamber 12, if present, to heat the gases to a desired temperature that achieves a desired level of temperature and/or humidity for delivery to the patient. The patient conduit 16 can have a heating element 16a, such as a heater wire, to heat gases flow passing through to the patient. The heating element 16a can also be under the control of the controller 13.

The system 10 can use ultrasonic transducer(s), flow sensor(s) such as a thermistor flow sensor, pressure sensor(s), temperature sensor(s), humidity sensor(s), or other sensors, in communication with the controller 13, to monitor characteristics of the gases flow and/or operate the system 10 in a manner that provides suitable therapy. The gases flow characteristics can include gases concentration, flow rate, pressure, temperature, humidity, or others. The sensors 3a, 3b, 3c, 20, 25, such as pressure, temperature, humidity, and/or flow sensors, can be placed in various locations in the main device housing 100, the patient conduit 16, and/or the patient interface 17. The controller 13 can receive output from the sensors to assist it in operating the respiratory system 10 in a manner that provides suitable therapy, such as to determine a suitable target temperature, flow rate, and/or pressure of the gases flow. Providing suitable therapy can include meeting a patient's inspiratory demand.

The system 10 can include a wireless data transmitter and/or receiver, or a transceiver 15 to enable the controller 13 to receive data signals 8 in a wireless manner from the operation sensors and/or to control the various components of the system 10. Additionally, or alternatively, the data transmitter and/or receiver 15 can deliver data to a remote server or enable remote control of the system 10. The system 10 can include a wired connection, for example, using cables or wires, to enable the controller 13 to receive data signals 8 from the operation sensors and/or to control the various components of the system 10.

The flow therapy apparatus 10 may comprise a high flow therapy apparatus. As used herein, "high flow" therapy refers to administration of gas to the airways of a patient at a relatively high flow rate that meets or exceeds the peak inspiratory demand of the patient. The flow rates used to achieve "high flow" may be any of the flow rates listed below. For example, in some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may deliver gases to the patient at a flow rate of between about 1 LPM and about 100 LPM, or at a flow rate in any of the sub-ranges outlined above.

High flow therapy can be effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gases flow. The flushing effect can create a reservoir of fresh gas available of each and every breath, while minimizing re-breathing of carbon dioxide, nitrogen, etc.

The patient interface for use in a high flow therapy can be a non-sealing interface to prevent barotrauma, which can include tissue damage to the lungs or other organs of the patient's respiratory system due to difference in pressure relative to the atmosphere. The patient interface can be a nasal cannula with a manifold and nasal prongs, and/or a face mask, and/or a nasal pillows mask, and/or a nasal mask, and/or a tracheostomy interface, or any other suitable type of patient interface.

Figure 15:
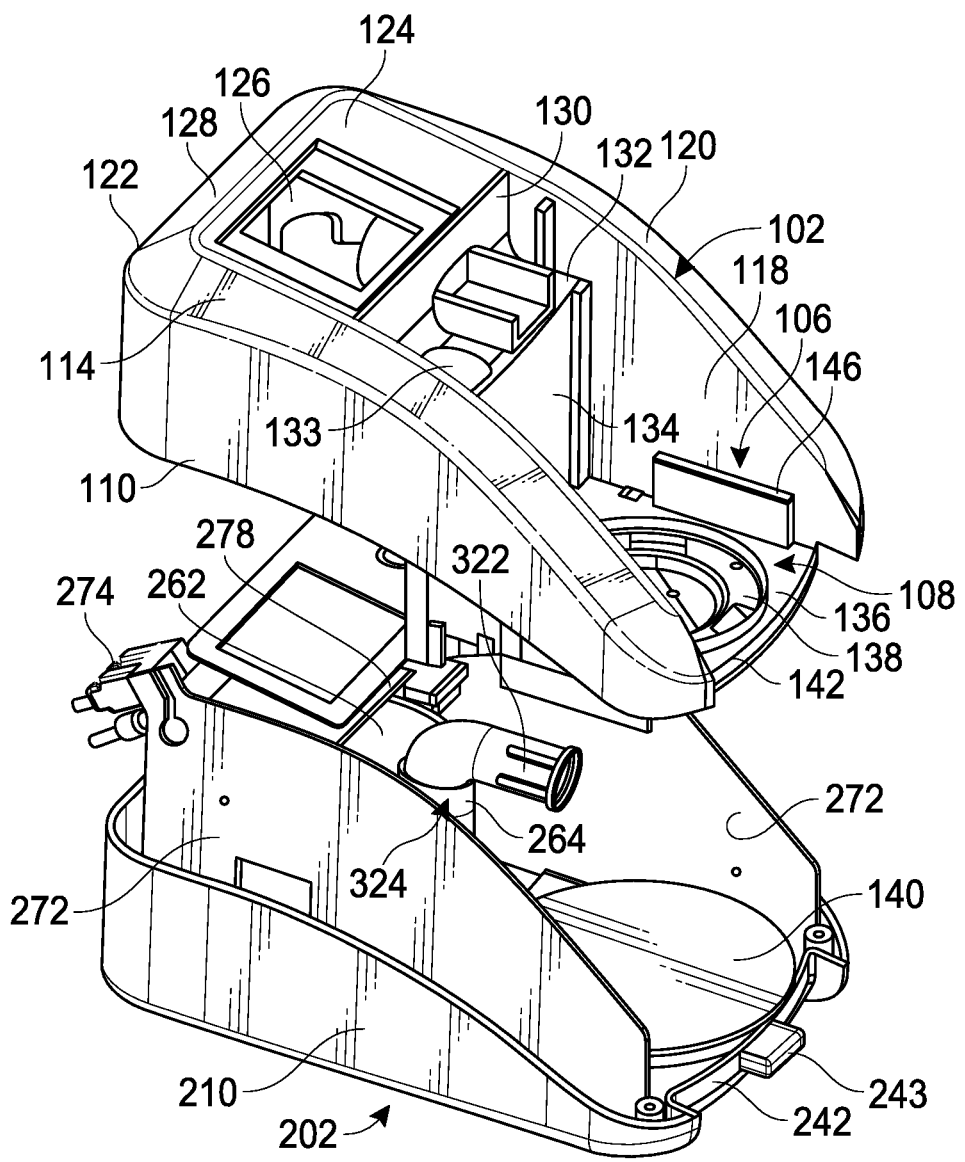
FIG. 15 is an exploded view of upper and lower chassis components of a main housing of the respiratory device.
Figure 16:
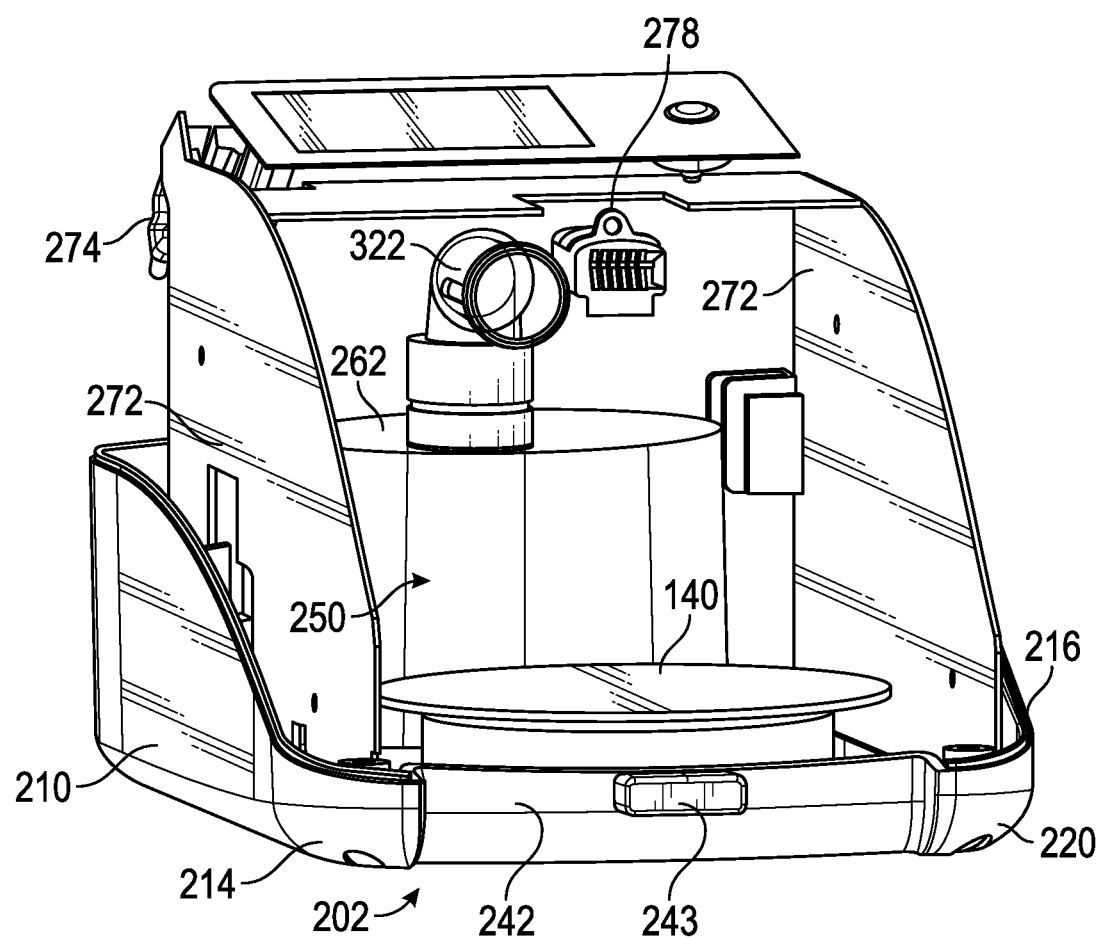
FIG. 16 is a front left side perspective view of the lower chassis of the main housing showing a housing for receipt of a motor/sensor module sub-assembly.

FIGS. 2 to 17B show an example respiratory device of the respiratory system 10 having a main housing 100. The main housing 100 has a main housing upper chassis 102 and a main housing lower chassis 202. The main housing upper chassis 102 has a peripheral wall arrangement 106 (see FIG. 15). The peripheral wall arrangement defines a humidifier or humidification chamber bay 108 for receipt of a removable humidification chamber 300. The removable humidification chamber 300 contains a suitable liquid such as water for humidifying gases that can be delivered to a patient.

In the form shown, the peripheral wall arrangement 106 of the main housing upper chassis 102 can include a substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 can further include a substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but can alternatively be substantially horizontal or inwardly angled.

The main housing upper chassis 102 can further include a substantially vertical rear outer wall 122. An upper part of the main housing upper chassis 102 can include a forwardly angled surface 124. The surface 124 can have a recess 126 for receipt of a display and user interface module 14. The display can be configured to display characteristics of sensed gas(es) in real time. An interconnecting wall 128 can extend between and interconnect the upper end of the rear outer wall 122 and the rear edge of the surface 124.

A substantially vertical wall portion 130 can extend downwardly from a front end of the surface 124. A substantially horizontal wall portion 132 can extend forwardly from a lower end of the wall portion 130 to form a ledge. A substantially vertical wall portion 134 can extend downwardly from a front end of the wall portion 132 and terminate at a substantially horizontal floor portion 136 of the humidification chamber bay 108. The left side inner wall 112, right side inner wall 118, wall portion 134, and floor portion 136 together can define the humidification chamber bay 108. The floor portion 136 of the humidification chamber bay 108 can have a recess 138 to receive a heater arrangement such as a heater plate 140 or other suitable heating element(s) for heating liquid in the humidification chamber 300 for use during a humidification process.

The main housing lower chassis 202 can be attachable to the upper chassis 102, either by suitable fasteners or integrated attachment features such as clips for example. The main housing lower chassis 202 can include a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 can further include a substantially vertical rear outer wall 222 that is contiguous with the rear outer wall 122 of the upper chassis 102.

The lower housing chassis 202 can have a lip 242 that is contiguous with the lip 142 of the upper housing chassis 102, and also forms part of the recess for receiving the handle portion 506 of the lever 500. The lower lip 242 can include a forwardly directed protrusion 243 that acts as a retainer for the handle portion 506 of the lever 500. Instead of the lever 500, the system can have a spring loaded guard to retainer the humidification chamber 300 in the humidification chamber bay 108.

An underside of the lower housing chassis 202 can include a bottom wall 230. Respective interconnecting walls 214, 220, 228 can extend between and interconnect the substantially vertical walls 210, 216, 222 and the bottom wall 230. The bottom wall 230 can include a grill 232 comprising a plurality of apertures to enable drainage of liquid in case of leakage from the humidification chamber 300 (e.g. from spills). The bottom wall 230 additionally can include elongated forward-rearward oriented slots 234. The slots 234 can additionally enable drainage of liquid in case of leakage from the humidification chamber 300, without the liquid entering the electronics housing. In the illustrated configuration, the slots 234 can be wide and elongate relative to the apertures of the grill 232 to maximize the drainage of liquid.

Figure 17:
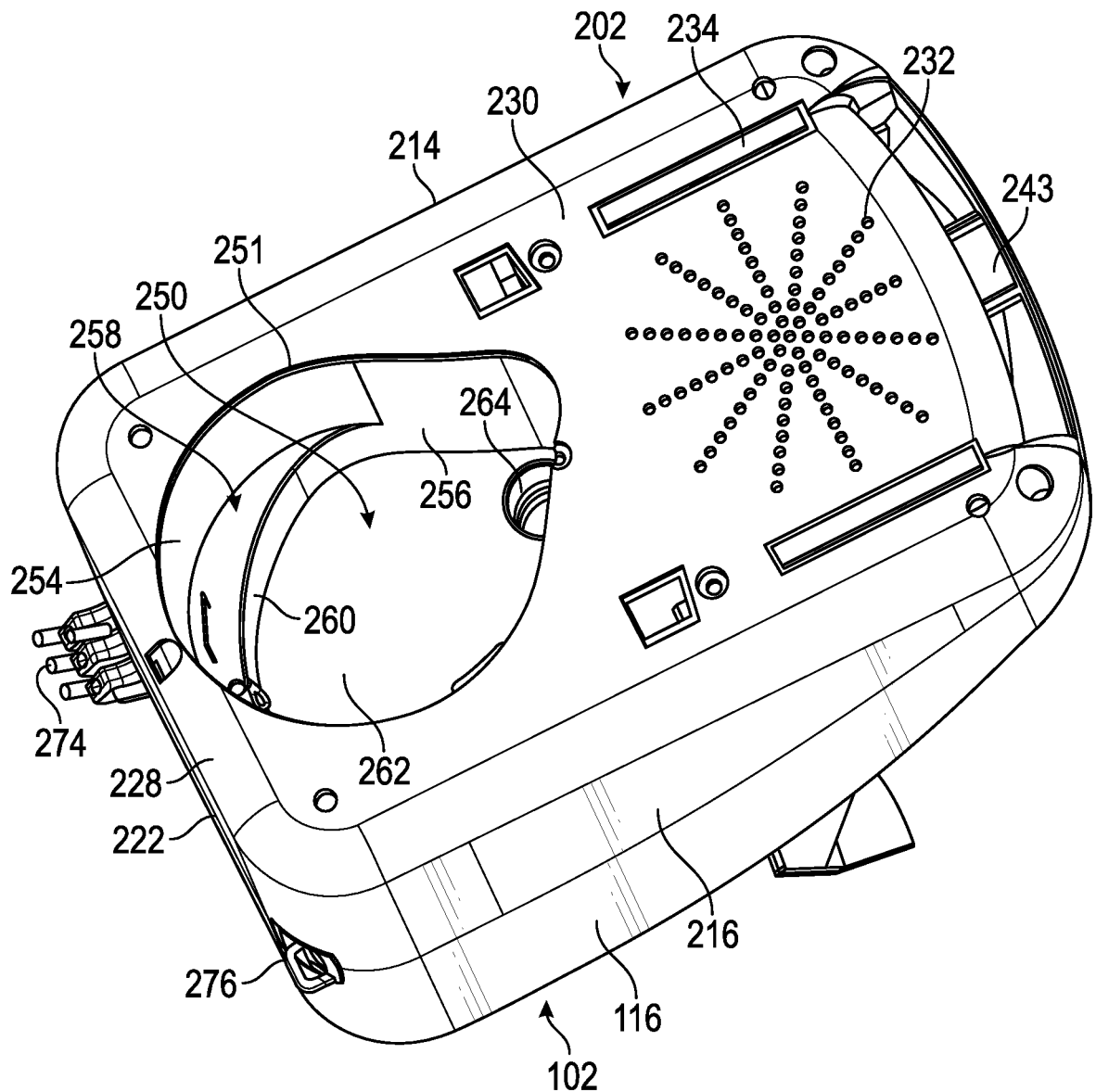
FIG. 17 is a first underside perspective view of the main housing of the respiratory device showing a recess inside the housing for the motor/sensor module sub-assembly.
Figure 18:
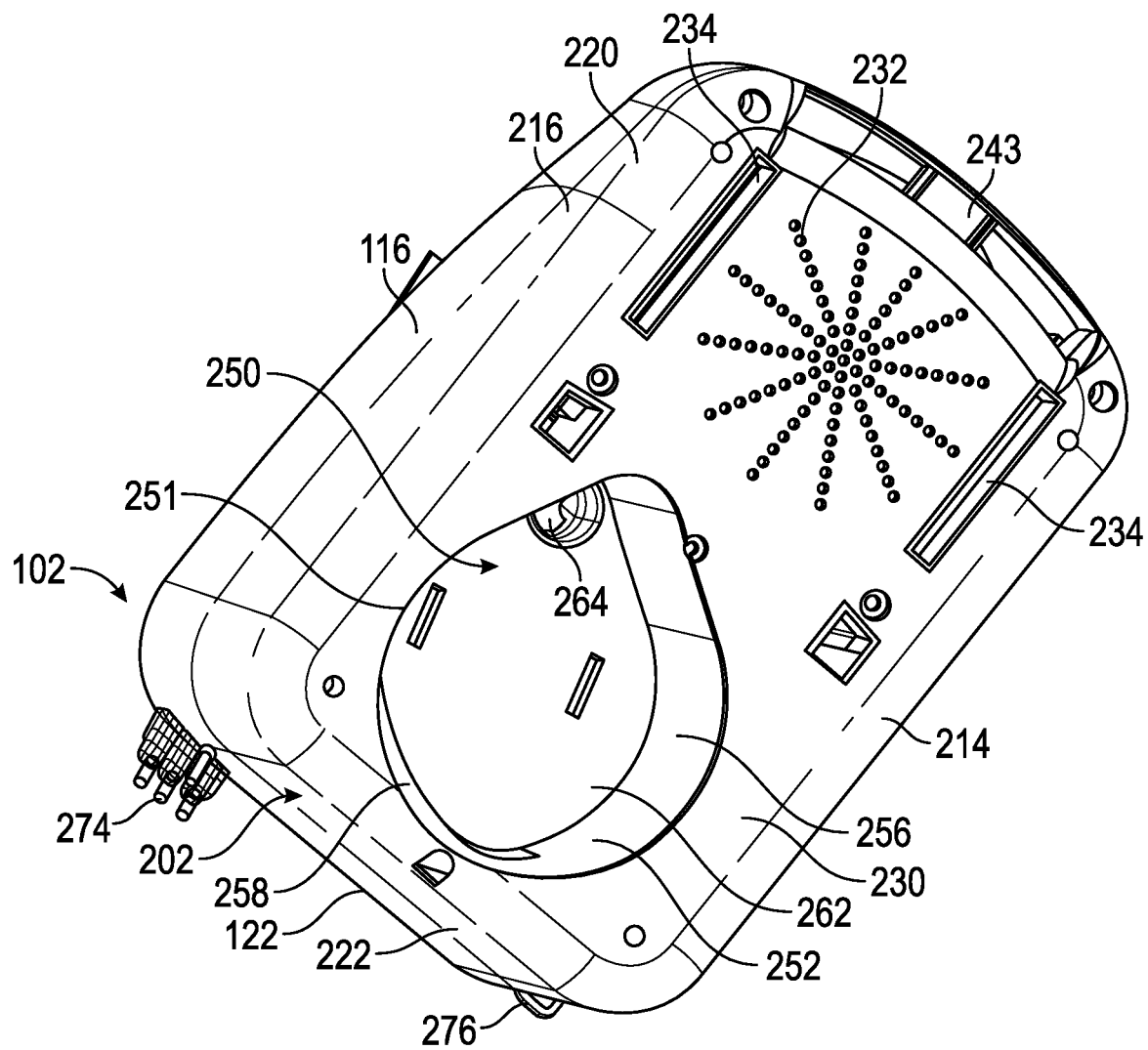
FIG. 18 is a second underside perspective view of the main housing of the respiratory device showing the recess for the motor/sensor module sub-assembly.

As shown in FIGS. 17 to 18, the lower chassis 202 can have a motor recess 250 for receipt of a motor and/or sensor module. The motor and/or sensor module may be non-removable from the main housing 100. The motor and/or sensor module can be removable from the main housing 100, as illustrated in FIGS. 17-18. A recess opening 251 can be provided in the bottom wall 230 adjacent a rear edge thereof, for receipt of a motor/sensor module. A continuous, gas impermeable, unbroken peripheral wall 252 can be integrally formed with the bottom wall 230 of the lower chassis 202 and extend upwardly from the periphery of the opening 251. A rearward portion 254 of the peripheral wall 252 has a first height, and a forward portion 256 of the peripheral wall 252 has a second height that is greater than the first height. The rearward portion 254 of the peripheral wall 252 terminates at a substantially horizontal step 258, which in turn terminates at an upper auxiliary rearward portion 260 of the peripheral wall 252. The forward portion 256 and upper auxiliary rearward portion 260 of the peripheral wall 252 terminate at a ceiling 262. All of the walls and the ceiling 262 can be continuous, gas impermeable, and unbroken other than the gases flow passage. Therefore, the entire motor recess 250 can be gas impermeable and unbroken, other than the gases flow passage.

The motor and/or sensor module can be insertable into the recess 250 and attachable to the lower chassis 202. Upon insertion of the motor and/or sensor module into the lower chassis 202, the gases flow passage tube 264 can extend through the downward extension tube 133 and be sealed by the soft seal.

The humidification chamber 300 can be fluidly coupled to the apparatus 10 in a linear slide-on motion in a rearward direction of the humidification chamber 300 into the chamber bay 108, from a position at the front of the housing 100 in a direction toward the rear of the housing 100. A gases outlet port 322 can be in fluid communication with the motor.

Figure 8:
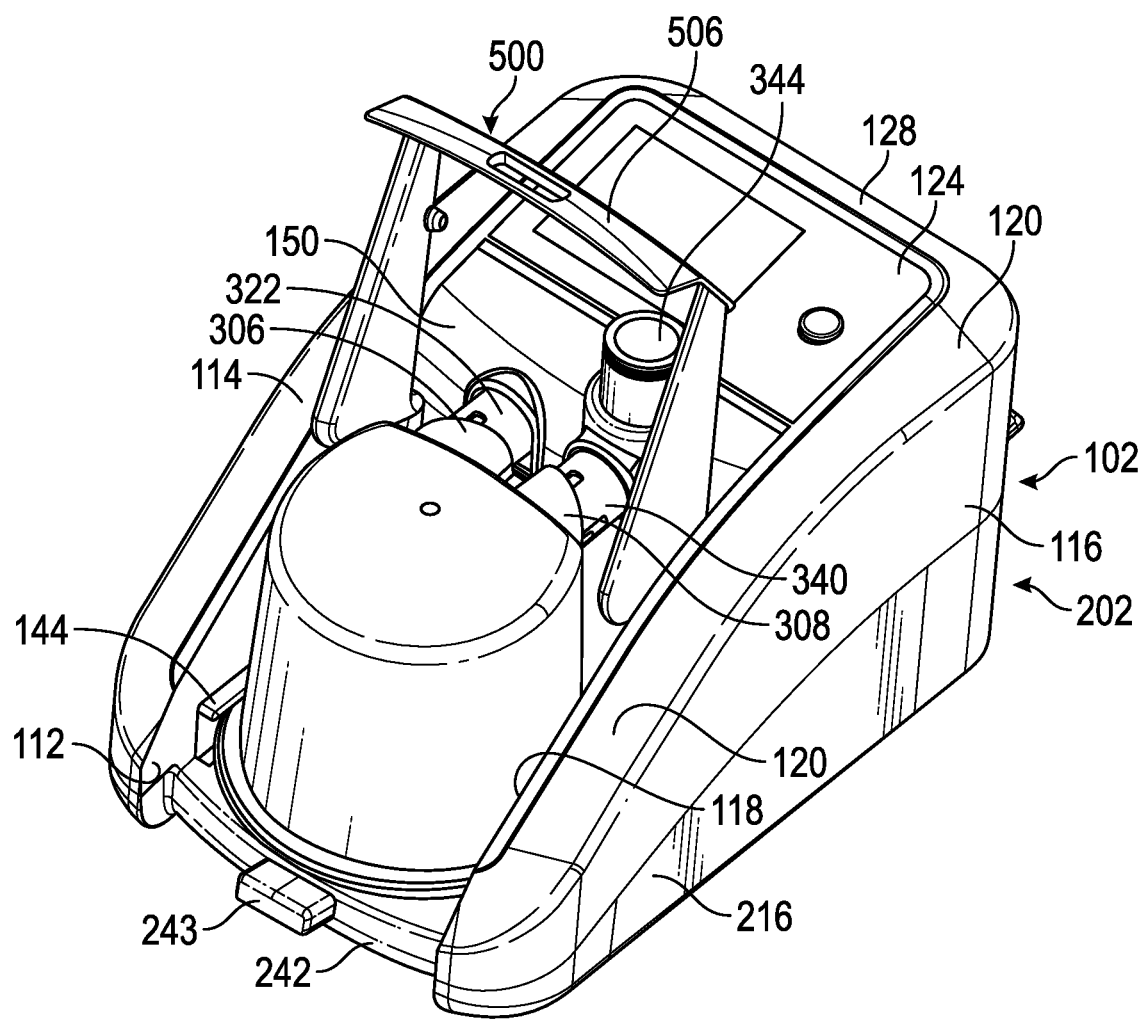
FIG. 8 is a front right perspective view corresponding to FIG. 2.
Figure 9:
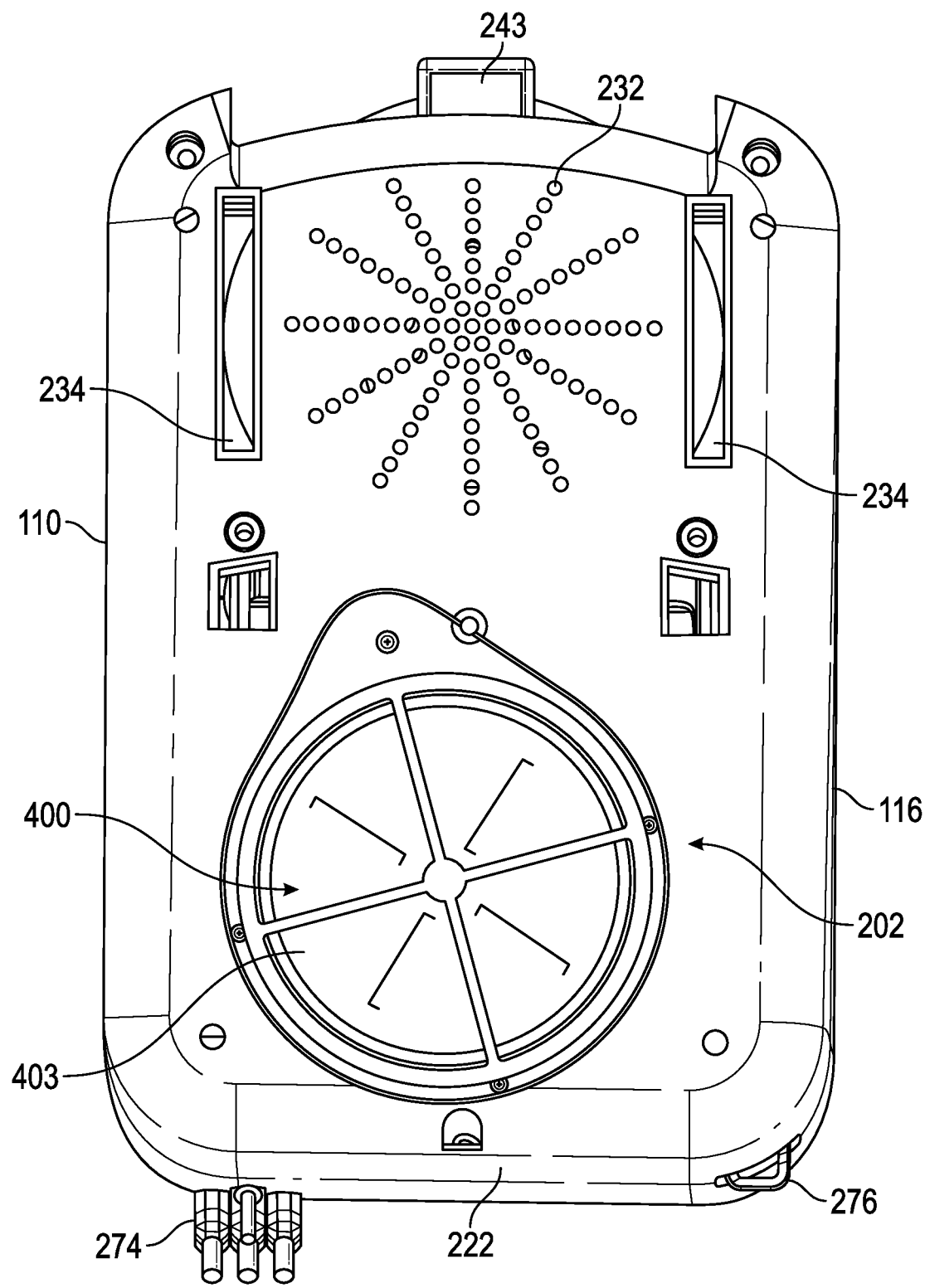
FIG. 9 is a bottom view corresponding to FIG. 2.

A gases inlet port 340 (humidified gases return) as shown in FIG. 8 can include a removable L-shaped elbow. The removable elbow can further include a patient outlet port 344 for coupling to the patient conduit 16 to deliver gases to the patient interface 17. The gases outlet port 322, gases inlet port 340, and patient outlet port 344 each can have soft seals such as O-ring seals or T-seals to provide a sealed gases passageway between the apparatus 10, the humidification chamber 300, and the patient conduit 16.

The humidification chamber gases inlet port 306 can be complementary with the gases outlet port 322, and the humidification chamber gases outlet port 308 can be complementary with the gases inlet port 340. The axes of those ports can be parallel to each other to enable the humidification chamber 300 to be inserted into the chamber bay 108 in a linear movement.

Figure 10:
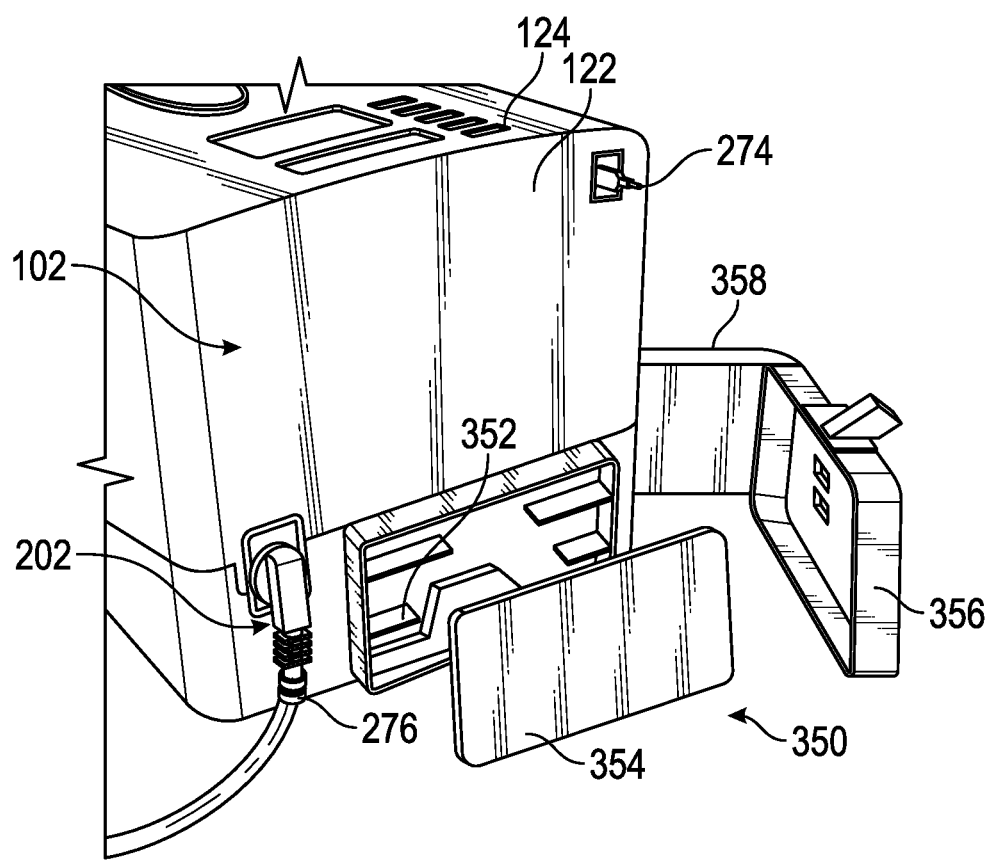
FIG. 10 shows an example configuration of an air and oxygen inlet arrangement of the flow therapy apparatus.
Figure 11:
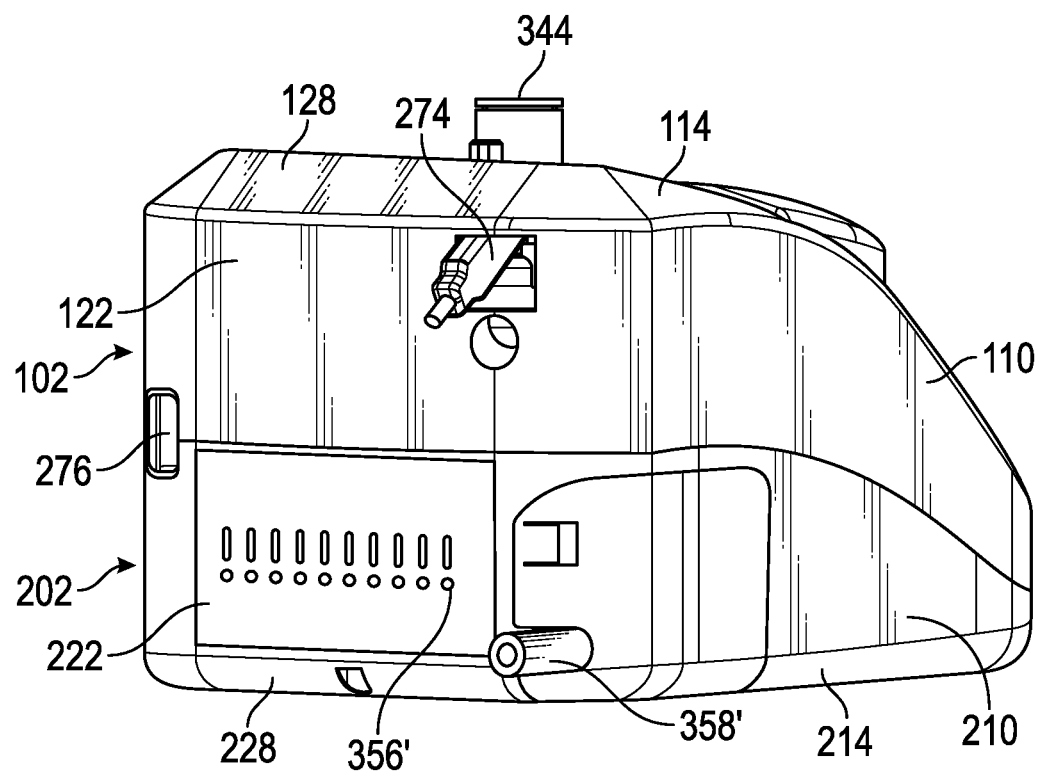
FIG. 11 shows another example configuration of an air and oxygen inlet arrangement of the respiratory device.
Figure 12:
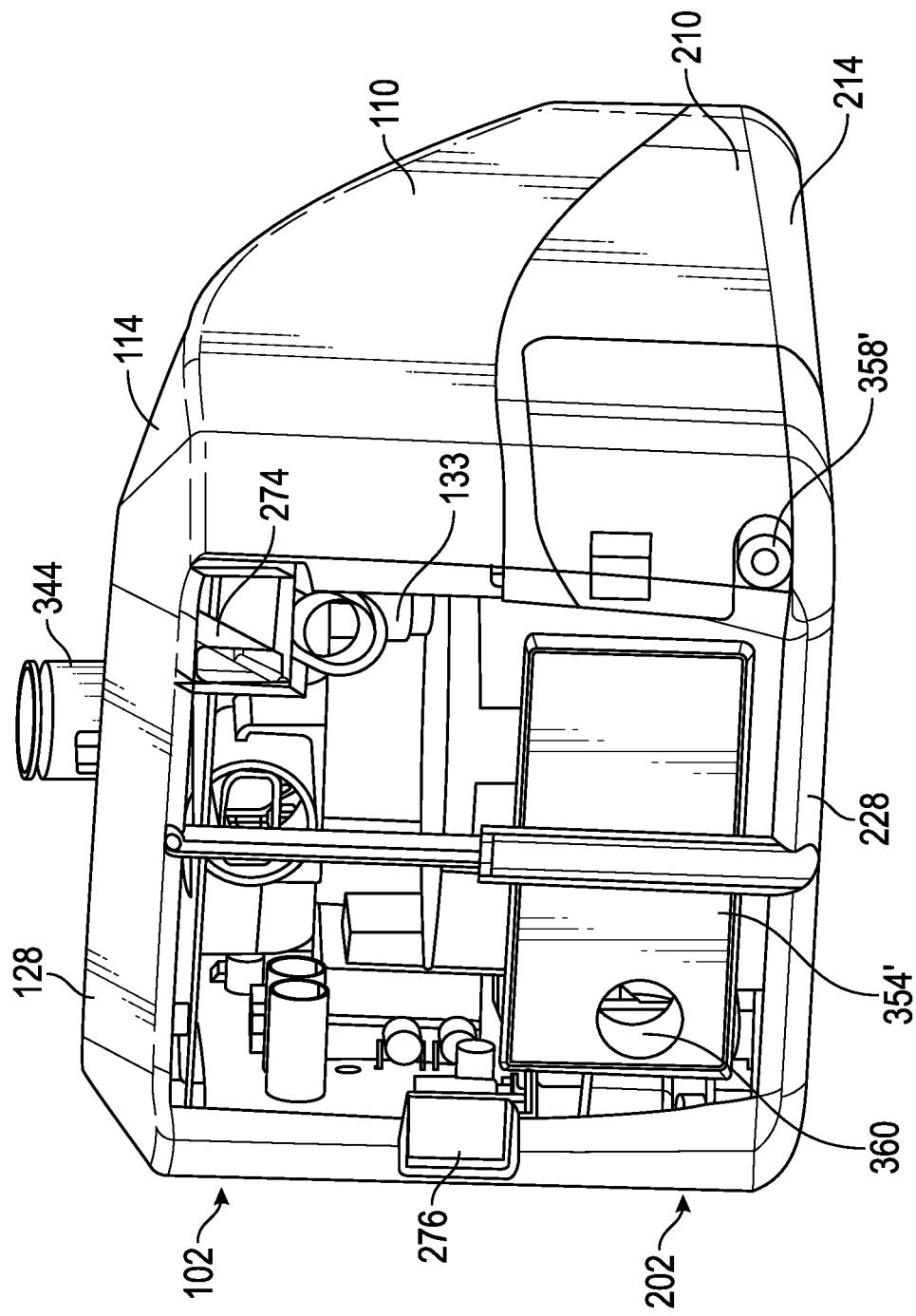
FIG. 12 is a transverse sectional view showing further detail of the air and oxygen inlet arrangement of FIG. 11.
Figure 13:
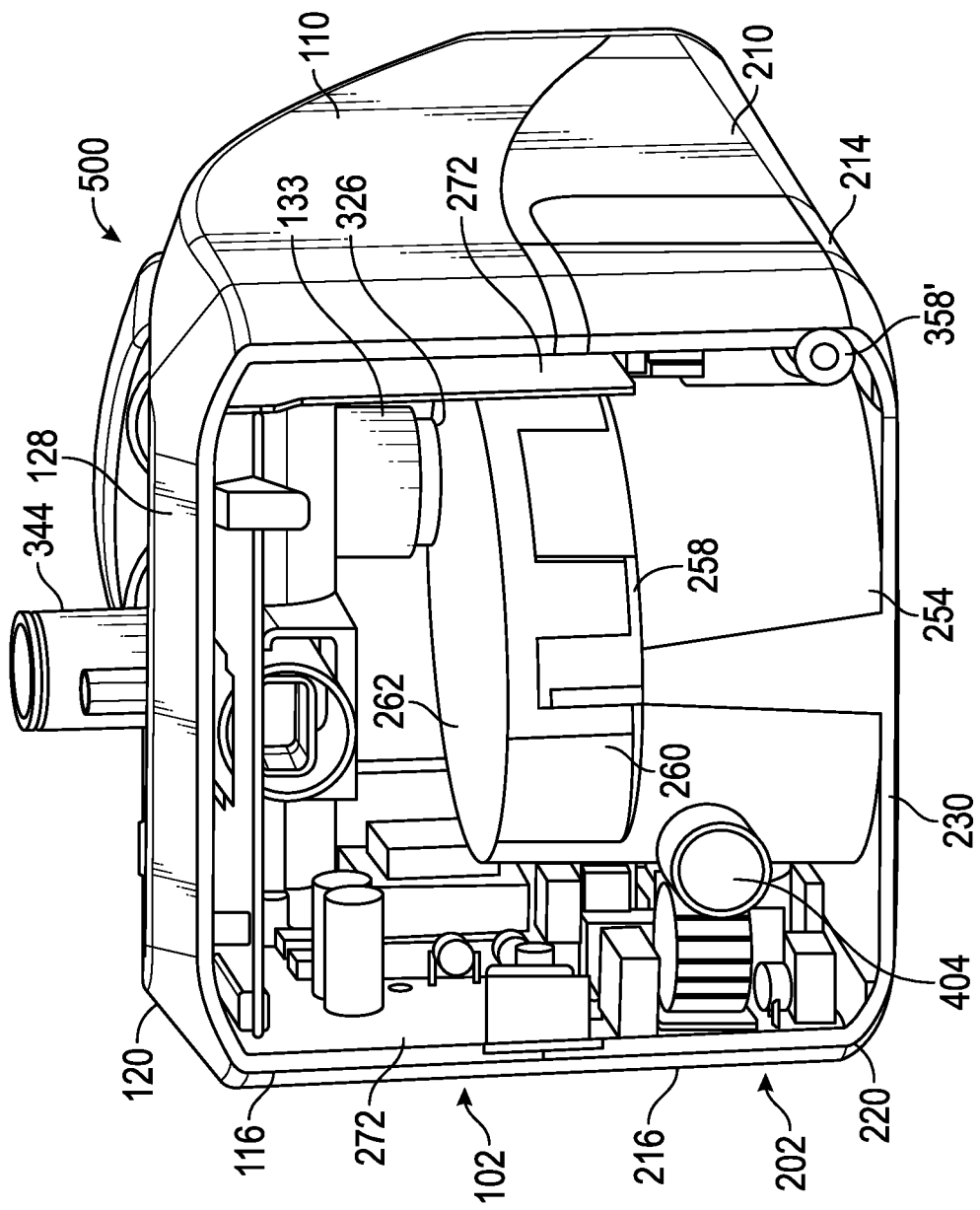
FIG. 13 is another transverse sectional view showing further detail of the air and oxygen inlet arrangement of FIG. 11.
Figure 14:
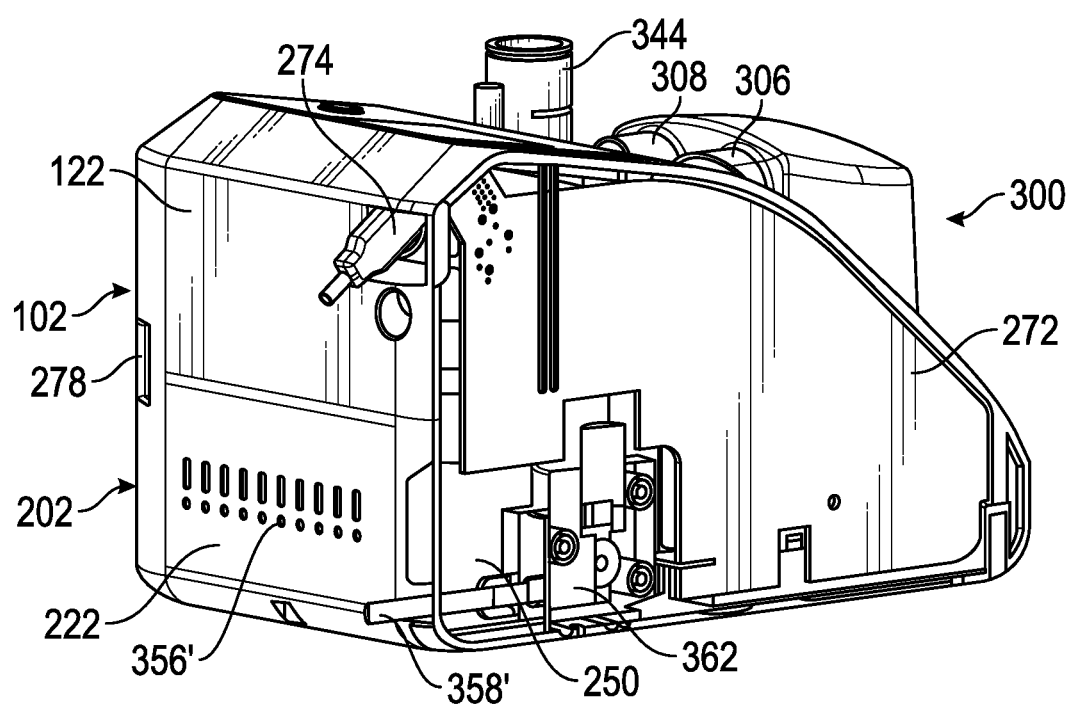
FIG. 14 is a longitudinal sectional view showing further detail of the air and oxygen inlet arrangement of FIG. 11.

The respiratory device can have air and oxygen (or alternative auxiliary gas) inlets in fluid communication with the motor to enable the motor to deliver air, oxygen (or alternative auxiliary gas), or a mixture thereof to the humidification chamber 300 and thereby to the patient. As shown in FIG. 10, the device can have a combined air/oxygen (or alternative auxiliary gas) inlet arrangement 350. This arrangement can include a combined air/oxygen port 352 into the housing 100, a filter 354, and a cover 356 with a hinge 358. A gases tube can also optionally extend laterally or in another appropriate direction and be in fluid communication with an oxygen (or alternative auxiliary gas) source. The port 352 can be fluidly coupled with the motor 402. For example, the port 352 may be coupled with the motor/sensor module 400 via a gases flow passage between the port 352 and an inlet aperture or port in the motor and/or sensor module 400, which in turn would lead to the motor.

The device can have the arrangement shown in FIGS. 11 to 14 to enable the motor to deliver air, oxygen (or alternative auxiliary gas), or a suitable mixture thereof to the humidification chamber 300 and thereby to the patient. This arrangement can include an air inlet 356' in the rear wall 222 of the lower chassis 202 of the housing 100. The air inlet 356' comprises a rigid plate with a suitable grill arrangement of apertures and/or slots. Sound dampening foam may be provided adjacent the plate on the interior side of the plate. An air filter box 354' can be positioned adjacent the air inlet 356' internally in the main housing 100, and include an air outlet port 360 to deliver filtered air to the motor via an air inlet port 404 in the motor/sensor module 400. The air filter box 354' may include a filter configured to remove particulates (e.g. dust) and/or pathogens (e.g. viruses or bacteria) from the gases flow. A soft seal such as an O-ring seal can be provided between the air outlet port 360 and air inlet port 404 to seal between the components. The device can include a separate oxygen inlet port 358' positioned adjacent one side of the housing 100 at a rear end thereof, the oxygen port 358' for receipt of oxygen from an oxygen source such as a tank or source of piped oxygen. The oxygen inlet port 358' is in fluid communication with a valve 362. The valve 362 can suitably be a solenoid valve that enables the control of the amount of oxygen that is added to the gases flow that is delivered to the humidification chamber 300. The oxygen port 358' and valve 362 may be used with other auxiliary gases to control the addition of other auxiliary gases to the gases flow. The other auxiliary gases can include any one or more of a number of gases useful for gas therapy, including but not limited to heliox and nitric oxide.

As shown in FIGS. 13 to 16, the lower housing chassis 202 can include suitable electronics boards 272, such as sensing circuit boards. The electronics boards can be positioned adjacent respective outer side walls 210, 216 of the lower housing chassis 202. The electronics boards 272 can contain, or can be in electrical communication with, suitable electrical or electronics components, such as but not limited to microprocessors, capacitors, resistors, diodes, operational amplifiers, comparators, and switches. Sensors can be used with the electronic boards 272. Components of the electronics boards 272 (such as but not limited to one or more microprocessors) can act as the controller 13 of the apparatus.

One or both of the electronics boards 272 can be in electrical communication with the electrical components of the apparatus 10, including the display unit and user interface 14, motor, valve 362, and the heater plate 140 to operate the motor to provide the desired flow rate of gases, operate the humidification chamber 12 to humidify and heat the gases flow to an appropriate level, and supply appropriate quantities of oxygen (or quantities of an alternative auxiliary gas) to the gases flow.

The electronics boards 272 can be in electrical communication with a connector arrangement 274 projecting from the rear wall 122 of the upper housing chassis 102. The connector arrangement 274 may be coupled to an alarm, pulse oximetry port, and/or other suitable accessories. The electronics boards 272 can also be in electrical communication with an electrical connector 276 that can also be provided in the rear wall 122 of the upper housing chassis 102 to provide mains or battery power to the components of the device.

As mentioned above, operation sensors, such as flow, temperature, humidity, and/or pressure sensors can be placed in various locations in the respiratory device, the patient conduit 16, and/or cannula 17. The electronics boards 272 can be in electrical communication with those sensors. Output from the sensors can be received by the controller 13, to assist the controller 13 to operate the respiratory system 10 in a manner that provides optimal therapy, including meeting inspiratory demand.

As outlined above, the electronics boards 272 and other electrical and electronic components can be pneumatically isolated from the gases flow path to improve safety. The sealing also prevents water ingress.

Control System

Figure 19A:
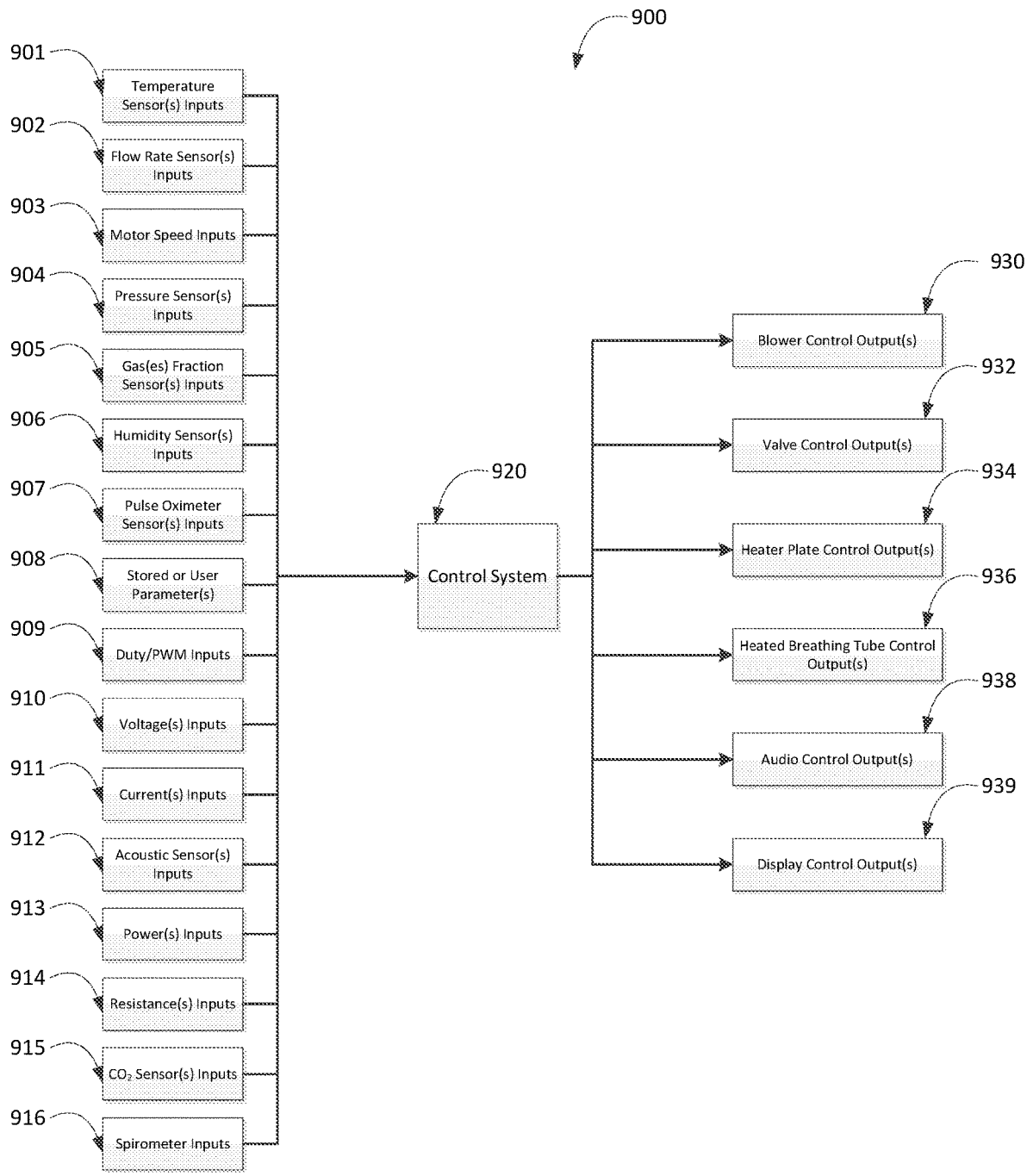
FIG. 19A illustrates a block diagram of a control system interacting with and/or providing control and direction to components of a respiratory system.

FIG. 19A illustrates a block diagram 900 of an example control system 920 that can detect patient conditions and control operation of the respiratory system including the gas source. The control system 920 can manage a flow rate of the gas flowing through the respiratory system as it is delivered to a patient. For example, the control system 920 can increase or decrease the flow rate by controlling an output of a motor speed of the blower (hereinafter also referred to as a "blower motor") 930 or an output of a valve 932 in a blender. The control system 920 can automatically determine a set value or a personalized value of the flow rate for a particular patient as discussed below. The flow rate can be optimized by the control system 920 to improve patient comfort and therapy.

The control system 920 can also generate audio and/or display/visual outputs 938, 939. For example, the flow therapy apparatus can include a display and/or a speaker. The display can indicate to the physicians any warnings or alarms generated by the control system 920. The display can also indicate control parameters that can be adjusted by the physicians. For example, the control system 920 can automatically recommend a flow rate for a particular patient. The control system 920 can also determine a respiratory state of the patient, including but not limited to generating a respiratory rate of the patient, and send it to the display, which will be described in greater detail below.

The control system 920 can change heater control outputs to control one or more of the heating elements (for example, to maintain a temperature set point of the gas delivered to the patient). The control system 920 can also change the operation or duty cycle of the heating elements. The heater control outputs can include heater plate control output(s) 934 and heated breathing tube control output(s) 936.

The control system 920 can determine the outputs 930-939 based on one or more received inputs 901-916. The inputs 901-916 can correspond to sensor measurements received automatically by the controller 600 (shown in FIG. 19B). The control system 920 can receive sensor inputs including but not limited to temperature sensor(s) inputs 901, flow rate sensor(s) inputs 902, motor speed inputs 903, pressure sensor(s) inputs 904, gas(es) fraction sensor(s) inputs 905, humidity sensor(s) inputs 906, pulse oximeter (for example, SpO$_2$) sensor(s) inputs 907, stored or user parameter(s) 908, duty cycle or pulse width modulation (PWM) inputs 909, voltage(s) inputs 910, current(s) inputs 911, acoustic sensor(s) inputs 912, power(s) inputs 913, resistance(s) inputs 914, CO$_2$ sensor(s) inputs 915, and/or spirometer inputs 916. The control system 920 can receive inputs from the user or stored parameter values in a memory 624 (shown in FIG. 19B). The control system 920 can dynamically adjust flow rate for a patient over the time of their therapy. The control system 920 can continuously detect system parameters and patient parameters. A person of ordinary skill in the art will appreciate based on the disclosure herein that any other suitable inputs and/or outputs can be used with the control system 920.

Controller

Figure 19B:
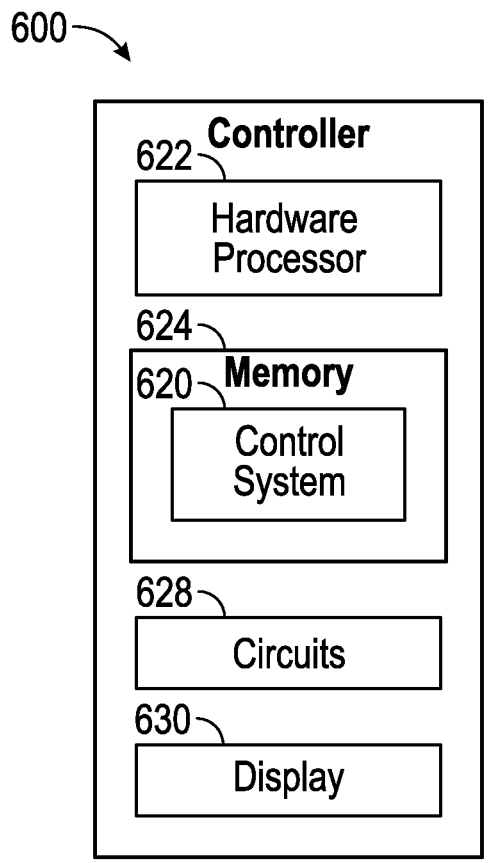
FIG. 19B illustrates a block diagram of an example controller.

FIG. 19B illustrates a block diagram of an embodiment of a controller 600. The controller 600 can include programming instructions for detection of input conditions and control of output conditions. The programming instructions can be stored in the memory 624 of the controller 600. The programming instructions can correspond to the methods, processes and functions described herein. The programming instructions can be executed by one or more hardware processors 622 of the controller 600. The programming instructions can be implemented in C, C++, JAVA, or any other suitable programming languages. Some or all of the portions of the programming instructions can be implemented in application specific circuitry 628 such as ASICs and FPGAs.

The controller 600 can also include circuits 628 for receiving sensor signals. The controller 600 can further include a display 630 for transmitting status of the patient and the respiratory assistance system. The display 630 can also show warnings and/or other alerts. The display 630 can be configured to display characteristics of sensed gas(es) in real time or otherwise. The controller 600 can also receive user inputs via the user interface such as display 630. The user interface can include button(s) and/or dial(s). The user interface can comprise a touch screen.

Motor and/or Sensor Module

Any of the features of the respiratory system described herein, including but not limited to the humidification chamber, the flow generator, the user interface, the controller, and the patient breathing conduit configured to couple the gases flow outlet of the respiratory system to the patient interface, can be combined with any of the sensor modules described herein.

Figure 20:
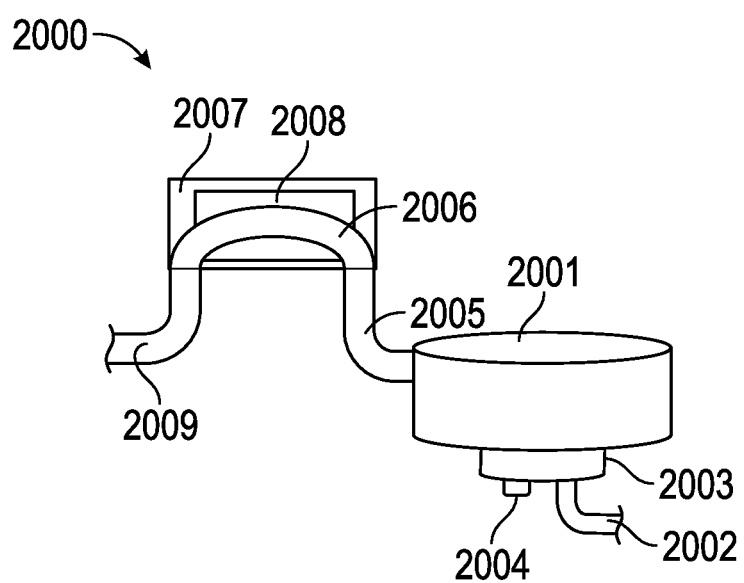
FIG. 20 illustrates a block diagram of a motor and/or sensor module.

FIG. 20 illustrates a block diagram of the motor and/or sensor module 2000, which can be received by the recess 250 in the respiratory device (shown in FIGS. 17 and 18). The motor and/or sensor module can include a blower 2001, which entrains room air to deliver to a patient. The blower 2001 can be a centrifugal blower.

One or more sensors (for example, Hall-effect sensors) may be used to measure a motor speed of the blower motor. The blower motor may comprise a brushless DC motor, from which motor speed can be measured without the use of separate sensors. For example, during operation of a brushless DC motor, back-EMF can be measured from the non-energized windings of the motor, from which a motor position can be determined, which can in turn be used to calculate a motor speed. In addition, a motor driver may be used to measure motor current, which can be used with the measured motor speed to calculate a motor torque. The blower motor may comprise a low inertia motor.

Room air can enter a room air inlet 2002, which enters the blower 2001 through an inlet port 2003. The inlet port 2003 can include a valve 2004 through which a pressurized gas may enter the blower 2001. The valve 2004 can control a flow of oxygen into the blower 2001. The valve 2004 can be any type of valve, including a proportional valve or a binary valve. In some embodiments, the inlet port does not include a valve.

The blower 2001 can operate at a motor speed of greater than 1,000 RPM and less than 30,000 RPM, greater than 2,000 RPM and less than 21,000 RPM, or between any of the foregoing values. Operation of the blower 2001 mixes the gases entering the blower 2001 through the inlet port 2003. Using the blower 2001 as the mixer can decrease the pressure drop that would otherwise occur in a system with a separate mixer, such as a static mixer comprising baffles, because mixing requires energy.

The mixed air can exit the blower 2001 through a conduit 2005 and enters the flow path 2006 in the sensor chamber 2007. A sensing circuit board with sensors 2008 can positioned in the sensor chamber 2007 such that the sensing circuit board is at least partially immersed in the gases flow. At least some of the sensors 2008 on the sensing circuit board can be positioned within the gases flow to measure gas properties within the flow. After passing through the flow path 2006 in the sensor chamber 2007, the gases can exit 2009 to the humidification chamber.

Positioning sensors 2008 downstream of the combined blower and mixer 2001 can increase accuracy of measurements, such as the measurement of gases fraction concentration, including oxygen concentration, over systems that position the sensors upstream of the blower and/or the mixer. Such a positioning can give a repeatable flow profile. Further, positioning the sensors downstream of the combined blower and mixer avoids the pressure drop that would otherwise occur, as where sensing occurs prior to the blower, a separate mixer, such as a static mixer with baffles, is required between the inlet and the sensing system. The mixer can introduce a pressure drop across the mixer. Positioning the sensing after the blower can allow the blower to be a mixer, and while a static mixer would lower pressure, in contrast, a blower increases pressure. Also, immersing at least part of the sensing circuit board and sensors 2008 in the flow path can increase the accuracy of measurements because the sensors being immersed in the flow means they are more likely to be subject to the same conditions, such as temperature and pressure, as the gases flow and therefore provide a better representation of the gases flow characteristics.

Figure 21:
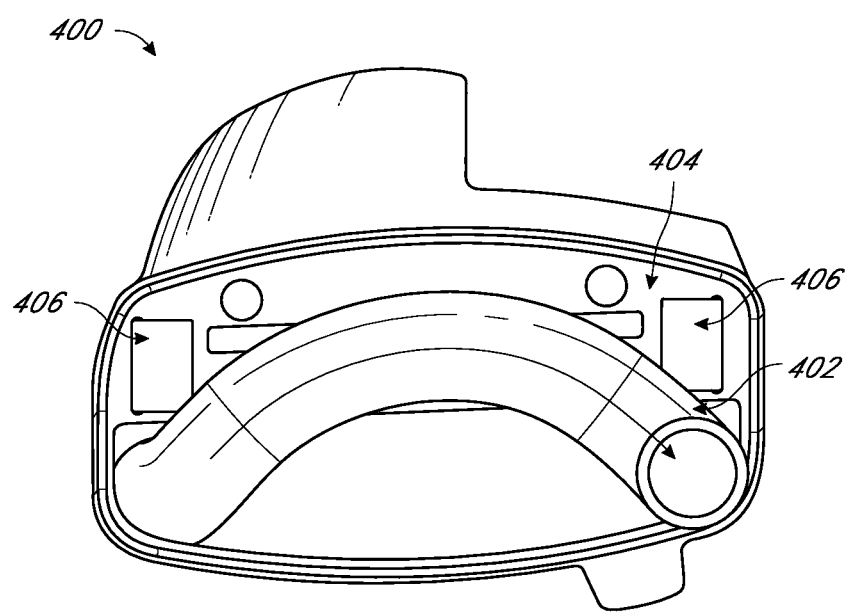
FIG. 21 illustrates a sensing chamber of an example motor and/or sensor module.

Turning to FIG. 21, the gases exiting the blower can enter a flow path 402 in the sensor chamber 400, which can be positioned within the motor and/or sensor module. The flow path 402 can have a curved shape. The flow path 402 can be configured to have a curved shape with no sharp turns. The flow path 402 can have curved ends with a straighter section between the curved ends. A curved flow path shape can reduce pressure drop in a gases flow without reducing the sensitivity of flow measurements by partially coinciding a measuring region with the flow path to form a measurement portion of the flow path, which will be described below with reference to FIGS. 23A-23B.

A sensing circuit board 404 with sensors, such as acoustic transmitters and/or receivers, humidity sensor, temperature sensor, thermistor, and the like, can be positioned in the sensor chamber 400 such that the sensing circuit board 404 is at least partially immersed in the flow path 402. Immersing at least part of the sensing circuit board and sensors in the flow path can increase the accuracy of measurements because the sensors immersed in the flow are more likely to be subject to the same conditions, such as temperature and pressure, as the gases flow, and therefore provide a better representation of the characteristics of the gases flow. After passing through the flow path 402 in the sensor chamber 400, the gases can exit to the humidification chamber.

The gases flow rate may be measured using at least two different types of sensors. The first type of sensor can comprise a thermistor, which can determine a flow rate by monitoring heat transfer between the gases flow and the thermistor. The thermistor flow sensor can run the thermistor at a constant target temperature within the flow when the gases flow around and past the thermistor. The sensor can measure an amount of power required to maintain the thermistor at the target temperature. The target temperature can be configured to be higher than a temperature of the gases flow, such that more power is required to maintain the thermistor at the target temperature at a higher flow rate.

The thermistor flow rate sensor can also maintain a plurality of (for example, two, three, or more) constant temperatures on a thermistor to avoid the difference between the target temperature and the gases flow temperature from being too small or too large. The plurality of different target temperatures can allow the thermistor flow rate sensor to be accurate across a large temperature range of the gases. For example, the thermistor circuit can be configured to be able to switch between two different target temperatures, such that the temperature of the gases flow will always fall within a certain range relative to one of the two target temperatures (for example, not too close but not too far). The thermistor circuit can be configured to operate at a first target temperature of about 50° C. to about 70° C., or about 66° C. The first target temperature can be associated with a desirable flow temperature range of between about 0° C. to about 60° C., or about 0° C. and about 40° C. The thermistor circuit can be configured to operate at a second target temperature of about 90° C. to about 110° C., or about 100° C. The second target temperature can be associated with a desirable flow temperature range of between about 20° C. to about 100° C., or about 30° C. and about 70° C.

The controller can be configured to adjust the thermistor circuit to change between at least the first and second target temperature modes by connecting or bypassing a resistor within the thermistor circuit. The thermistor circuit can be arranged as a Wheatstone bridge configuration comprising a first voltage divider arm and a second voltage divider arm. The thermistor can be located on one of the voltage divider arms. More details of a thermistor flow rate sensor are described in PCT Application No. PCT/NZ2017/050119, filed Sep. 3, 2017, which is Appendix A of the present disclosure and incorporated by reference herein in its entirety.

The second type of sensor can comprise an acoustic sensor assembly. Acoustic sensors including acoustic transmitters and/or receivers can be used to measure a time of flight of acoustic signals to determine gas velocity and/or composition, which can be used in flow therapy apparatuses. In one ultrasonic sensing (including ultrasonic transmitters and/or receivers) topology, a driver causes a first sensor, such as an ultrasonic transducer, to produce an ultrasonic pulse in a first direction. A second sensor, such as a second ultrasonic transducer, receives this pulse and provides a measurement of the time of flight of the pulse between the first and second ultrasonic transducers. Using this time of flight measurement, the speed of sound of the gases flow between the ultrasonic transducers can be calculated by a processor or controller of the respiratory system. The second sensor can transmit and the first sensor can receive a pulse in a second direction opposite the first direction to provide a second measurement of the time of flight, allowing characteristics of the gases flow, such as a flow rate or velocity, to be determined. In another acoustic sensing topology, acoustic pulses transmitted by an acoustic transmitter, such as an ultrasonic transducer, can be received by acoustic receivers, such as microphones. More details of an acoustic flow rate sensor are described in PCT application PCT/NZ2016/050193, filed Dec. 2, 2016, which is incorporated by reference herein in its entirety.

Readings from both the first and second types of sensors can be combined to determine a more accurate flow measurement. For example, a previously determined flow rate and one or more outputs from one of the types of sensor can be used to determine a predicted current flow rate. The predicted current flow rate can then be updated using one or more outputs from the other one of the first and second types of sensor, in order to calculate a final flow rate.

Frequency Analysis of Gases Flow Parameters

The present disclosure discloses processes for determining respiratory rates of a patient using a respiratory system, such as the ones described herein, by performing one or more frequency analyses of a signal from the gases flow. The signal from the gases flow can be one that varies with the patient's breathing. Examples of the signal can include flow rate, pressure, motor speed, power to motor, flow resistance, carbon dioxide data, humidity, variants thereof, and/or any combinations thereof. The processes described herein can utilize one or more of the sensors that are already present within the respiratory device. These sensors can be at least partially placed with in the gases flow path. The sensors can also be outside the gases flow path.

The frequency analysis can extract magnitude and frequency information from the available data, and therefore can be less likely to be in error because of an irregularity in the signal. The frequency analysis can provide more reliable respiratory rate data in a wide range of respiratory devices compared to measuring a breath cycle from the flow rate signal. The processes disclosed herein also focus on providing a more accurate measure of the patient's respiratory rate over a slightly longer time period than a quick and maybe inaccurate reading. The more accurate measurement of the patient's respiratory rate is more useful in allowing a clinician to make a judgement relating to the condition of the patient than a quick reading which may not be accurate.

The patient interface of the respiratory system that is in fluid connection with the flow generator can be a non-sealed interface, such as a nasal cannula. The processes described herein can overcome difficulties with measuring the respiratory rate in an unsealed system, which can have a larger amount of leak than a sealed system, such as with a face mask. The processes described herein can also be applied in respiratory systems with a patient interface that is a face mask, a nasal mask, a nasal pillows mask, an endotracheal tube, and/or a tracheostomy interface. The process described herein can be used with a nasal high flow system, a Continuous Positive Airway Pressure (CPAP) device, and/or a Bi-level Positive Airway Pressure device.

The frequency analysis can analyze fluctuations of the gases flow parameter from a control value. The fluctuations can be isolated by taking the difference between a measured value and an expected value. The expected value can be a target value, an average of previous values, or an expected value calculated based on other parameters (such as multiplying typical resistance of the circuit by motor speed to get an estimation of flow rate). The frequency analysis can also analyze the absolute value of the gases flow parameter by ignoring a magnitude in the frequency plane equal to the average value at a frequency of zero, which is the average value of the parameter rather than the respiratory rate. As will be described below, the magnitude at 0 Hz can also be removed.

The gases flow parameter used for determining the patient's respiratory rate can be calculated from any of the sensor signals described above. The gases flow parameter can be measured at any point along the gases flow path, anywhere from the entrance to the flow generator up to the patient interface. The gases flow parameter can be measured in a flow passage after the outlet of the flow generator. Measuring the gases flow parameter inside the respiratory device, as opposed to in the patient interface, can allow the sensor to be closer to the controller and/or avoid the need to replace the sensor with the patient interface. Measuring the gases flow parameter at the patient interface can result in larger and more easily measured fluctuations in the gases flow parameter from the patient breathing than inside the respiratory device.

The gases flow rate parameter can include the gases flow rate. When a patient is breathing while connected to the patient interface, the controller or one or more processors can obtain a signal indicative of the flow rate from the flow rate sensor. When the patient breathes in, a resistance to flow in the patient interface decreases and the flow rate increases. When the patient breathes out, the resistance to flow in the patient interface increases and the flow rate decreases. The controller can adjust the flow generator to achieve a target flow rate. However, because of the time lag between the flow rate variation due to the patient's breathing and the variation being canceled out, the breathing signal can still be detected in the flow rate signal.

The flow rate measurement analyzed for determining the respiratory rate can be the same flow rate measurement that is used to control the flow generator or a different flow rate measurement. The flow rate can be at least partially measured by an acoustic flow sensor and/or a thermistor flow sensor, which are described above. The thermistor flow sensor can have lower noise than the acoustic flow sensor while having a high enough sampling rate and being fast enough to produce flow rate readings for the processes described herein.

The respiratory device described herein can control the flow generator, such as the blower, based on the difference between a measured parameter and a target value for the parameter. The target value for the parameter can be constant or vary over time, such as to synchronize with the patient's breathing. As described above, the processes described herein can advantageously detect a breathing signal in a flow parameter, even when the device is attempting to hold the flow parameter constant.

The gases flow rate parameter can also include a gases flow pressure. The pressure sensor can be an absolute pressure sensor to measure an absolute pressure of the gases flow or a differential pressure sensor to measure a difference between an ambient pressure and the absolute gases flow pressure. The pressure measurement can also be a difference between the measurements of two absolute pressure sensors, one measuring the absolute gases flow pressure, and the other one measuring the ambient pressure.

Figure 22A:
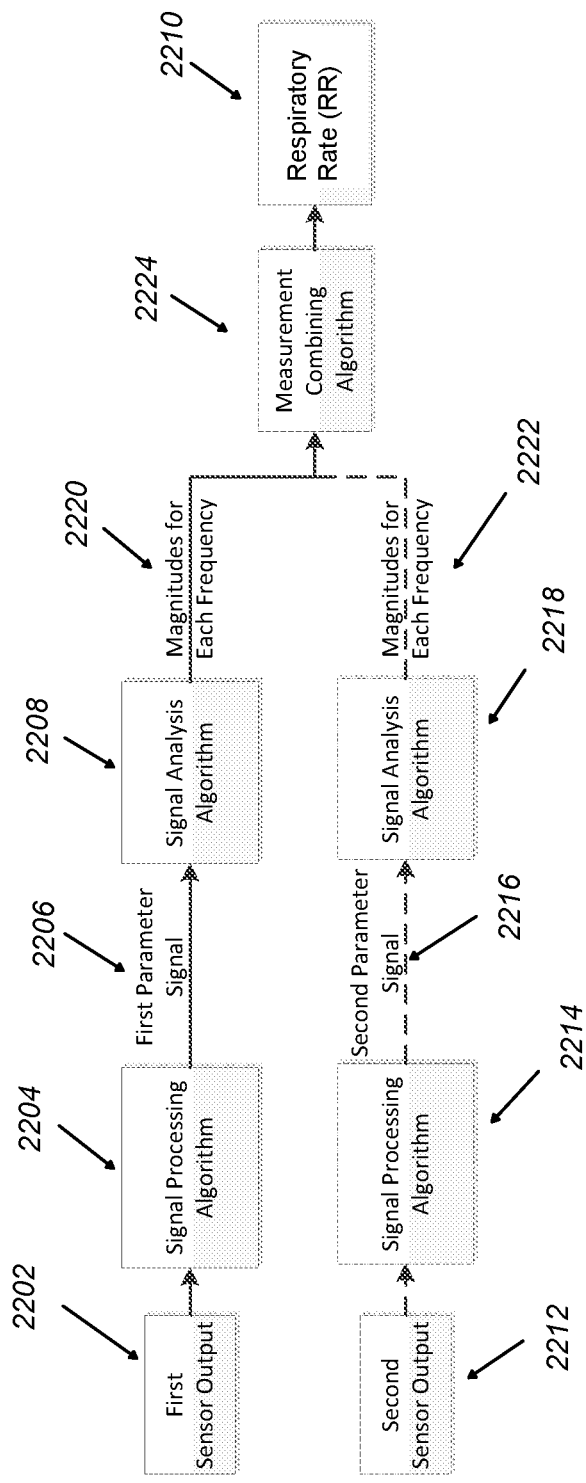
FIG. 22A illustrates an example block diagram for determining a respiratory rate from a gases flow parameter.

FIG. 22A illustrates an example process for determining the patient's respiratory rate by the frequency analysis. A sensor output 2202 from a sensor configured for measuring a gases flow parameter can be fed into a signal processing algorithm 2204. The sensor can be located in, at least partially in, or outside of the gases flow path. The gases flow parameter can vary with the patient's breathing. The gases flow parameter can be the flow rate, pressure, carbon dioxide data, or others. The controller or processor(s) can run the signal processing algorithm 2204 to process the signal output 2202 and measure the gases flow parameter. A gases flow parameter signal 2206 can be fed into a signal analysis algorithm 2008.

The signal analysis algorithm 2008 can comprise a frequency analysis for a discrete time series. The frequency analysis can include the discrete Fourier transform (DFT). The discrete Fourier transform takes discrete time series data and converts it into a complex number series which contains frequency, magnitude and phase information. The basic form of the DFT is:

$$X_k = \sum_{n=0}^{N-1} x_n \cdot e^{\frac{-i2\pi kn}{N}}$$

where $X_k$ is the output series of complex numbers, $x_n$ is the input series, and k is the frequency of interest. By squaring the real and imaginary parts of $X_k$ at each frequency, adding them together, and taking the square root, it is possible to extract the magnitude at each frequency. The magnitude represents the strength of the corresponding frequency in the evaluated time series.

The time between data points limits the resolution of the frequencies within the range. In order to be able to confidently detect a frequency within a data set, the sampling frequency has to be at least twice the frequency that is to be measured. This maximum detectable frequency should be at least as high as any frequency that may need to be detected. The processes described herein can require measuring patient breathing at least as high as 60 breaths per minute, or 1 Hz, which requires a sampling rate of at least 2 Hz, or 500 ms per sample. The processes described herein can require measuring patient breathing as high as 90 breaths per minute, or 1.5 Hz, which requires a sampling rate of 3 Hz, or 333 ms per sample. The processes described herein can require measuring patient breathing as high as 150 breaths per minute, or 4.5 Hz. The sampling rate can also be higher than twice the maximum detectable frequency that is to be measured in order to provide a buffer.

However, higher sampling rates are more computationally demanding. The sampling rate is further limited by the rate at which the sensor can deliver data. For example, if using the flow rate as the gases flow parameter, the thermistor sensor can deliver a data point as fast as every 14 ms, or at a frequency of 71.4 Hz.

To balance the need of confidence that the respiratory rate is detected and the need to prevent the sampling rate from being too high, the sampling rate of the signal analysis algorithm 2208 can be between about 14 ms (71.4 Hz) and about 500 ms (2 Hz), or between about 20 ms (50 Hz) and about 400 ms (2.5 Hz), or between about 25 ms (40 Hz) and about 333 ms (3 Hz), or between about 40 ms (25 Hz) and about 250 ms (4 Hz), or between about 50 ms (20 Hz) and about 200 ms (5 Hz), or about 100 ms (10 Hz).

A dominant frequency as determined by the signal analysis algorithm 2208 can be the respiratory rate from the output series. The dominant frequency is the frequency that results in the largest magnitude. As the patient breathing can result in the largest variation in the gases flow parameter than other factors that can affect the gases flow parameter, the dominant frequency can be assumed to be the respiratory rate. The exception to this is that, as described above, in configurations using an absolute value of the gases flow parameter instead of fluctuations from an average or target, the magnitude appearing at 0 Hz is ignored. The large magnitude at 0 Hz represents the average value of the gases flow parameter instead of the respiratory rate.

The frequency analysis can include a Goertzel algorithm, which can reduce the amount of computation of the signal analysis algorithm 2208 compared to the DFT. Parameters that can be chosen for the Goertzel algorithm can include, for example, maximum frequency, spacing between the discrete frequencies, and a decay constant (which will be described below).

The maximum frequency determines what frequencies are determined by the Goertzel algorithm. The patient's respiratory rate can fall within a defined range of possible frequencies. The Goertzel algorithm analyses the magnitude of a particular frequency, with a result that is equivalent to the square of the result of the DFT, but only for the frequency range defined by the algorithm 2208. In some configurations, the maximum frequency can be set to 60 min$^{-1}$, which can capture typical breathing rates of the patient, and can ignore higher frequencies (which typically may not be indicative of a patient's breathing). The maximum frequency can be adjusted for a different patient, such as 120 min$^{-1}$ for an infant.

The spacing between the frequencies determines how reliable the Goertzel algorithm is at capturing all frequencies between 0 and the maximum frequency. A smaller spacing makes the algorithm more reliable at capturing more frequencies. However, the computational costs increase as a greater number of frequencies are evaluated. A frequency spacing needs not be selected if a DFT is used, as the DFT can capture all frequency information, but the DFT comes at a significantly higher computational cost than the Goertzel algorithm. The required spacing is also dependent on the decay constant, as a longer decay period will result in less smoothing, which in turn requires a smaller spacing between the frequencies.

The spacing between the frequencies can be selected such that at least 70%, preferably at least 85%, of the energy is captured for any frequency between 0 and the maximum frequency. The Goertzel algorithm is advantageous as it is less computationally demanding than the DFT when a limited number of frequencies are being evaluated. For example, the algorithm 2208 can be assessed across a range from about 0.02 Hz to about 1.01 Hz at increments of about 0.01-0.03 Hz, or about 0.02 Hz. This range is the equivalent to between about 1.2 breaths per minute to 60.6 breaths per minute, which can capture a substantial portion of possible human respiratory rates, in increments of about 0.6 breathes per minute to about 1.8 breathes per minute, or about 1.2 breathes per minute. The Goertzel algorithm can also solve the problem described above of the large magnitude at 0 Hz, because 0 Hz is not sampled in the Goertzel algorithm. The Goertzel algorithm can further reduce computational requirements due to not calculating phase information for the various frequencies, which is not necessary for the purpose of determining the patient's respiratory rate.

The Goertzel algorithm works iteratively by calculating an intermediate variable for every frequency tested as each sample comes in using the formula:

$$s[n]=x[n]+2\cos(\omega_0)s[n-1]-s[n-2]$$

where s is the intermediate value, x is the signal, n is the sample number, and w is the angular frequency of interest that is being tested for.

Following the calculation of the intermediate variable, the magnitude of each frequency is evaluated using the formula:

$$y[n]=(s[n-2])^2+(s[n-1])^2-(2\cos(w_0)\cdot s[n-2]-s[n-1])$$

where y is the magnitude of the frequency of interest at sample n.

Figure 22B:
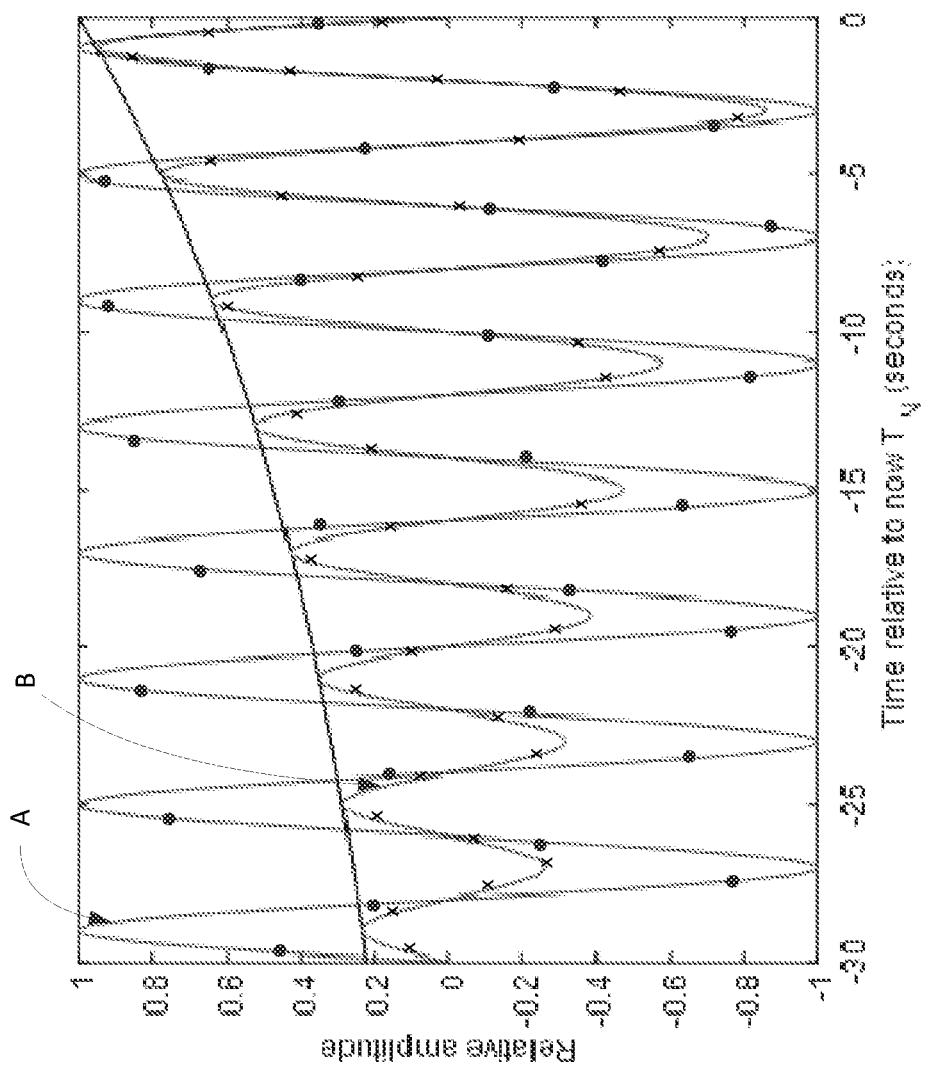
FIG. 22B illustrates an example effect of applying an exponential decay to gases flow parameter signal.

The signal analysis algorithm 2208 can further include applying an exponential decay to the parameter signal 2206 before the signal 2206 is evaluated using the Goertzel algorithm. FIG. 22B illustrates an example effect of applying an exponential decay to a gases flow parameter signal. Reference to the Goertzel algorithm in this disclosure can also include the modified Goertzel algorithm, which includes the application of the exponential decay. The exponential decay can be done by using the following two formulas prior to each iterative evaluation of the Goertzel algorithm.

$$s[n-1]=e^{-k^f \Delta t}s[n-1]$$

$$s[n-2]=e^{-k^f \Delta t}s[n-2]$$

where $\Delta t$ is the sampling time and $k^f$ is the decay constant. The decay constant for each evaluated frequency can be varied and can be based upon the number of samples required to determine if said frequency is present in the signal and/or other factors.

The exponential decay can prioritize the most recent samples and limit the sampled time of the Goertzel algorithm. The decay constant affects how quickly previous data is decayed away. A long decay period can indicate that the frequency estimates are more precise, however the estimates can take longer to change if the patient's respiratory rate changes. A short decay period can allow the frequency estimates to change more quickly, however the frequency estimate itself may be less accurate. The decay constant used in some configurations can provide a corner frequency of 3 breaths per minute.

Another advantage of the exponential decay is a smoothing effect of the results in the frequency domain, where the magnitude of each frequency present in the signal is spread to neighboring frequencies. This effect can be desirable when using a Goertzel algorithm, as occasionally a waveform in the data may be present at a frequency that is between two tested frequencies and can otherwise be missed. When smoothing the data, this waveform can be blurred into and/or detected at a neighboring frequency, increasing the likelihood of the Goertzel algorithm being able to accurately measure the patient's respiratory rate. However, smoothing the data can reduce the reliability of the frequency analysis. The exponential decay constant can be chosen to balance the data smoothing effect and the reliability of the frequency analysis.

An example effect of the exponential decay on the parameter signal is illustrated in FIG. 22B, wherein Line A represents an input frequency of 0.25 Hz, and Line B is the effective signal that is presented to the Goertzel algorithm after the exponential decay is applied.

Figure 23A:
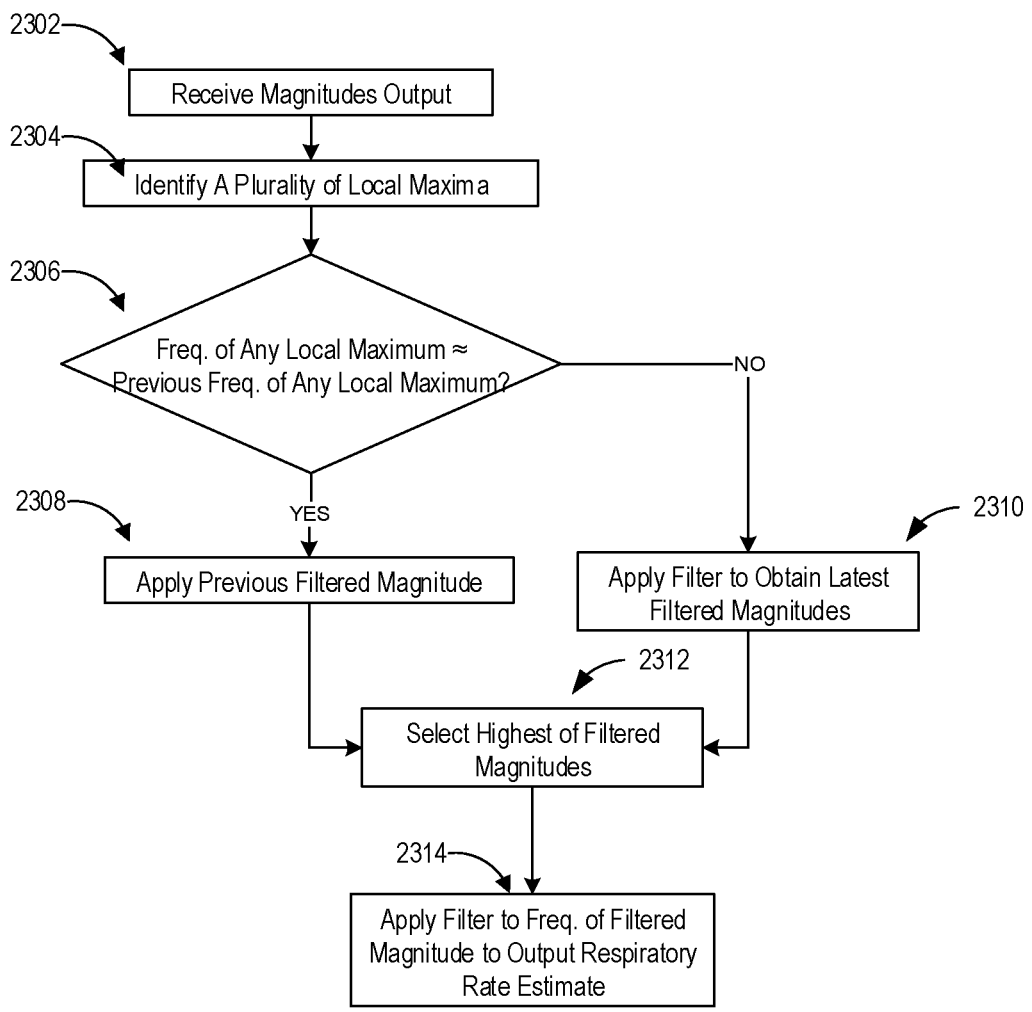
FIG. 23A illustrates an example flow chart of using outputs from a Goertzel algorithm to determine a respiratory rate estimate.

Returning to FIG. 22A, during the frequency analysis using the signal analysis algorithm 2208, the magnitudes of various frequencies are calculated from the data, which represents the strength of each frequency signal in the data. The dominant frequency, or the frequency that results in the largest magnitude, as determined by the algorithm 2208 is the respiratory rate 2210. As shown in FIG. 23A, in some configurations that implement the Goertzel algorithm, at each iteration of the algorithm, the controller can receive the magnitudes output from the algorithm at step 2302. At step 2304, the controller can identify local maxima of the magnitudes output by the Goertzel algorithm. The local maxima are defined as magnitudes that are greater than the magnitudes of neighboring frequencies, and which are a sufficient distance from any larger local maxima. The controller can identify two or more (such as two, three, four, five, six or more) of the largest local maxima at each iteration of the algorithm.

Following the identification of the local maxima, the controller can apply a filter to each of the magnitudes of the two or more local maxima. To apply the filter, at decision step 2306, the controller identifies whether the frequency of any one of the local maxima is close to the frequency of one of the two or more local maxima from the previous iteration. Each of the latest local maxima is compared individually with each of the previous local maxima to determine whether there is a match. If one of the local maxima is close to (such as being substantially the same as or within a predetermined distance from) one of the previous local maxima, the filter uses the previous filtered magnitude value of the previous local maximum and the magnitude of the latest local maximum when determining the filtered frequency of the latest local maximum at step 2308. The latest local maximum being close to the previous local maximum can indicate that the latest local maximum is caused by the same waveform as the previous local maxima. If one of the local maxima is not close to any one of the previous local maxima, the controller starts the filtered magnitude of the new local maximum at zero (that is, assuming a zero value for the filtered magnitude of the previous local maximum) and applies the filter to the latest local maximum to obtain the filtered magnitude for the local maximum at step 2310. When one of the local maxima is not close to any of the previous local maxima, it is assumed that the latest local maximum is caused by a new waveform.

Once the filtered magnitudes for all the latest local maxima have been determined, at step 2312, the controller selects the highest value of the two to five filtered magnitudes. The frequency associated with the highest filtered magnitude value is assumed to be the most indicative of the respiratory rate of the patient. Due to the filtering described above, this method can allow the controller to ignore short term high amplitude signals, as these are unlikely to correspond to the patient's breathing.

At step 2314, the controller can apply another filter to the chosen frequency above over time to give the filtered respiratory rate of the patient. At each iteration of the algorithm, the filtered respiratory rate is updated using the latest frequency. The filter at step 2314 can also weight frequency values by the magnitude of the frequency from the Goertzel algorithm, such that the estimation of respiratory rate is updated more quickly when the breathing signal is stronger.

The process can optionally include a second sensor input 2212 from a second sensor configured to monitor a second gases flow parameter. The second sensor can be located in, at least partially in, or outside of the gases flow path. The gases flow parameter and the second gases flow parameter can be the pressure and flow rate or others. The second sensor input 2212 can be fed into a signal processing algorithm 2214, which can have the same or similar features as the signal processing algorithm 2204. A second parameter signal 2216 obtained using the signal processing algorithm 2214 can be fed into a signal analysis algorithm 2218, which can have the same or similar features as the signal processing algorithm 2208.

Once the magnitudes 2220, 2222 for each frequency are determined for each gases flow parameter, the magnitudes 2220, 2222 at corresponding frequencies can be combined into a combined magnitude that indicates the strength of the frequency across the various gases flow parameters. Optionally, when adding the magnitudes together, the magnitudes for each gases flow parameter can be scaled to ensure proper weighting is given to each measurement. The magnitudes can be scaled by a pre-set amount, an average absolute value of a certain parameter, average frequency magnitude values for a certain parameter, and/or a maximum frequency magnitude value for a certain parameter. The process can optionally combine the magnitudes at corresponding frequencies across more than two gases flow parameters.

Example Data Preprocessing Stage

The signal processing algorithm 2204 can also include a preprocessing stage to assess and/or modify the gases flow parameter before outputting the first or second flow parameter signals 2206, 2216. The controller can implement the pre-processing stage prior to using the gases flow parameter to make a determination of patient attachment and/or a respiratory rate estimation. This stage may allow the controller to decide whether the gases flow parameter is suitable for use in determining patient attachment and/or respiratory rate, and/or to remove certain features from the flow parameters, such that the flow parameter signal that is fed into the signal analysis algorithm can be more representative of any effects the patient's respiration is having on the gases flow parameter (such as the flow rate, pressure, or otherwise).

Assessing Suitability of Data

Figure 23B:
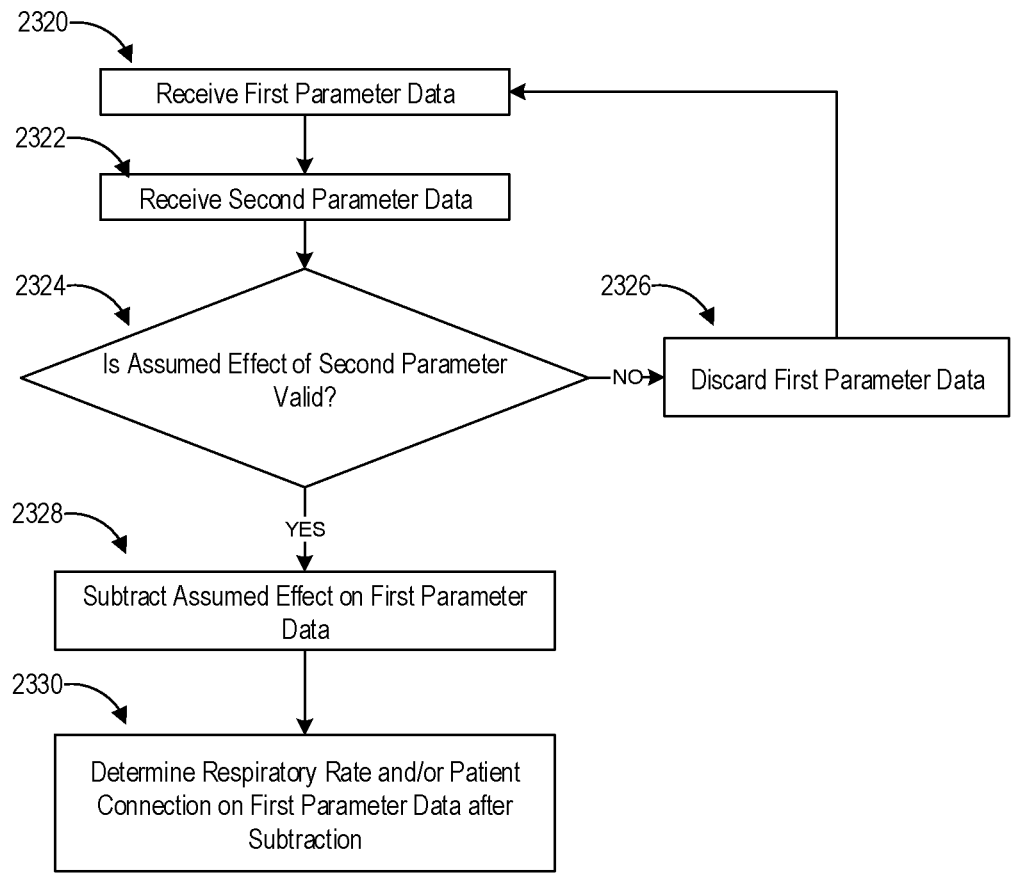
FIG. 23B illustrates an example flow chart of using flow parameter data to determine patient connection and/or respiratory rate.

The controller makes a determination of whether the flow parameter data is suitable for use in determining patient interface attachment and/or respiratory rate based on a number of factors. FIG. 23B illustrates an example process for such determination. The flow parameter can be flow rate. The flow parameter can also be pressure or other types of parameters disclosed herein, with slightly different equations than the equations applied to the flow rate data.

As shown in FIG. 23B, at step 2320, the controller can receive a first flow parameter data and at step 2322, the controller can receive a second flow parameter data that is of a different type than the first flow parameter data. The second parameter is assumed to have effects on the first parameter. For example, the motor speed and/or oxygen flow rate or concentration can have an effect on the gas flow rate that is separate from the effect of the patient's respiration on the gas flow rate. At decision step 2324, the controller can determine whether the assumed effect is valid. For example, the assumed effect can be valid if the assumed effect is greater than a minimum threshold. If the assumed effect is not valid, such as by being lower than the minimum threshold, it can be difficult to predict accurately the effect of the second parameter on the first parameter. At step 2326, the controller can discard the first parameter value and return to step 2320. If the assumed effect is valid, such as by being greater than the minimum threshold, the controller can subtract the assumed effect of the second parameter on the first parameter at step 2328. At step 2330, the controller can use the modified first parameter data to determine whether the patient is connected to the patient interface and/or estimate the respiratory rate of the patient.

Figure 23C:
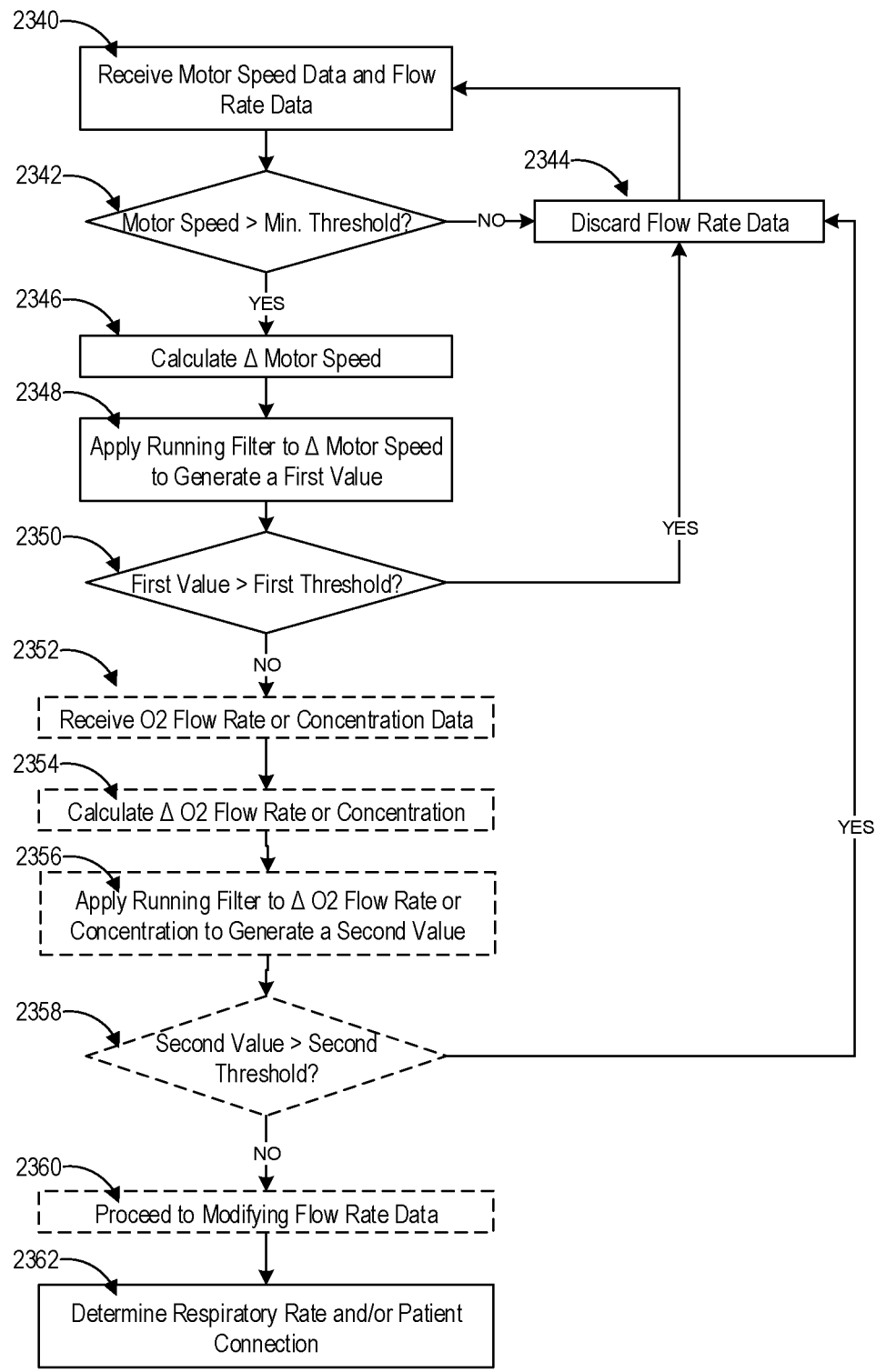
FIG. 23C illustrates an example flow chart of determining whether the flow parameter data is suitable for use in determining patient interface attachment and/or respiratory rate.

FIG. 23C illustrates an example of implementing the process of FIG. 23B. In the process of FIG. 23C, the first parameter can include the flow rate data and the second parameter(s) can include the motor speed, the oxygen flow rate, and/or the oxygen concentration. At step 2340, the controller can receive the motor speed data and the flow rate data. In order to identify the patient's respiration in the flow rate data, the motor needs to be operating at a sufficient speed. If the motor speed is too low, the effect of the motor speed on the flow rate may not be accurately predicted. Therefore, at step 2342, the controller can compare the motor speed to a minimum motor speed threshold. If the motor speed is below the threshold, at step 2344, the flow rate data is deemed to be unsuitable, and the flow rate data point is discarded.

If the motor speed is above the threshold, at step 2346, the controller calculates the recent changes in the motor speed. A change in motor speed can result in a change in the flow rate, which makes it more difficult to identify the patient's respiration in the flow rate data. While the effect of the motor speed can be removed from the flow rate data to some degree, larger changes in motor speed may make the data too unreliable for identifying the patient's respiration. Therefore, at step 2348, the controller can apply a running filter to the relative changes in motor speed in order to generate a first value representing the recent relative changes in motor speed. At decision step 2350, the controller can compare the first value with a first threshold. If the first value is above the first threshold, the controller deems the data to be unsuitable, and the flow data point is discarded at step 2344.

Figure 23D:
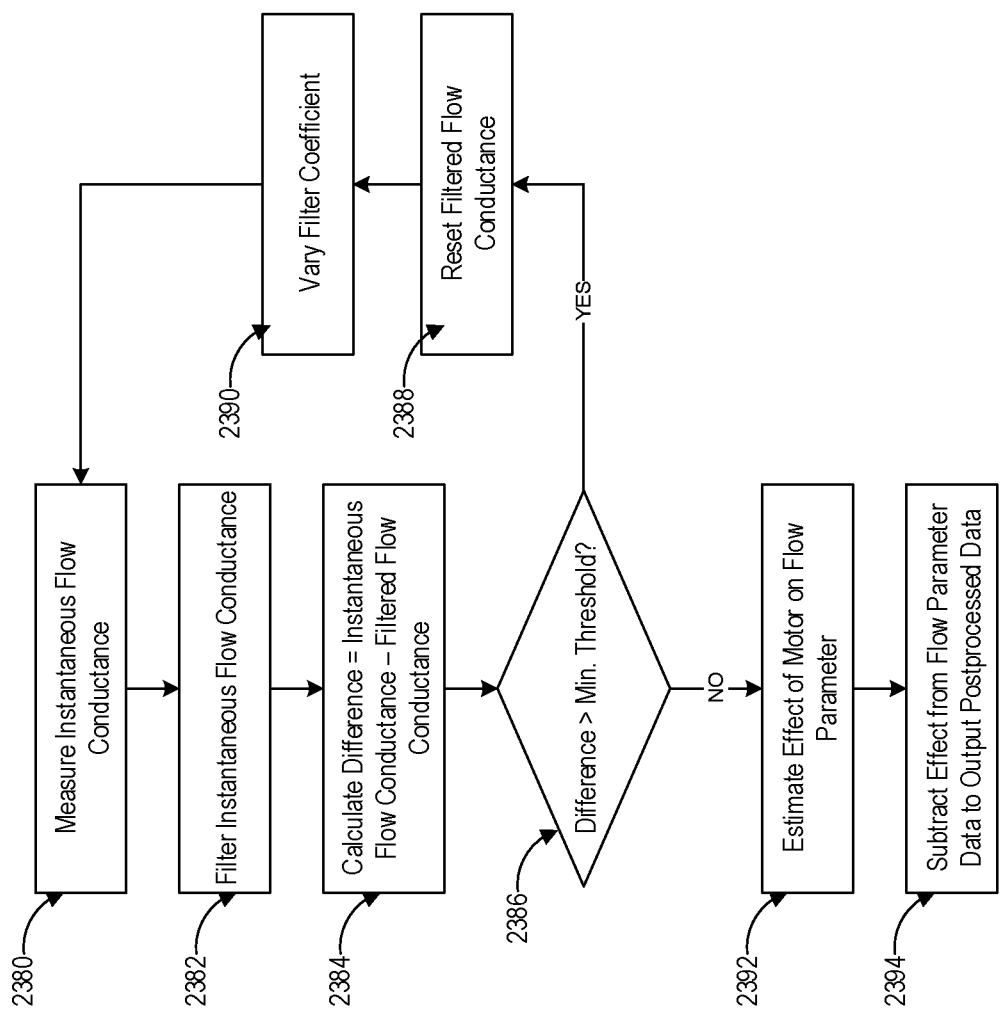
FIG. 23D illustrates an example flow chart of modifying flow rate data to remove assumed effects of motor speed.

The flow rate can also be affected by the flow rate or concentration of a supplementary gas from a supplementary gas source, such oxygen from a supplementary oxygen source. Although FIG. 23C is illustrated using oxygen as an example, the steps performed relating the flow rate or concentration of oxygen can also be performed on the flow rate or concentration of any other supplementary gas mixed with ambient air. At step 2352, the controller can optionally receive an oxygen flow rate data or an oxygen concentration data. At step 2354, the controller can optionally calculate the recent changes in the oxygen flow rate or the oxygen concentration. If the flow rate or concentration of oxygen changes, the resulting change in the total flow rate can make it more difficult to identify the patient's respiration in the flow rate signal. Therefore, at step 2356, the controller can optionally apply a running filter to the changes in oxygen concentration of the gas or the oxygen flow rate in order to generate a second value representing the recent changes in oxygen concentration or flow rate. At decision step 2358, the controller can optionally compare the second value with a second threshold. If the second value is above the second threshold, the controller can determine the flow rate data is unsuitable, and the flow data point can be discarded at step 2344. If the second value is below the threshold, at step 2360, the controller can optionally proceed to modify the flow rate data to remove the effect of the motor speed and/or oxygen concentration or flow rate on the flow rate data (such as shown in FIG. 23D). At step 2362, the controller can determine whether the patient is connected to the patient interface and/or estimate the respiratory rate of the patient using the flow rate data or modified flow rate data.

For the above determination, either oxygen concentration data or oxygen flow rate data can be used. Oxygen concentration data can be determined using one or more sensors in the respiratory device, such as ultrasonic sensors. Oxygen flow rate from the oxygen source can be determined by an oxygen flow rate sensor located downstream of the oxygen source.

Modifying Data

As described above, if the controller deems the data to be suitable, the flow date (or any other flow parameter data) can be modified to remove the effect of the motor (or other factors, such as the oxygen concentration or flow rate). Modifying the gases flow parameter can involve removing the assumed effect of other variables from the gases flow parameter (such as the motor speed). This assumed effect is only valid if the gases flow parameter data meets certain criteria. As described above, if these criteria are not met, the data may be discarded.

FIG. 23D illustrates an example process of modifying the flow rate data to remove the effect of motor speed. The effect of the motor can be estimated using the motor speed and the flow conductance. At step 2380, the controller can measure an instantaneous flow conductance. The flow conductance is approximately constant with time, and can therefore be estimated using a low pass filter. The controller measures the instantaneous flow conductance at each iteration using the current motor speed and the measured flow rate. At step 2382, the controller filters the instantaneous flow conductance in order to determine the filtered flow conductance.

At decision step 2384, the controller can compare the instantaneous flow conductance with the filtered flow conductance to see if the difference is significantly different. If the difference is significant, it is likely that something has changed the physical system, such as the cannula being attached or detached. The instantaneous flow conductance can be compared with the filtered flow conductance by taking the difference of the two variables and comparing it with a minimum threshold at decision step 2386. If the difference exceeds the threshold, the difference is considered to be significant, and the controller can reset the filtered flow conductance at step 2388. The reset can allow the device to quickly adjust its estimate of the flow conductance when the cannula has been attached and detached from the patient.

At step 2390, the controller can also vary the filter coefficient of the filtered flow conductance calculation based on the difference between the instantaneous flow conductance and the filtered flow conductance. This allows the filtered flow conductance to change more quickly when the variance of the flow conductance is high, such as when the cannula has first been attached. The controller can then return to step 2380 to start a new iteration of the process.

If the difference does not exceed the threshold, the difference is considered to be not significant, and the controller can estimate the effect of the motor on the flow rate at step 2392. The controller can output a value of the effect using the filtered flow conductance and the motor speed. At step 2394, the value can be subtracted or otherwise removed from the flow rate data to give the post-processed flow rate data. The post-processed flow rate data can be more indicative of the patient's respiratory flow (although the post-processed flow rate data can still include signal noise).

The controller can also track the recent changes in the flow conductance. The changes can be tracked by adding the difference between the last two instantaneous flow conductance values to a running total, which is then decayed over time. The decayed running total is filtered to obtain the filtered recent changes in flow conductivity. The filtered recent changes in flow conductivity can be used in further parts of the frequency analysis algorithm along with the post-processed flow rate data.

Example Frequency Analysis Processes Using a Measure of Variation

Figure 24A:
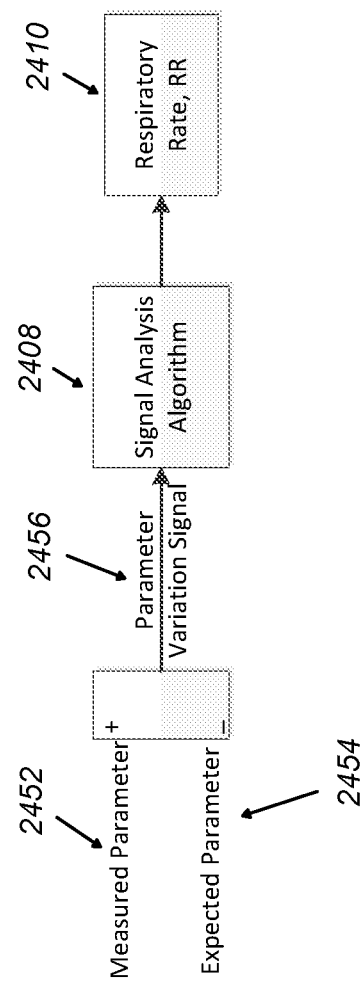
FIGS. 24A-24B illustrate example block diagrams for determining a respiratory rate using a parameter variation signal.
Figure 24B:
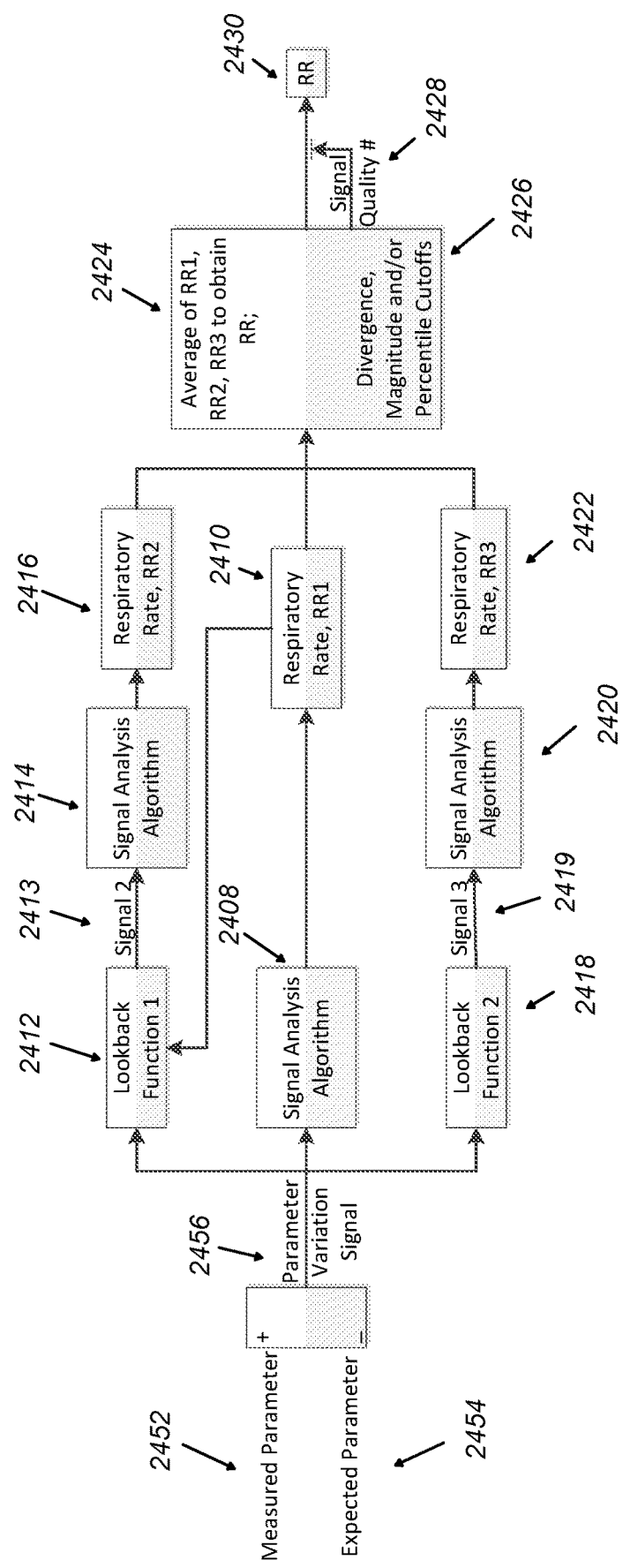

FIGS. 24A and 24B illustrate processes of respiratory rate determination by performing frequency analysis on a parameter variation signal 2456. Features of the processes in FIGS. 22, 24A, and 24B can be incorporated into one another. The parameter variation signal can be derived from a difference between a measured parameter value 2452 and an expected parameter value 2454. The expected parameter value can be a target value, a value determined based on measurements of other parameters, and/or others. The parameter can include flow rate, pressure, flow resistance of the breathing circuit, motor speed, or others. The flow rate, pressure, and/or motor speed can be measured by one or more sensors and/or from other parameters, as described above. The flow resistance can be calculated from the flow rate and one of the pressure or motor speed. A low pass filter can be applied to the flow resistance value calculated based on the flow rate and one of the pressure or motor speed, such as a moving average, Butterworth filter, Kalman filter, or extended Kalman filter.

The parameter variation signal 2456 can include the difference between the measured flow rate and the target flow rate, or between the measured flow rate and the product of the measured flow resistance and the measured motor speed, or between the measured pressure and the expected pressure, or between the measured flow resistance and the expected flow resistance, or between the measured motor speed and the expected motor speed, or between the measured flow rate and a function of the measured flow resistance and the measured motor speed, or between the measured pressure and a function of the measured flow resistance based on the measured pressure and the measured motor speed.

The parameter variation signal 2456 can be fed into a signal analysis algorithm 2408. The signal analysis algorithm 2408 can comprise any of the frequency analysis algorithms as described above, such as the Goertzel algorithm. In FIG. 24A, the controller can output the first respiratory rate 2410 as determined from the signal analysis algorithm 2408 as the patient's respiratory rate.

Figure 24C:
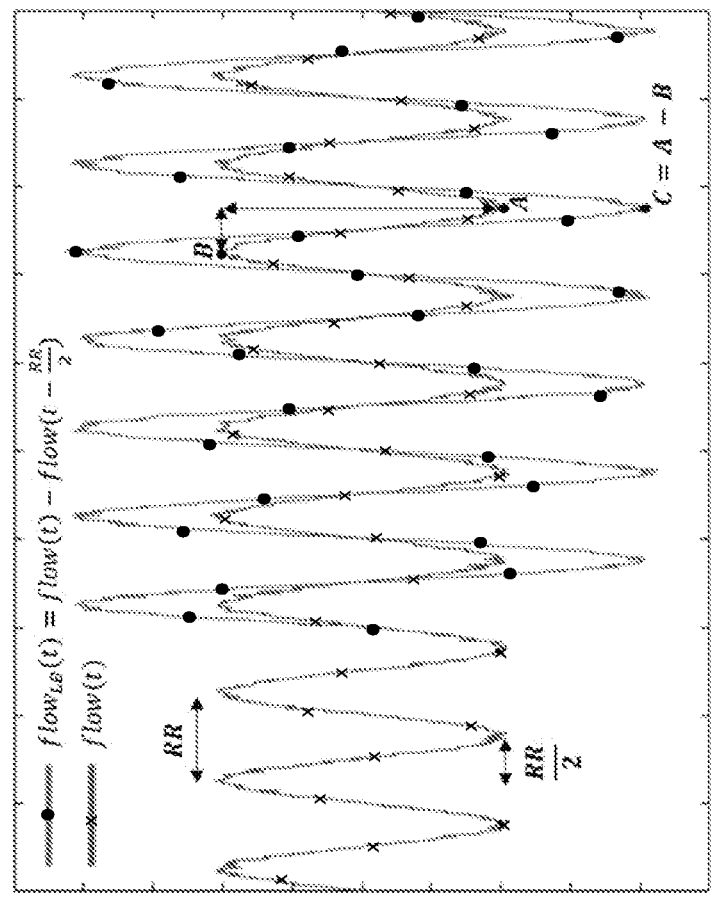
FIG. 24C illustrates an example application of a lookback function.
Figure 24D:
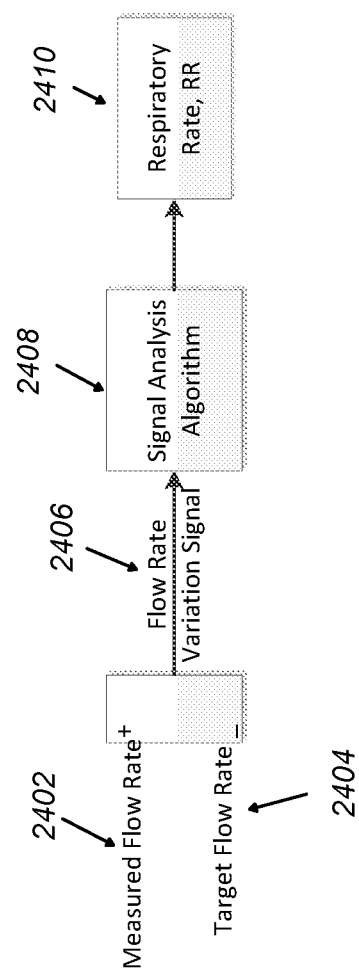
FIGS. 24D-E illustrate example block diagrams for determining a respiratory rate using a flow rate variation signal.
Figure 24E:
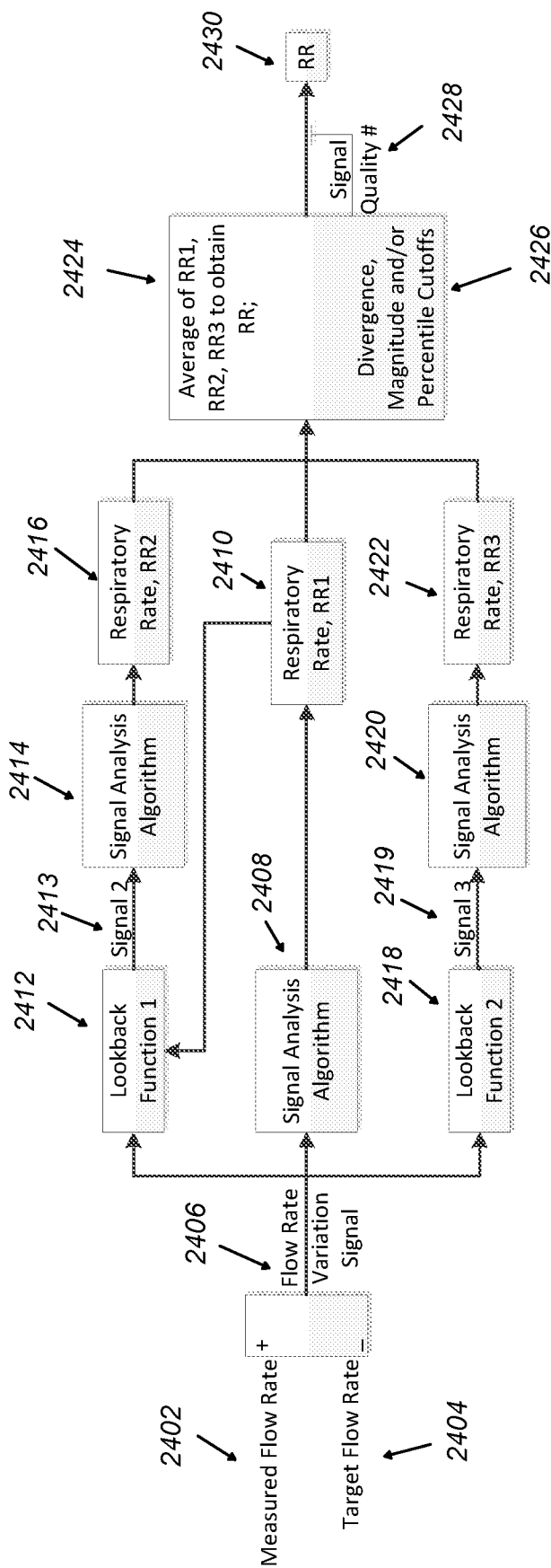

FIGS. 24D and 24E illustrate the processes of determining a patient's respiratory rate as shown in FIGS. 24A and 24B respectively, using the flow rate values. Features of the processes in FIGS. 22, 24A, 24B, and 24C-D can be incorporated into one another. The flow rate can be analyzed while controlling to the flow generator to attempt to achieve a target flow rate. The signal that is fed into a signal analysis algorithm 2408 can be a flow rate variation signal 2406. The flow rate variation signal 2406 can be the difference between the measured flow rate 2402 and the target flow rate 2404. The measured flow rate can be a flow rate measured by any of the flow rate sensors disclosed herein, such as the thermistor flow sensor. The signal analysis algorithm 2408 can be any of the frequency analyses as described above, such as the Goertzel algorithm, can output the first respiratory rate 2410 as determined from the signal analyzing algorithm 2408 as the patient's respiratory rate. In FIG. 24D, the first respiratory rate 2410 can be outputted as the patient's respiratory rate.

In FIG. 24B, a plurality of frequency analyses can be run. The plurality of frequency analyses can be the same or similar as, or different than the signal analysis algorithm 2408. In addition to running the signal analysis algorithm 2408 on the parameter variation signal 2456 to determine the first respiratory rate 2410, the first respiratory rate 2410 can be used to determine a lookback period of a first lookback function 2412. The first lookback function 2412 can be run on the parameter variation signal 2456 to obtain a second signal 2413. A lookback function can subtract the parameter variation signal 2456 of a lookback period prior from the current parameter variation signal 2456. For example, as shown in FIG. 24C, when the parameter of interest is flow rate and the lookback period is half of a breath cycle period, the lookback function can subtract a previous flow rate variation signal B from a current flow rate variation signal A. As shown in FIG. 24C, when the lookback period is half the breath cycle period, the value of the parameter variation signal from half a breath cycle prior can be the conjugate of the current value. If the estimation of the first respiratory rate 2410 was correct, taking the difference of these values (C=A−B) can double the magnitude of the breath cycle waveform. If the estimation of the first respiratory rate 2410 was incorrect, a non-complementary portion of the signal B can be subtracted from the signal A. The resulting data set can be even less clear for the purpose of determining respiratory rate.

A signal analysis algorithm 2414 can be run on the second signal 2413 in order to determine a second respiratory rate 2416. Running the lookback function leading to a separate signal analysis algorithm, such as another Goertzel algorithm, can identify events that may otherwise lead to inaccurate respiratory rate determination from a single Goertzel algorithm Examples of the events can include one or more nasal prongs being blocked, which can result in a large DC term in the flow rate variation signal. The DC term can be removed when using a subtracting method.

If the estimation of the first respiratory rate 2410 was correct, a same or similar second respiratory rate 2416 can be observed when running the signal analysis algorithm 2414 on the second signal 2413, with differences in the magnitude. The effect of likely increased signal noise may not have a significant effect on the respiratory rate determination on the second signal. The absolute value of the signal noise may increase, but because the breath waveform may double, the relative signal noise may decrease.

If the estimation of the first respiratory rate was incorrect, a non-complementary portion of the parameter variation signal 2456 can be subtracted from the second signal 2413. The resulting data set can be even less clear for the purpose of determining respiratory rate. The second respiratory rate 2416 determined from this data can be different from the first respiratory rate 2410, indicating that the first respiratory rate 2410 is incorrect.

The signal analysis algorithm 2414 can also optionally be run on a combination, which can be a sum or addition of the parameter variation signal 2456 and the second signal 2413, for example, when the lookback period of the first lookback function 2412 is a full breath period. The current value of the parameter is the same as the value of the parameter from the lookback function. However, this addition method may not be able to remove certain artefacts in the parameter variation signal 2456 that can be removed by the subtraction method. Any DC terms still remaining in the parameter variation signal can be doubled by the addition method, whereas the subtraction method can remove the DC terms.

A second lookback function 2418 can also be run on the parameter variation signal 2456 to obtain a third signal 2419. The second lookback function 2418 can have a constant lookback period. The lookback period can be smaller than the full breath period. A short lookback period can allow more recent data to be analyzed, and reduce the inaccuracy in the single signal analyzing algorithm when the respiratory rate changes. Subtracting the parameter variation signal 2456 of a short lookback period prior from the current parameter variation signal 2456 can remove artefacts, such as from the motor control. The resulting data set in the third signal 2419 can be effectively the first derivative of the measured parameter. Another signal analysis algorithm 2420 can be run on the third signal 2419 to determine a third respiratory rate 2422, which can be similar to the first respiratory rate 2410 under normal breathing conditions.

In FIG. 24D, a plurality of frequency analyses can be run. The plurality of frequency analyses can be the same or similar as, or different than the signal analysis algorithm 2408. In addition to running the signal analysis algorithm 2408 on the flow rate variation signal 2406 to determine the first respiratory rate 2410, the first respiratory rate 2410 can be used to determine a lookback period of a first lookback function 2412. The first lookback function 2412 can be run on the flow rate variation signal 2406 to obtain a second signal 2413. A lookback function can subtract the flow rate variation signal 2406 of a lookback period prior from the current flow rate variation signal 2406.

A signal analysis algorithm 2414 can be run on the second signal 2413 in order to determine a second respiratory rate 2416. Running the lookback function leading to a separate signal analysis algorithm, such as another Goertzel algorithm, can identify events that may otherwise lead to inaccurate respiratory rate determination from a single Goertzel algorithm. Examples of the events can include one or more nasal prongs being blocked, which can result in a large DC term in the flow rate variation signal. The DC term can be removed when using a subtracting method.

If the estimation of the first respiratory rate 2410 was correct, a same or similar second respiratory rate 2416 can be observed when running the signal analysis algorithm 2414 on the second signal 2413, with differences in the magnitude. The effect of likely increased signal noise may not have a significant effect on the respiratory rate determination on the second signal.

If the estimation of the first respiratory rate was incorrect, a non-complementary portion of the flow rate variation signal 2406 can be subtracted from the second signal 2413. The resulting data set can be even less clear for the purpose of determining respiratory rate. The second respiratory rate 2416 determined from this data can be different from the first respiratory rate 2410, indicating that the first respiratory rate 2410 is incorrect.

The signal analysis algorithm 2414 can also optionally be run on a combination of the flow rate variation signal 2406 and the second signal 2413, for example, when the lookback period of the first lookback function 2412 is a full breath period. The current value of the parameter is the same as the value of the parameter from the lookback function. However, this addition method may not be able to remove certain artefacts in the flow rate variation signal 2406 that can be removed by the subtraction method. Any DC terms still remaining in the parameter variation signal can be doubled by the addition method, whereas the subtraction method can remove the DC terms.

A second lookback function 2418 can also be run on the flow rate variation signal 2406 to obtain a third signal 2419. The second lookback function 2418 can have a constant lookback period. The lookback period can be smaller than the full breath period. A short lookback period can allow more recent data to be analyzed, and reduce the inaccuracy in the single signal analyzing algorithm when the respiratory rate changes. Subtracting the flow rate variation signal 2406 of a short lookback period prior from the current flow rate variation signal 2406 can remove artefacts from the motor control. The resulting data set in the third signal 2419 can be effectively the first derivative of the measured flow rate. Another signal analysis algorithm 2420 can be run on the third signal 2419 to determine a third respiratory rate 2422, which can be similar to the first respiratory rate 2410 under normal breathing conditions.

In FIGS. 24B and 24E, the three signal analysis algorithms 2408, 2414, 2420 can be run at the same time. The three respiratory rates 2410, 2416, 2422 with corresponding magnitude data can be compared to see if the three respiratory rates 2410, 2416, 2422 are consistent. A final respiratory rate 2430 can be determined by calculating an average of the three respiratory rates 2410, 2416, 2422. The final respiratory rate 2430 can be a rolling average of all respiratory rate estimations from each signal analysis algorithm, for example, over the last twenty, fifteen, ten, or five seconds. The process including running three signal analysis algorithms can make the calculation of the final respiratory rate more robust than running a single signal analysis algorithm.

The controller can also calculate other variables, such as a plurality of cutoff values 2426, from the determination of the three respiratory rates 2410, 2416, 2422 with corresponding magnitude data. The plurality of cutoff values 2426 can include divergence, magnitude, and/or percentile cut-off values. The plurality of cutoff values 2426 can be used for determining a signal quality estimate 2428. Each of the variables can also be calculated as a rolling average, for example over the last twenty, fifteen, ten, or five seconds.

Divergence can be a distance between the three measured respiratory rates 2410, 2416, 2422. In normal breathing conditions, the divergence can be close to 0. In situations where the patient is talking or disconnected from the respiratory system, such when the patient has removed the patient interface or when the patient interface got disconnected, divergence can be as high as about 40. Magnitude can be an average of the maximum breathing magnitude determined from each of the three signal analysis algorithms 2408, 2414, 2420. Percentile can be a percentage of dominant frequencies that have a power of magnitude above a certain threshold. These cutoff values 2426 can each be converted into quality coefficients between 0 and 1, where 1 is the highest certainty possible.

The three quality coefficients are then multiplied together to give the single signal quality estimate 2428. The signal quality estimate 2428 can also be between 0 and 1. The signal quality estimate 2428 can be compared against a threshold. If the signal quality estimate 2428 exceeds the threshold, the final respiratory rate 2430 can be displayed. The final respiratory rate 2430 may only be displayed if a patient connected to the patient interface is detected, which can be assumed when the signal quality estimate 2428 exceeds the threshold, or determined using other processes described below. If the signal quality estimate 2428 does not exceed the threshold, the final respiratory rate 2430 also may not be displayed even if the patient is connected to the respiratory system. The low signal quality estimate can be caused by other scenarios, such as when the patient who is connected to the respiratory system is breathing through his or her mouth, talking, and/or eating.

Additionally, the signal quality estimate 2428 can have two thresholds. The first threshold can be used when the display of the respiratory device is not displaying a respiratory rate, and the signal quality estimate 2428 exceeding the threshold can trigger the device to begin displaying respiratory rate. The second threshold can be used when a respiratory rate is already being displayed, and the signal quality estimate 2428 dropping below the threshold can trigger the device to stop displaying the final respiratory rate. The first threshold can be higher than the second threshold. The two levels of thresholds can be advantageous over using a single threshold, by preventing situations where the display flickers on and off due to the signal quality estimate moving back and forth across the single threshold.

When processing the signal outputs to produce the flow rate variation signal 2406, the target flow rate 2404 can be replaced with a flow resistance multiplied by the motor speed of the flow generator. The flow resistance can be determined by first dividing the measured flow rate by the motor speed and then applying a low pass filter on the resulting value such as a moving average, Butterworth filter, Kalman filter, or extended Kalman filter. The flow rate variation parameter can be the difference of the measured flow rate and the product of the flow resistance and the motor speed.

Example Patient Detection Processes

As discussed above, when a patient is breathing through his or her nose into the patient interface of the respiratory system, a breathing signal is detected in the flow rate due to the flow resistance variation caused by inhalation and exhalation. There are also other scenarios where the breathing signal is obscured or diminished, such as when the patient who is connected to the patient interface of the respiratory system is breathing through his or her mouth, talking, and/or eating. The patient can also be disconnected from the breathing system such that there is no breathing signal in the gases flow parameter.

It can be advantageous for the respiratory system to be able to distinguish these different scenarios. Knowing whether the patient is connected to the respiratory system or is talking, eating, and/or breathing through his or her mouth can help the controller determine if the dominant frequency of the frequency analysis is the respiratory rate. Detection of patient disconnection can also have other applications, which will be described below in greater detail.

One way of determining that a patient is attached is to have a direct measure of signal noise, such as standard deviation, and compare the signal noise to a threshold. However, a few spurious or real data points can have a large effect on the calculation of the signal noise.

Another more robust way to determine whether a patient is connected can be based on the magnitude of a parameter variation signal described herein, such as the flow variation in the flow rate variation signal. The patient's breathing can produce larger fluctuations in the parameter variation, such as the flow rate variation, than would be by signal noise. The controller can count the number of data points of the parameter variation signal, such as the flow rate variation signal, that fall outside of a set of limits or boundary values. The controller can then weigh the count by the confidence that the data point falling outside of the boundary values was caused by the patient. The controller can also count each instance when the parameter variation, such as the flow rate variation, exceeds the boundary values as an indication that a patient is attached.

Figure 25:
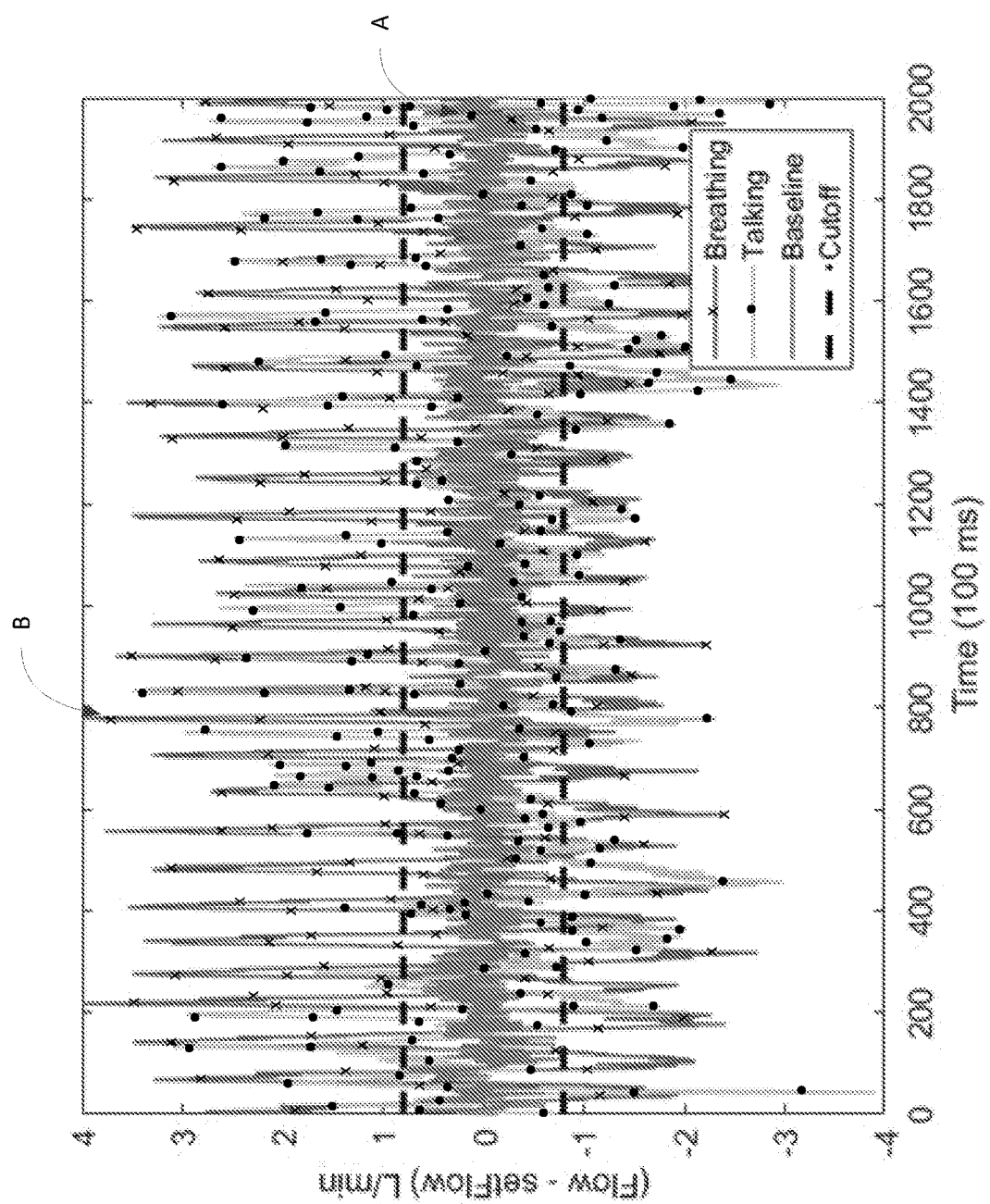
FIG. 25 illustrates an example flow rate variation signal.

FIG. 25 illustrates examples of how various factors influence the patient's flow rate variation, which is calculated as the difference between the measured flow rate and the target flow rate, over a 20 second period. As shown, a baseline flow rate variation A, which is not caused by the patient's breathing, can be substantially within the boundary values, whereas the flow rate variation B caused by the patient's breathing can be substantially outside the boundary values. The boundary values can be below the flow rate variation that is typically expected when a patient is connected, but above the maximum flow rate variation that is typically expected when the patient interface is disconnected from the patient, such as when sitting on a desk. As the flow rate variation can change with the changing target flow rate, the boundary value can be a variable that is defined by an equation such as below:

$$CUTOFF_{BREATHING} = CUTOFF_{MAX} - CUTOFF_{SLOPE}\left(\frac{MAX_{flow} - setFLOW}{MAX_{flow} - MIN_{flow}}\right)$$

where $CUTOFF_{BREATHING}$ is the boundary value, $CUTOFF_{MAX}$ is the highest possible boundary value, $CUTOFF_{SLOPE}$ is the difference between maximum and minimum boundary values, $MAX_{flow}$, is the highest flow rate that can be set on the device, $MIN_{flow}$, is the lowest flow rate that can be set on the device, and setFLOW is the target flow rate currently set by the user, such as the clinician or the patient.

Figure 26A:
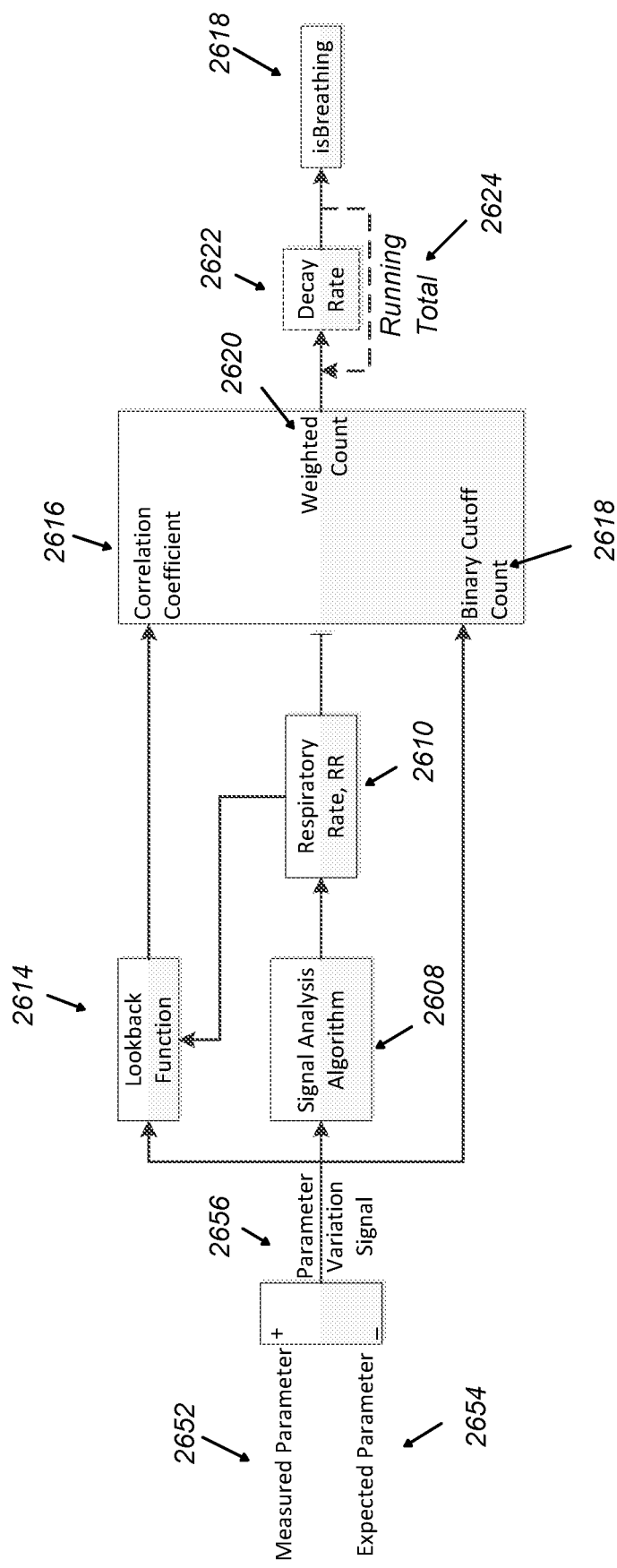
FIGS. 26A-26B illustrate example block diagrams for determining if patient breathing is detected.
Figure 26B:
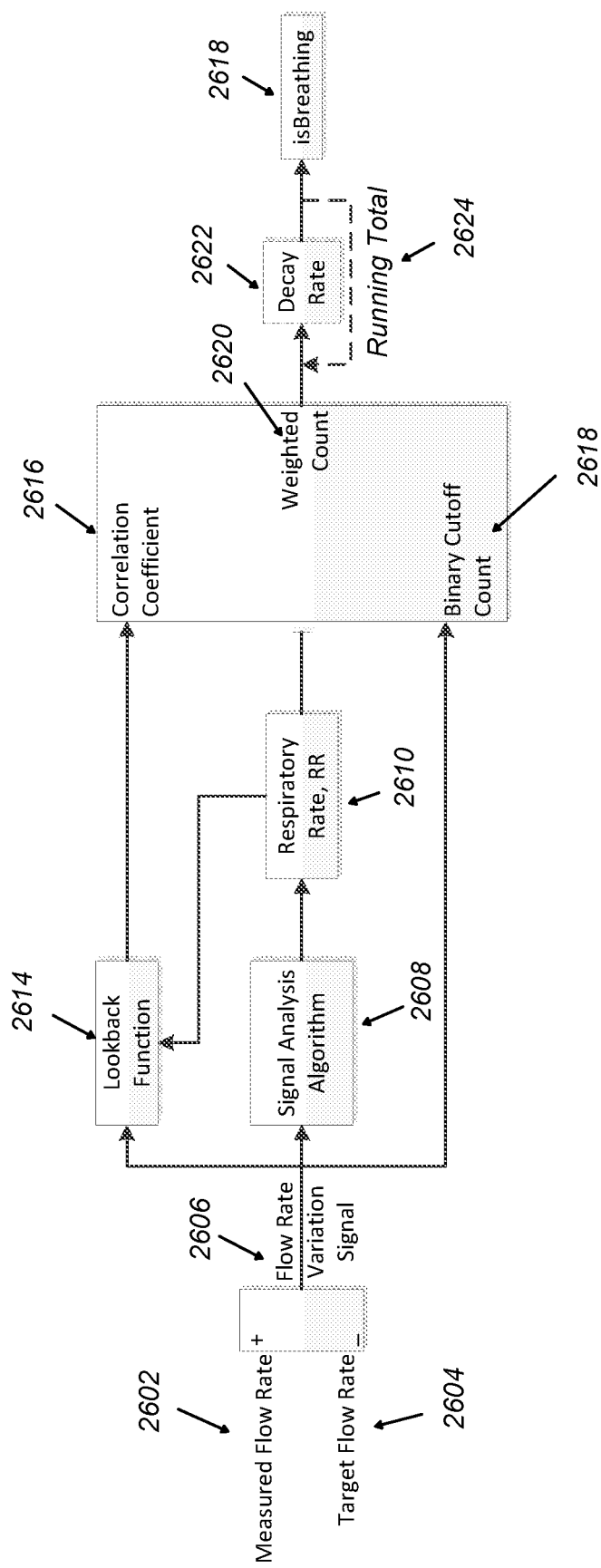

FIG. 26A illustrates another more robust way to determine whether a patient is connected based on the frequency analysis of the parameter variation signal. FIG. 26B illustrates another more robust way to determine whether a patient is connected based on the frequency analysis of the flow rate variation signal. FIG. 26B is an example of implementing the process as shown in FIG. 26A. Features of the processes in FIGS. 22, 24A-D, and 26A-B can be incorporated into one another.

As shown in FIG. 26A, similar to the processes described above, the controller can run a signal analysis algorithm 2608, such as the Goertzel algorithm, on the parameter variation signal 2656, which can be the difference between a measured parameter 2652 and the expected parameter value 2654 described above. A respiratory rate 2610 can be determined from the signal analysis algorithm 2608. The controller can run a lookback function 2614 on the parameter variation signal 2656. The lookback function 2614 can have a lookback period that is half of the breath period corresponding to the respiratory rate 2610. The controller can then determine a correlation coefficient 2616 by comparing a lookback signal after running the lookback function 2614 with the parameter variation signal 2656.

As shown in FIG. 26B, similar to the processes described above, the controller can run a signal analysis algorithm 2608, such as the Goertzel algorithm, on the flow rate variation signal 2606, which can be the difference between a measured flow rate 2602 and the target flow rate 2604. A respiratory rate 2610 can be determined from the signal analysis algorithm 2608. The controller can run a lookback function 2614 on the flow rate variation signal. The lookback function 2614 can have a lookback period that is half of the breath period corresponding to the respiratory rate 2610. The controller can then determine a correlation coefficient 2616 after comparing a lookback signal after running the lookback function 2614 with the signal 2606.

If the flow rate fluctuations are due to a patient being connected to the respiratory system, particularly a patient's breathing, lookback signal obtained from the lookback function 2614, and the parameter variation signal 2656 in FIG. 26A can be the conjugate of each other so that the correlation coefficient can be −1. If the flow rate fluctuations are due to a patient being connected to the respiratory system, particularly a patient's breathing, lookback signal and the flow rate signal 2606 in FIG. 26B can be the conjugate of each other so that the correlation coefficient can be −1. In order to allow for data with lower correlation coefficients (close to 0), such as from a low noise breathing signal, to still be counted, the equation for calculating a breath weighting coefficient can be defined as follows:

$$BREATH_{weightCOEFF} = C - correlationCOEFF$$

where C is a constant.

If the flow controller is the primary cause of flow variation (such as when one or more nasal prongs have been blocked or when the patient is disconnected), the parameter variation signal 2656 in FIG. 26A has a large DC term with a positive correlation coefficient, resulting in a breath weighting coefficient of 0 or lower, which can be counted as 0 by the controller. If the flow controller is the primary cause of flow variation (such as when one or more nasal prongs have been blocked or when the patient is disconnected), the flow rate variation in FIG. 26B has a large DC term with a positive correlation coefficient, resulting in a breath weighting coefficient of 0 or lower, which can be counted as 0 by the controller.

The controller can determine that a breathing signal has been detected and/or the patient is connected to the respiratory system 2618 only when the breath weighting coefficient is greater than 0.

As shown in FIG. 26A, the controller can also combine the analysis of breath signal detection in the time domain and the frequency domain to determine if the patient is connected to the respiratory system. The controller can perform a boundary count 2618 in the time-domain parameter variation signal 2656 in FIG. 26A as described above. The parameter variation signal 2656 can be measured against the boundary values and the controller can assign a value of 1 if it the parameter variation signal 2656 is outside the boundary values, or 0 if the parameter variation signal 2656 is within the boundary values. As shown in FIG. 26B, the controller can also combine the analysis of breath signal detection in the time domain and the frequency domain to determine if the patient is connected to the respiratory system. The controller can perform a boundary count 2618 in the time-domain flow rate variation signal as described above. The flow rate variation signal 2606 can be measured against the boundary values and the controller can assign a value of 1 if it the signal 2606 is outside the boundary values, or 0 if the signal 2606 is within the boundary values.

As shown in FIGS. 26A and 26B, the controller can multiply the breath weighting coefficient by the binary value from the boundary count 2618. If the boundary count is 0, the weighted count value 2620 is still 0. If the boundary count is 1, the weighted count value 2620 is non-zero and can be added to a running total 2624.

The running total 2624 can be compared to a threshold that is used to determine whether or not a patient is connected. The amount of time required to detect a patient breathing can be dependent on the level of the breath count total threshold. The controller can be configured to require a minimum amount of time for the running total to exceed a threshold indicating that the patient is connected to the system. The controller can also run the running total 2624 in a control loop. With each iteration of the control loop, the running total 2624 can be decayed 2622 at a rate. Decay the running total in a control loop can require the patient to be regularly breathing in order for the running total to remain above the threshold. The decay rate can be a constant and/or can be adjusted to change a minimum amount of time the patient needs to be breathing on the patient interface because the running total can reach the threshold. The minimum amount of time can be about 5 seconds to about 60 seconds, or about 10 seconds to about 40 seconds, or about 20 seconds.

With each cycle of the process in FIG. 26A or 26B, the running total can be tested against the threshold. If the threshold is exceeded, the controller can deem that the patient is connected to the system 2618.

Example Applications of Breathing Detection Processes

Determining whether or not the patient is connected to the patient interface can inform on the accuracy of the respiratory rate determination, and/or for other purposes. One of the other purposes is for the process of adherence tracking. Adherence tracking is an important factor for measuring patient compliance, particularly for the purpose of insurance reimbursement. Adherence tracking informs a user, clinician, insurance provider, or others, whether or not the patient is connected, and is a part of compliance measurement, which informs one whether or not the patient is using the prescribed therapy as intended. In order to err on the side of patient compliance, that is, it is more preferable to overestimate patient compliance than to underestimate it, any time at which the patient is detected as being connected to the patient interface will be logged in the electronic memory of the respiratory device as a minute in which the therapy was adhered to. In order for a minute to be logged as non-compliance, the running total must be below a threshold indicative of patient connection for the entire minute. The adherence tracking can further include recording on the memory the patient's respiratory rate measurements.

The respiratory device can keep a log of the total amount of time the patient spent attached to the device, and/or a log of how long the device was turned, on, with the adherence being a percentage of the duration when the device was turned on. The data relating to adherence can also be optionally accessible through a higher level settings menu. The menu can be password encrypted to prevent the patient from accessing it and/or otherwise protected. The compliance data can also optionally be logged for transmission to a server and/or be available for downloading by connecting the respiratory device to a second device (such as a computer or USB).

The clinicians can evaluate the efficacy of the therapy and/or the patient's progress in his or her respiratory functions using the patient's respiratory rate records. Hospitals can use the respiratory rate as a variable in an overall assessment of the patient's health. The respiratory rate data can also be used to predict the onset of a condition, such as a COPD exacerbation. Hospitals can analyze the respiratory rate in conjunction with other factors, such as oxygen saturation, delivered oxygen concentration, body temperature, blood pressure, heart rate and/or consciousness.

The patient disconnection detection can also be fed into a motor speed control signal. Normally an increased resistance in the flow can cause a decrease in the flow rate, which in turn can cause the controller to increase the motor speed to return the flow rate to its target value. Inversely, a reduced resistance in the flow can cause an increase in the flow rate, which in turn can cause the controller to reduce the motor speed to return the flow rate to its target value. If the controller knows that the flow resistance decrease is due to the patient disconnection, the controller can optionally allow the motor speed to remain unchanged despite the decrease in the flow resistance.

The patient disconnection detection can also be fed into an oxygen delivery control. If the patient temporarily takes off the patient interface, the patient's oxygen saturation can decrease and the controller of the respiratory device can begin to increase the oxygen concentration in the mixture of gases to be delivered to the patient. When the patient interface is reattached to the patient, the oxygen concentration in the gases flow can be high, which can result in a spike in the patient's oxygen saturation and be harmful to the patient. The patient disconnection detection can be factored into the oxygen delivery control of the device so that the controller does not begin increasing the oxygen delivery or the controller switches to a specific value when the patient is determined to be disconnected from the device.

Display of Respiratory Rate

Figure 27:
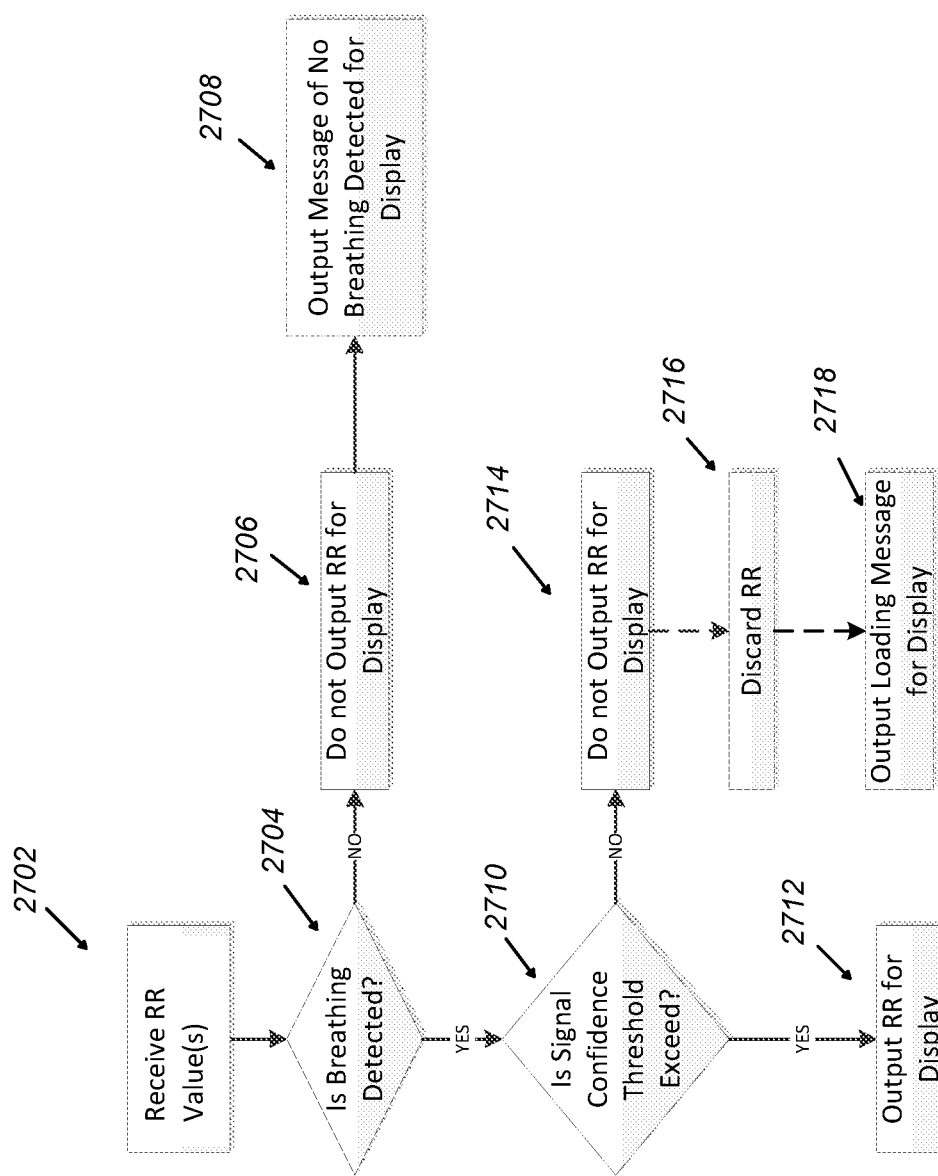
FIG. 27 illustrates an example flow chart for display of respiratory rate determination.

FIG. 27 illustrates an example process for display of the patient's respiratory rate information. At block 2702, the controller can receive respiratory rate value(s) from any of the algorithms described herein. In decision block 2704, the controller can determine if the patient is connected to the system. The controller can use any of the patient detection processes described above or any combinations thereof.

If the patient is not detected, the controller may not output or can stop outputting the respiratory rate value(s) for display at block 2706. The controller can also optionally output a message for display that no patient is detected at block 2708. An example of the message can be a "--" icon.

If the patient is detected, in decision block 2710, the controller can determine if the respiratory rate is measured to a required confidence, such as by comparing the signal quality estimate with a threshold as described above. If the signal confidence threshold is exceeded, the controller can output the respiratory rate value(s) for display at block 2712. If the signal confidence threshold is not exceeded, the controller may not output or can stop outputting the respiratory rate value(s) for display at block 2714. As described above, the controller can have two thresholds, one for when the system is already displaying respiratory rate values and the other one for when the system is not displaying respiratory rate values. The controller can also assess a signal quality of the respiratory rate estimation by calculating the difference between the latest respiratory rate estimation and a filtered respiratory rate estimation. The difference is then filtered to obtain the recent changes in respiratory rate. The controller can also assess the signal quality of the respiratory rate estimation by calculating the difference between the latest breath period estimation and a filtered breath period estimation. The difference is then filtered to obtain the recent changes in breath period. If the recent changes in respiratory rate or breath period, or a combined recent changes in respiratory rate and recent changes in breath period, are below a threshold, the respiratory rate estimation is considered to be of significant or sufficient signal quality. Higher changes can be indicative of a lower or poorer signal quality. The controller can also assess the signal quality based in part on a magnitude of the frequency transform (such as the Goertzel transform) associated with the estimated respiratory rate. Higher magnitudes can be indicative of a higher signal quality. The evaluation of signal quality can be used in determining whether or not the estimated respiratory rate is displayed, such as on a graphical user interface of the respiratory device examples disclosed herein. The controller can output the respiratory rate estimation for display if the estimation is deemed to be of significant or sufficient signal quality. The controller can also assess the signal quality of the respiratory rate estimation by calculating the running variance in the respiratory rate estimation, breath period estimation, or both. For a lower value of respiratory rate or breath rate, a small change in the respiratory rate (for example, a change from 4 breaths per minute to 5 breaths per minute) can result in a large variation, which can lead to a lower, poorer, or less significant signal quality, than when the estimated respiratory rate is larger (for example, a change from 15 breaths per minute to 16 breaths per minute). The converse is true for the breath period. Therefore, it can be preferable to consider both the variance in the respiratory rate and the variance in the breath period in determining signal quality.

The determination of whether a respiratory rate is correctly estimated can err on the side of being incorrect, unlike the patient detection, which can err on the side of patient attachment to the patient interface. It is safer to assume patient connection if the controller cannot be dispositive of whether the patient is connected. It is also safer to not display a respiratory rate estimation if the estimation may be incorrect.

The controller can optionally discard the respiratory rate values at block 2716. The controller can also optionally output a loading message for display at block 2718. An example of the loading message can be a swirling circle indicator or others.

The respiratory rate over time can be displayed on a graph. The graph can show how the respiratory rate changes over time. The respiratory rate displayed can be an averaged respiratory rate, for example, of the last 45, 30, 20, or 15 seconds. The graph can update in real time as new data becomes available. The time scale of the graph can be fixed, for example, to at least a few hours, or be adjusted to fit the size of the available dataset. The device can have a maximum time scale, for example, of at least a few hours or more.

The graph can be displayed on the graphical user interface described herein. The graph can be on the default display or be excluded from the default display but accessible through interaction with the graphical user interface. For example, a user can press a touch screen or a button on the device, where selecting the display of current respiratory rate brings up a graph of respiratory rate over time.

The respiratory rate data can be communicated to a server. The data can include the instantaneous breathing rate and/or the averaged respiratory rate. The data can be accompanied by the breathing magnitude data and/or an indicator of what respiratory rate data met the threshold for reliability, for example, as determined using the processes described herein. The device can be programmed to only send respiratory rate data that met the threshold for reliability.

The respiratory device can display other information based on the patient's respiratory values. The respiratory rate data, such as the instantaneous and/or averaged rate, can be used on its own to output an alarm to clinicians of patient condition, such as that the patient requires immediate attention, and/or to output for display an alarm predicting the onset of a condition, such as a COPD exacerbation. The alarm can be visual, audial and/or tactile. The device can output different alarms to indicate different problems. The device can also communicate the alarm to a server.

The device can output an alarm of a change in respiratory rate. The change can be identified by comparing one or more recent values with one or more previous values. The device can output an alarm when a specific number of the recent values differ from a specific number of previous values by a specific amount. The one or more recent values can be reduced to a single value, such as the mean, median, mode, highest, lowest or any other selection criteria. One or more previous values can also be reduced to a single value, such as the mean, median, mode, highest, lowest or any other selection criteria. The previous values can be from a fixed amount of time before the recent value. The previous values can also be fixed, such as a set of values measured at the start of treatment. The previous values can also contain all data outside of the one or more recent values.

The threshold for the alarm can be a fixed change between the one or more previous values and the one or more recent values and/or a percentage change between the one or more previous values and the one or more recent values. The one or more recent values can be compared to one or more thresholds having fixed respiratory rates. The fixed respiratory rates can be preprogramed, set by a clinician, and/or based on one or more patient parameters. The patient parameters can include the patient's affliction and/or other parameters about the patient, such as weight, age and/or gender. The patient's affliction can include chronic obstructive pulmonary disease (COPD), pneumonia, asthma, bronchopulmonary dysplasia, heart failure, cystic fibrosis, sleep apnea, lung disease, trauma to the respiratory system, and/or acute respiratory distress. The device can have one or more different alarms for one or more different thresholds.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A respiratory system configured to deliver a respiratory therapy to a patient, the system also configured to provide information related to the patient, the system comprising:
    a respiratory device configured to deliver nasal high flow therapy, the respiratory device comprising a controller, wherein the controller is configured to:
        receive measurements of a first parameter of a flow of gases or representative of performance of a component of the respiratory device, wherein the first parameter is a flow rate;
        receive measurements of a second parameter of a gases flow or representative of performance of a component of the respiratory device, wherein the second parameter has an assumed effect on the first parameter wherein the first parameter is calculated independent of the second parameter;
        determine whether the assumed effect is valid; and
        discard the first parameter from a validated first parameter dataset in response to the assumed effect being invalid, the controller configured to use the validated first parameter dataset to estimate a respiratory rate of the patient.

2. The system of claim 1, wherein the controller is further configured to estimate whether the patient is wearing a patient interface of the system.

3. The system of claim 1, wherein the respiratory device further comprises a blower including a motor, wherein the second parameter is a motor speed.

4. The system of claim 3, wherein the assumed effect is invalid if the motor speed is below a minimum threshold.

5. The system of claim 3, wherein the assumed effect is invalid if recent changes in the motor speed are above a change in a motor speed threshold.

6. The system of claim 1, wherein the second parameter is pressure.

7. The system of claim 1, wherein the flow of gases comprises ambient air.

8. The system of claim 7, wherein the flow of gases comprises a supplementary gas.

9. The system of claim 8, wherein the supplementary gas comprises oxygen.

10. The system of claim 8, wherein the controller is configured to measure a composition of the flow of gases after the ambient air and the supplementary gas have been mixed.

11. The system of claim 10, wherein the assumed effect is invalid if recent changes in the composition of the flow of gases are above a change in the composition of the flow of gases threshold.

12. The system of claim 8, wherein the controller is configured to measure a flow rate of the supplementary gas into the respiratory device.

13. The system of claim 12, wherein the assumed effect is invalid if recent changes in the flow rate of the supplementary gas are above a change in the flow rate of a supplementary gas threshold.

14. The system of claim 12, wherein the controller is configured to control the flow rate of the supplementary gas into the respiratory device.

15. The system of claim 1, wherein if the assumed effect is valid, the controller is configured to estimate the respiratory rate of the patient using the assumed effect, wherein the controller is further configured to subtract the assumed effect from the first parameter to output a modified first parameter and estimate the respiratory rate of the patient based on the modified first parameter.

16. The system of claim 1, wherein the controller is configured to perform a frequency analysis of the validated first parameter dataset to estimate the respiratory rate of the patient.

17. The system of claim 1, wherein the respiratory system further comprises a non-sealed interface.

* * * * *